(12) United States Patent
Ehlert et al.

(10) Patent No.: US 12,692,555 B2
(45) Date of Patent: *Jul. 28, 2026

(54) MARKER ASSISTED SELECTION OF TRAITS FOR PRODUCING MEAL FROM *Brassica napus*

(71) Applicant: Corteva Agriscience LLC, Indianapolis, IN (US)

(72) Inventors: Zoe Christina Ehlert, Saskatoon (CA); Joshua A. Flook, Indianapolis, IN (US); Daniel Garcia, Indianapolis, IN (US); Donna Carolynn Knievel, Saskatoon (CA); Cherie Ochsenfeld, Indianapolis, IN (US); Thomas G. Patterson, Indianapolis, IN (US); Ryan Preuss, Indianapolis, IN (US); Syed Masood Rizvi, Saskatoon (CA); Van L. Ripley, Grandora (CA); Steve Rounsley, Indianapolis, IN (US); Shunxue Tang, Carmel, IN (US); Muhammad Tahir, Saskatoon (CA); Michelle Wiggins, Westfield, IN (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/344,018

(22) Filed: Jun. 29, 2023

(65) Prior Publication Data

US 2023/0407417 A1 Dec. 21, 2023

Related U.S. Application Data

(63) Continuation of application No. 17/064,284, filed on Oct. 6, 2020, now Pat. No. 11,713,490, which is a continuation of application No. 15/731,561, filed as application No. PCT/US2015/066813 on Dec. 18, 2015, now Pat. No. 10,791,692.

(60) Provisional application No. 62/093,963, filed on Dec. 18, 2014.

(51) Int. Cl.
| | |
|---|---|
| *A01H 5/10* | (2018.01) |
| *A01H 1/04* | (2006.01) |
| *A01H 6/20* | (2018.01) |
| *C12Q 1/6895* | (2018.01) |
| *A23L 19/00* | (2016.01) |

(52) U.S. Cl.
CPC ............ *C12Q 1/6895* (2013.01); *A01H 1/04* (2013.01); *A01H 1/045* (2021.01); *A01H 5/10* (2013.01); *A01H 6/202* (2018.05); *A23L 19/00* (2016.08); *C12Q 2600/13* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 10,791,692 B2 * | 10/2020 | Tang ......................... | A01H 1/04 |
| 11,713,490 B2 * | 8/2023 | Tang .................... | C12Q 1/6895 |
| | | | 800/267 |
| 2010/0303999 A1 | 12/2010 | Chungu et al. | |
| 2014/0220564 A1 | 8/2014 | Zhang et al. | |

FOREIGN PATENT DOCUMENTS

WO 2016100883 A1 6/2016

OTHER PUBLICATIONS

Akhov L., et al., "Proanthocyanidin Biosynthesis in the Seed Coat of Yellow-Seeded, Canola Quality *Brassica napus* YN01-429 is Constrained at the Committed Step Catalyzed by Dihydroflavonol 4-Reductase," This Paper is One of a Selection of Papers Published in a Special Issue from the National Research Council of Canada, BOTANY = BOTANIQUE, Jun. 15, 2009, vol. 87, No. 6, pp. 616-625, DOI:10.1139/B09-036, ISSN 1916-2790, XP055472407.

Badani A.G., et al., "Colocalization of a Partially Dominant Gene for Yellow Seed Colour with a Major QTL Influencing Acid Detergent Fibre (ADF) Content In different Crosses of Oilseed Rape (*Brassica napus*)," Genome, Dec. 2006, vol. 49, No. 12, pp. 1499-1509, DOI:10.1139/g06-091, XP009503939.

Chalhoub B., et al., "Early Allopolyploid Evolution in the Post-Neolithic *Brassica napus* Oilseed Genome," Aug. 22, 2014, Science, vol. 345, No. 6199, pp. 950-953, 6 Pages.

Clarke W.E., et al., "A High-Density SNP Genotyping Array For *Brassica napus* and its Ancestral Diploid Species Based on Optimised Selection of Single-locus Markers in the Allotetraploid Genome," Theoretical and Applied Genetics, 2016, vol. 129, No. 10, pp. 1887-1899, Supplementary Table 1 of Clarke et al.

Clarke W.E., et al., "Genomic DNA Enrichment Using Sequence Capture Microarrays: A Novel Approach to Discover Sequence Nucleotide Polymorphisms (SNP) in *Brassica napus* L", PLOS ONE, 2013, vol. 8, No. 12, pp. 1-14, XP055834905.

(Continued)

*Primary Examiner* — Medina A Ibrahim

(57) ABSTRACT

A method for identifying a quantitative trait locus associated with desirable nutritional traits in canola includes: analyzing a population of canola plants or germplasm for desirable nutritional traits; determining the genotype of the canola plants or germplasm using at least one marker selected from the group consisting of SEQ ID NO:1 through SEQ ID NO:111; mapping the canola plants or germplasm for the presence of a quantitative trait locus (QTL) associated with the markers; and associating the QTL with the desirable nutritional trait. An isolated and/or recombinant nucleic acid includes a sequence associated with a quantitative trait locus (QTL), wherein the QTL is associated with a desirable nutritional trait in a canola plant or germplasm and wherein the QTL is further associated with at least one marker selected from the group consisting of SEQ ID NO:1 through SEQ ID NO:111.

15 Claims, 8 Drawing Sheets

Specification includes a Sequence Listing.

(56) References Cited

OTHER PUBLICATIONS

Declaration of Snowdon R.J., EP Opposition No. 3234197B1, dated Jul. 26, 2021, Submitted in Opposition of EP3234197B1 on Aug. 9, 2021, 2 Pages.

Edwards D., et al., "Accessing Complex Crop Genomes with Next-Generation Sequencing," Theoretical and Applied Genetics, 2012, 2013, vol. 126, pp. 1-11.

EP Opposition EP3234197B1_Cited Document D18_Alignment of Sequence rs# 21212 of Wang et al. 2016 8 with SEQ ID Nos. 14-17 of the Patent Highlighting Relevant SNPs, Submitted on Jan. 2, 2022.

EP Opposition EP3234197B1—Cited Document Maiwald D7b Alignment of Selected Sequences of Opposed Patent in SRX377527 and EP3234197B1, 14 Pages.

EP Opposition EP3234197B1—Cited Document D8a, Alignment of Selected Sequences in Brassica napus 60K Illumina Infinium TM SNP Array and EP3234197B1,7 Pages.

EP Opposition No. EP3234197B_Cited Document D15_p. 7 of Amendment filed for U.S. Appl. No. 15/731,561 dated Apr. 29, 2020.

"Infinium Assay Workflow," Illumina, Oct. 11, 2021, 2 Pages, Retrieved from URL: http://www.bea.ki.se/documents/workflow_infinium.pdf.

International Search Report and Written Opinion for International Application No. PCT/US2015/066813, mailed Apr. 11, 2016, 12 Pages.

Liu L., et al., "A High-Density SNP Map for Accurate Mapping of Seed Fibre QTL in Brassica napus L," PLoS One, Dec. 2013, vol. 8, No. 12(e83052), pp. 1-9.

McEntyre J., et al., "Chapter 5: The Single Nucleotide Polymorphism Database (dbSNP) of Nucleotide Sequence Variation," By Adrienne Kitts, The NCBI Handbook [Internet] Bethesda (MD): National Center for Biotechnology Information (US), Created on Oct. 9, 2002, 25 Pages, Last Updated Feb. 2, 2011.

NCBI: "Brasica napus Strain DH12075 (rape)," Brassica napus Strain: DH12075 Targeted Locus (Loci), Submitted on Sep. 11, 2013, 1 Page.

NCBI Genbank: "Predicted Brassica rapa 2-Isopropylmalate Synthase 1, Chloroplastic-Like (LOC103842698)," Sequence, NCBI/GenBank Accession No. XM_009119363.3, Dec. 7, 2020, 2 Pages.

NCBI Genbank: "Predicted Brassica rapa post-GPI Attachment to Proteins Factor 3-Like (LOC103842843), Transcript Variant X2, mRNA," NCBI/GenBank Accession No. XM_009119508.3, Dec. 7, 2020, 2 Pages.

NCBI: "SRX377527, YN429 Sequence Capture," Jul. 17, 2014, 1 Page.

Nelson S.C., et al., "Is 'Forward' the Same as 'Plus'?. . . and Other Adventures in SNP Allele Nomenclature," Trends in Genetics, Aug. 2012, vol. 28, No. 8, pp. 361-363, 6 Pages.

Nesi N., et al., "Genetic and Molecular Approaches to Improve Nutritional Value of Brassica napus L. seed," Comptes Rendus Biologies, 2008, vol. 331, pp. 763-771, doi:doi:10.1016/j.crvi.2008.07.018, XP025474044.

Notice of Opposition Submitted in European Patent Office for EP3234197B1, dated Aug. 9, 2021, 45 Pages.

Opposition of EP3234197B1_Cited Document Maiwald D8a Alignment of Selected Sequences in ROW 84 of Table S4 of Wang et al. 2015 and EP3234197B1, Submitted on Aug. 9, 2021, 2 Pages.

Oraby H.F., et al., "Impact of Suppressing the Caffeic Acid O-Methyltransferase (COMT) Gene on Lignin, Fiber, and Seed Oil Composition in Brassica napus Transgenic Plants," European Food Research and Technology, Published on Dec. 4, 2014, 2015, vol. 240, pp. 931-938, DOI:10.1007/s00217-014-2397-3, XP055834900.

Relf-Eckstein., et al., "Meal Quality Improvement in Brassica napus Canola Through the Development of Low Fibre Yellow-Seeded) Germplasm," Feed and Industrial Raw Material, 2007, pp. 289-291.

Response to Notice of Opposition in European Patent Office for EP3234197B1, dated Jan. 2, 2022, 16 Pages.

Shoaib M., et al., "Dry Matter Yield and Forage Quality of OAT, Barley and Canola Mixture," Pakistan Journal of Agricultural Sciences, 2014, vol. 51, No. 2, pp. 443-449.

Slominski B.A., et al., "Low-Fiber Canola. Part 1. Chemical and Nutritive Composition of the Meal," Journal of Agricultural and Food Chemistry, 2012, vol. 60, pp. 12225-12230.

Slominski B.A., "Nutritive Value of Canola Meal: The Dietary Fibre Story," University of Manitoba, Jul. 2015, 55 Pages, URL: https://www.agwest.sk.ca/IRC2015/BSlominskiCanolameal.pdf, XP055834548.

Somers D.J., et al., "Identification of a Major Gene and RAPD Markers for Yellow Seed Coat Colour in Brassica napus," Genome, 2001, vol. 44, No. 6, pp. 1077-1082.

Wang J., et al., "Genome-Wide Analysis of Seed Acid Detergent Lignin (ADL) and HULL Content in Rapeseed (Brassica napus L.)," PLOS ONE, Dec. 16, 2015, vol. 10, No. 12(e014045), 18 Pages.

Yan et al., "Co-Location of Seed Oil Content, Seed Hull Content and Seed Coat Color QTL in Three Different Environments in Brassica napus L," Euphytica, 2009, vol. 170, pp. 355-364, DOI: 10.1007/s10681-009-0006-5, XP019748260.

* cited by examiner

WI_A: White Index from AAFC
WI_D: White Index from DAS
L: Hunter Lab Lightness Index L from DAS
ADF_A: ADF (NIR) data from AAFC
ADF_W: ADF (Wet Chemistry) data from DAS LOD Threshold: 3.0

WI_A: White Index from AAFC
WI_D: White Index from DAS
L: Hunter Lab Lightness Index L from DAS
ADF_A: ADF (NIR) data from AAFC
ADF_W: ADF (Wet Chemistry) data from DAS LOD Threshold: 3.0

1 : WI_A
2 : WI_D
3 : L
6 : ADF_A
7 : ADF_W

ADF_M1: ADF (NIR, model 1) data from DAS
ADF_M2: ADF (NIR, model 2) data from DAS
WI: White Index data from DAS
L: Hunter Lab Lightness Index L from DAS LOD Threshold: 3.0

ADF_M1: ADF (NIR, model 1) data from DAS
ADF_M2: ADF (NIR, model 2) data from DAS
WI: White Index data from DAS
L: Hunter Lab Lightness Index L from DAS LOD Threshold: 3.0

MARKER ASSISTED SELECTION OF TRAITS FOR PRODUCING MEAL FROM *Brassica napus*

CROSS-REFERENCE TO RELATED APPLICATIONS

This application is a continuation of U.S. patent application Ser. No. 17/064,284, filed on Oct. 6, 2020, which is a continuation of U.S. patent application Ser. No. 15/731,561, filed on Jun. 27, 2017 and issued on Oct. 6, 2020 as U.S. Pat. No. 10,791,692, which is a national phase entry under 35 U.S.C. § 371 of International Patent Application PCT/US2015/066813, filed on Dec. 18, 2015, which claims priority to U.S. Provisional No. 62/093,963, filed Dec. 18, 2014, each of which is incorporated in their entirety by reference herein.

INCORPORATION BY REFERENCE OF MATERIAL SUBMITTED ELECTRONICALLY

The official copy of the sequence listing is submitted concurrently with the specification via EFS-Web as an XML-formatted sequence listing with a file named file named "111150-US-CON-2_ST26v2", created on Sep. 11, 2023, having a size of 190,448 bytes. This sequence listing is part of the specification, and is incorporated by reference herein in its entirety.

TECHNICAL FIELD

The disclosure relates to fine mapping of quantitative trait loci (QTLs) associated with low fiber content and YSC traits and identification of SNP markers for marker assisted selection of these traits in *Brassica napus*.

BACKGROUND

Canola (*Brassica napus* L., 2n=4x=38, AACC), an allotetraploid formed from diploids *B. rapa* (2n=2x=20, AA) and *B. oleracea* (2n=2x=18, CC), is one of the most important vegetable oilseed crops in the world, especially in China, Canada, the European Union and Australia. Canola meal, the fraction of the seed remaining after crushing and oil extraction, is approximately 55% of the volume of canola seed.

Canola meal consists of several components including protein, fiber, residual oil, carbohydrates, and anti-nutritional factors. Canola meal contains approximately 75% of the protein of 48% protein soybean meal, 80% of the energy value, and 300% of the crude fiber, as well as higher levels of anti-nutritional factors such as glucosinolates, tannins, phytic acid, sinapine and erucic acid, and is sold as livestock feed at 60%-70% of the price of soybean meal. See, e.g., Hickling (2007) Canola meal competitive situation and Canola Council of Canada goals, Canola Meal Research Meeting, Saskatoon, Canada; Newkirk (2009) Canola meal feed industry guide (4th Edition). The relatively high fiber content of canola meal is a significant limiting factor for its use in monogastric animal species (Hickling, 2007; Newkirk, 2009). Since meal comprises half of the seed volume of canola, and demand for biodiesel could drive a 67% increase in rapeseed seed production from 2006 to 2015 (Hickling, 2007), there is a need to modify the compositional properties of canola meal and thereby increasing its nutritional value relative to soybean.

Scientists at Agriculture and Agri-Foods Canada (AAFC) have developed yellow seed coat (YSC) lines (YN86-37, YN90-1016, YN97-262 and YN01-429) of low hull proportion with thinner seed coat, low fiber and high oil compared to the black seed coat (BSC) canola (Rakow et al., 2011). Feeding studies, comparing yellow seeded canola meal from AAFC line YN01-429 to *B. juncea, B. rapa*, and brown-seeded *B. napus*, demonstrated the advantages of YSC *B. napus* line such as higher protein, lower fiber, increased amino acid digestibility and metabolizable energy content, and improved nutrient and energy utilization based on feed to gain ratio in broiler chickens and monogastric animal species (Hickling, 2009; Slominski et al., 2010).

The breeding of low fiber content has been greatly hampered by a poor understanding of the inheritance and stability of the low fiber content traits, as well as a lack of robust, high-throughput markers tightly linked to the trait. Due to allotetraploidy, effect of multiple genes, maternal effects and environmental effects, the inheritance of low fiber content trait is complex, and identification of markers tightly linked to this trait is very challenging. Somers et al, (2001) reported identification of eight random amplified polymorphic DNA (RAPD) markers for a major gene (pigment1) associated with yellow seed coat trait from YSC line YN90-1016, the low fiber content source of YN97-262 and YN01-429 used in the applicant's Low Fiber breeding program (Rakow et al., 2011). The major gene explained 72.3% of the variation in seed color, while two additional genes that appeared to be additive explained 21.5% of the color variation (Somers et al., 2001).

It has been suggested that the low fiber content of AAFC YSC line YN01-429 and its lineage might be controlled by three recessive genes (Kubik and Thompson, 2009). Current selection of lower fiber canola lines has primarily been based on fiber content data obtained using cost and labor intensive analytical methods, or seed coat color, because of its high correlation with low fiber in the AAFC YSC lines YN97-262 and YN01-429.

SUMMARY OF DISCLOSURE

A particular embodiment of the invention includes a method for identifying quantitative trait locus associated with desirable nutritional traits in canola. The method includes analyzing a population of canola plants or germplasm for desirable nutritional traits. The genotype of the canola plants or germplasm is determined using at least one marker selected from the group consisting of SEQ ID NO:1 through SEQ ID NO:111. The canola plants or germplasm are mapped for the presence of a quantitative trait locus (QTL) associated with the markers. The QTL is associated with the desirable nutritional trait.

Another embodiment relates to an isolated and/or recombinant nucleic acid having a sequence associated with a QTL. The QTL is associated with a desirable nutritional trait in a canola plant or germplasm. The QTL is further associated with at least one marker selected from the group consisting of SEQ ID NO:1 through SEQ ID NO:111.

Yet another embodiment relates to a method for selecting a canola plant or germplasm that comprises desirable nutritional traits. The method includes detecting in the canola plant or germplasm at least one marker linked with a QTL that is selected from the group consisting of SEQ ID NO:1 through SEQ ID NO:111, wherein the QTL is associated with a desirable nutritional trait in the canola plant or germplasm. A canola plant or germplasm is then selected based on the presence of the marker.

The foregoing and other features will become more apparent from the following detailed description of several embodiments, which proceeds with reference to the accompanying figures.

DISCLOSURE

Described herein are high-throughput single nucleotide polymorphism (SNP) markers and high-density genetic maps for fine mapping and validation of quantitative trait loci (QTL) underlying fiber content and seed coat color traits. In some embodiments, SNP markers tightly linked to fiber content and seed coat color traits may be used for marker-assisted selection (MAS) of desirable nutritional traits in yellow-seeded canola (YSC) lines. In particular embodiments, the YSC line may be AAFC YSC line YN01-429 and its lineage.

Also disclosed is a method of leveraging SNP markers and high-density genetic maps based on fiber content and seed coat color traits from AAFC YSC line YN01-429, using an extensive set of phenotypic data of two DH populations. In a particular embodiment, a major QTL, which explains 59.2% to 74.7% of the variance of fiber content and seed coat color traits, is described on N09 in two DH populations, and a minor QTL, which explains 1.4% to 7.2% of the variance of fiber content and seed coat color traits, is described on N11 in two DH populations. High correlation ($R^2$=0.67-0.85) exists between seed coat color traits (WI and L) and ADF content in both populations.

Figure 8:
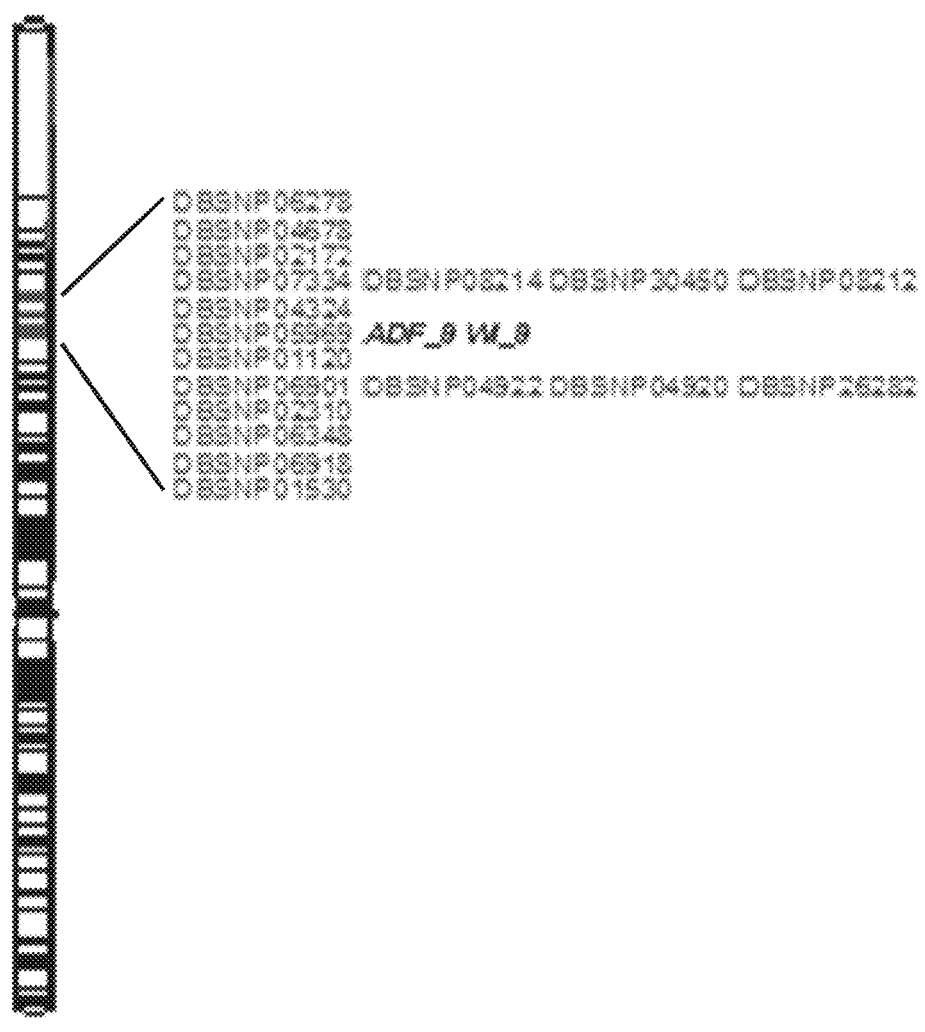
FIG. 8 shows a map of N09 constructed with N09 of YDN, YSC and TN DH populations, showing 18 SNP markers identified within 0.0-4.9 cM to a major QTL underlying fiber content (ADF_9) and seed coat color (WI_9) on N09.

Also disclosed herein are 18 SNP markers within 0.0-4.9 cM of the major fiber content and seed coat color QTL on N09 (see FIG. 8), and 40 SNP markers within 0.0-4.1 cM of the minor fiber content and seed coat color QTL on N11, which may be used in embodiments for marker-assisted selection of complex low fiber content and YSC traits from YSC line YN01-429 and its lineage, and thus may improve the breeding process of canola lines with low ADF content if YN01-429 or it lineage is used as a low fiber content source in breeding programs.

An Low Fiber product which aims to improve the nutritional value of commercial canola meal to 85-90% of the value of 48% protein soybean meal by increasing protein content (from 36% to 44%) and true metabolizable energy (TME) (a 16%-20% increase), and decreasing fiber content (from 15-19% to less than 10%) has been developed. These improvements are anticipated to increase the nutritive value of canola meal, particularly in monogastric species, and should allow increasing dietary inclusion rates.

YSC lines (YN86-37, YN90-1016, YN97-262 and YN01-429) of low hull proportion with a thinner seed coat, low fiber and high oil as compared to black seed coat (BSC) canola (Rakow et al., 2011) also have been developed. Feeding studies comparing yellow-seeded canola meal from AAFC line YN01-429 to *B. juncea, B. rapa*, and brown-seeded *B. napus* have demonstrated the advantages of the YSC *B. napus* line, including higher protein, lower fiber, increased amino acid digestibility and metabolizable energy content, and improved nutrient and energy utilization based on feed to gain ratio in broiler chickens and monogastric animal species (Hickling, 2009; Slominski et al., 2010).

Combinations of the yellow seeded/low fiber traits from YSC lines YN97-262 and YN01-419 with the Omega 9 fatty acid profile, as well as other desirable agronomic and seed quality attributes, have been studied.

I. Mapping and Validation of Low Fiber Content and YSC Traits from YN01-429

In a preferred embodiment, the disclosure describes a method for identifying and mapping quantitative trait loci (QTL) associated with low fiber content and yellow seed coat (YSC) traits in *Brassica napus* using single-nucleotide polymorphism (SNP) markers. In embodiments, the QTLs are defined in YSC line YN01-429. In some embodiments, the markers may be used for marker-assisted selection of low fiber content and YSC traits derived from YSC line YN01-429 and its lineage.

SNP markers and high-density genetic maps were leveraged, and fiber content and seed coat color traits were fine mapped and validated from AAFC YSC line YN01-429 with an extensive set of phenotypic data from two dihaploid (DH) populations. These experiments are outlined in greater detail in Examples 1-5. Two DH populations, YSC and YDN, were developed from spring canola line crosses. The 183 DH lines of the YSC population were developed from a cross between AAFC yellow seeded/low fiber line YN01-429 and DAS Nexera black seeded/high fiber variety Nex828, and grown along with the two parents in paired row plots at the AAFC Saskatoon research farm and the DAS Rosthern research farm in Canada in 2007 for phenotyping. Seed samples from two locations were analyzed by AAFC using near-infrared spectroscopy (NIR) ADF (named ADF_A in FIGS. 3 and 4) and using Hunter lab for seed coat color White Index (named WI_A in FIGS. 3 and 4) measurement in 2007. The population was also analyzed by DAS Analytical Technologies Group in Indianapolis for ADF (named ADF_A in FIGS. 3 and 4) using the AOAC reference method (AOAC Official Method 973.18) and by DAS Bioprocess Group in Indianapolis for seed coat color White Index (named WI_D in FIGS. 3 and 4) and Hunter Lab Lightness Index (named L in FIGS. 3 and 4) measurement in 2011. The 400 DH lines of the YDN population were developed from a cross between YN01-429 and DAS Nexera black seeded/high fiber variety DN051493. The YDN population was grown along with the two parents at Pike Lake and Cudworth, Canada in 2011 for phenotyping. Seed samples were analyzed for ADF (named ADF_M1 and ADF_M2 in FIGS. 5 and 6), seed coat color White Index (named WI in FIGS. 5 and 6) and Hunter lab Lightness Index (name L in the FIGS. 5 and 6). A third DH population of 181 DH lines (named TN population) from a cross between Tapidor (a European winter cultivar) and Ningyou7 (a Chinese semi-winter cultivar) was added for consensus map construction in addition to YSC and YDN populations for QTL mapping of fiber content and seed coat color traits; TN population did not segregate for fiber content and seed coat color traits. The three DH populations were genotyped with 12,000 SNP markers and a consensus map was constructed with individual map of the YSC, YDN and TN populations. Composite Interval Mapping (CIM) was used for a whole genome QTL scan. After QTL mapping, the SNP markers within 0.0-5.0 cM of the QTL underlying fiber content and seed coat color traits were converted to KASPar assays for MAS of these traits derived from YN01-429 and its lineage.

Figure 1:
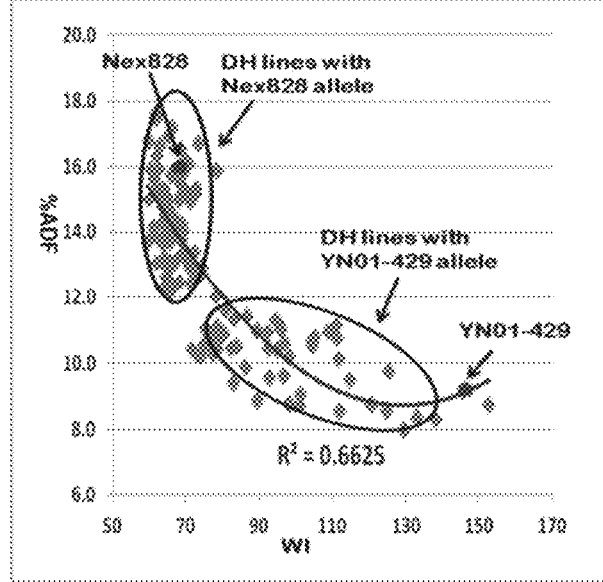
FIG. 1 shows the distribution of White Index (WI) and % ADF in Nex828 x YN01-429 (YSC) DH lines. The left figure shows the White Index (WI) of seed coat color plotted against % of ADF in canola seed. The right figure shows the distribution of % ADF among DH lines. The number in bracket indicated % of ADF in canola seed.
Figure 1:
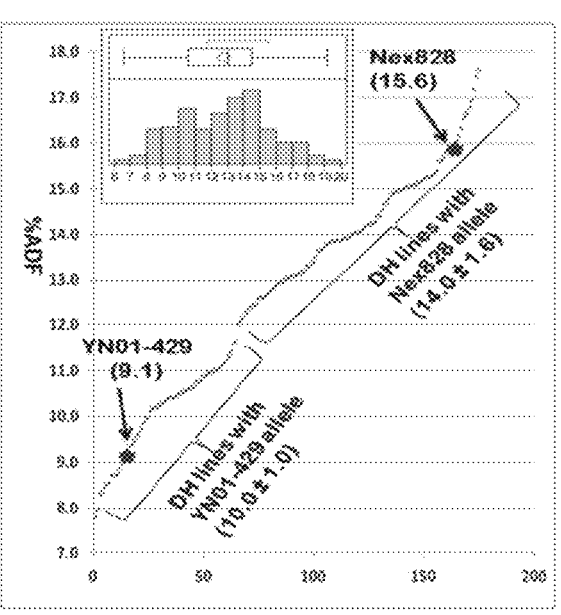
Figure 2:
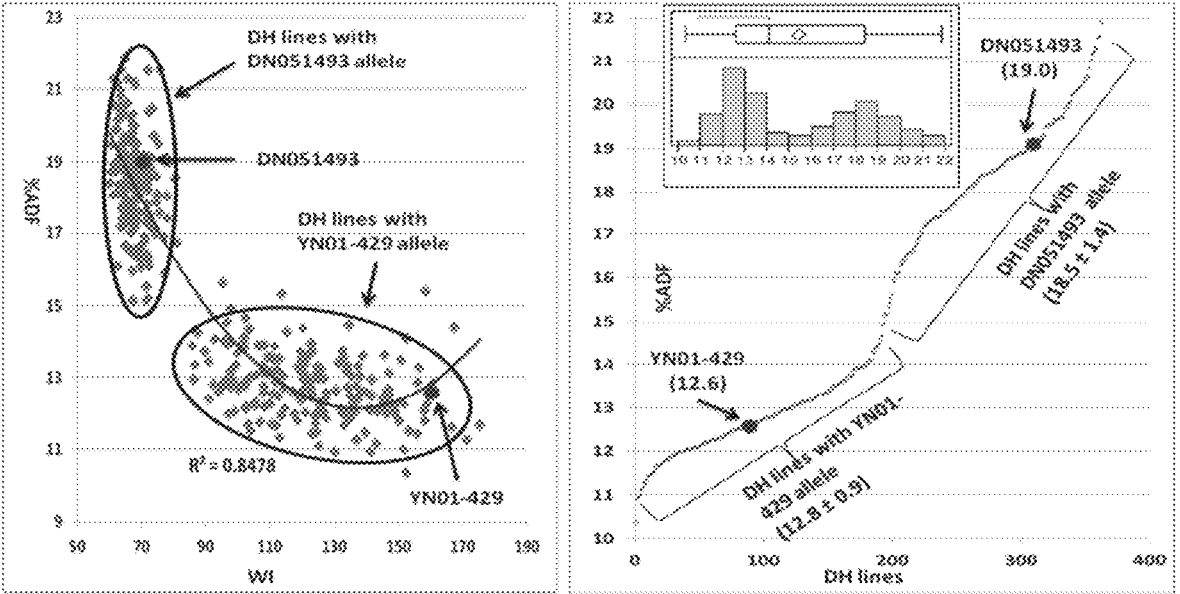
FIG. 2 shows the distribution of White Index (WI) and % ADF in DN051493 x YN01-429 (YDN) DH lines. The left figure shows White Index (WI) of seed coat color plotted against % of ADF canola seed. The right figure shows the distribution of % ADF among DH lines. The number in bracket indicated % of ADF in canola seed.
Figure 7:
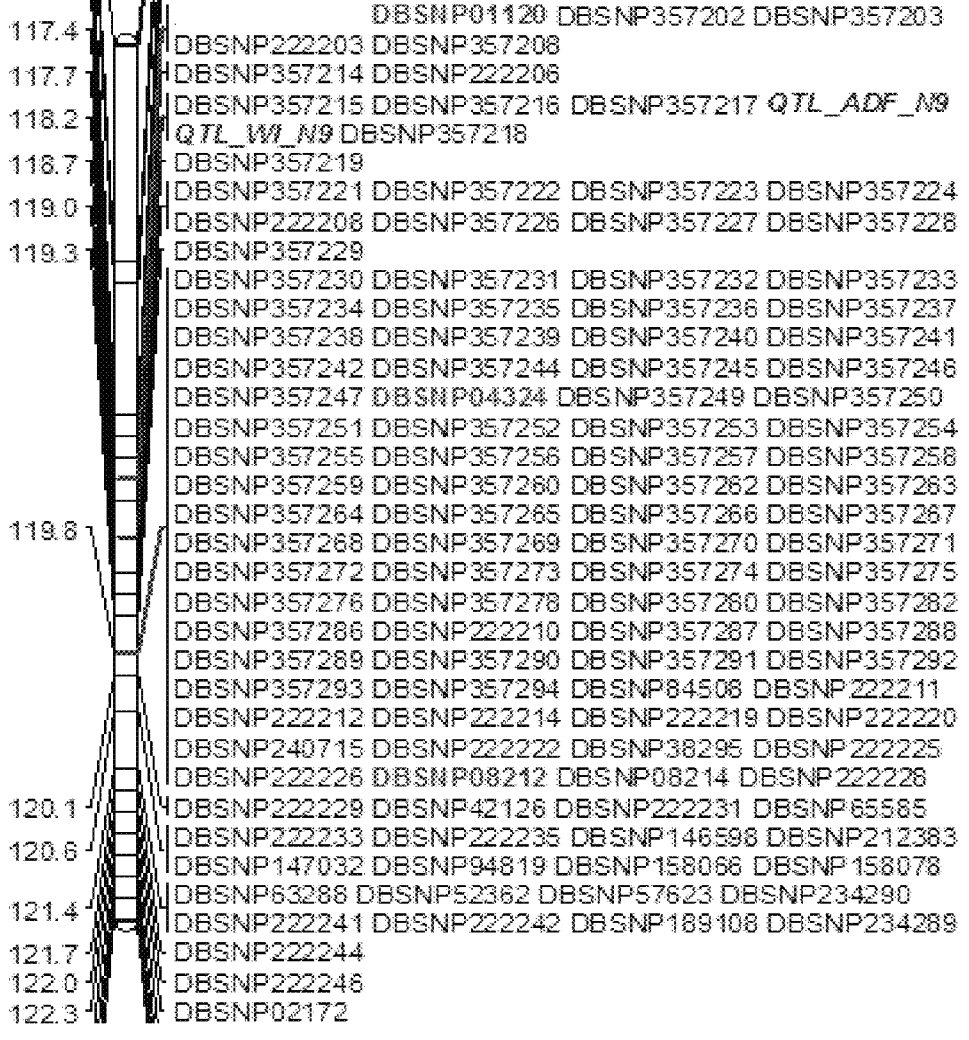
FIG. 7 shows a Map of the major ADF QTL interval on N09, constructed with the YDN DH population. Within the 4.9 cM QTL interval, 111 SNP markers were identified, including the flanking markers DBSNP01120 and DBSNP02172. The ADF_9 and WI_9 loci are also mapped within the interval.

High correlation was also observed between the seed coat color traits WI and L ($R^2$=0.81-0.99) and between seed coat color traits and ADF content ($R^2$=0.66-0.85) in both populations (FIGS. 1 and 2). Because of the large effect of the major QTL (R2=59.2%-74.7%) on N09, and bi-modal distributions of fiber content and seed coat color traits in DH lines (FIGS. 1 and 2), quantitative fiber content and seed coat color traits can be treated as qualitative traits. After conversion of the quantitative traits of ADF and WI into qualitative traits, the ADF (ADF_09) and WI (WI_09) were mapped to the same genomic region where the major QTL were located on N09 in both YSC and YDN populations. FIG. 7 shows the map location of major ADF and WI QTL, ADF_09 and WI_09 on the consensus map of N09 constructed with YSC, YDN and TN populations and 323 SNP markers.

Somers et al. (2001) and Rakow et al. (2011) indicated that the YSC line from AAFC delivers consistently low fiber content across multiple environments, and low lignin content is always associated with the yellow seed color. The YSC genetic map was constructed with 174 DH and 2,982 polymorphic SNP markers, a total length of 2,515.8 cM and an average length of 0.80 cM/marker. The YDN population was constructed with 397 DH lines and 2,972 SNP markers, a total length of 2,189 cM and an average length of 0.74 cM/marker. The TN genetic map was constructed with 181 DH lines and 2,716 polymorphic SNP markers, a total length of 1905.7 cM and an average length of 0.70 cM/marker. In embodiments, the disclosure describes a consensus map of 5,500 SNP markers with an average of 0.47 cM constructed with the YDN, YSC and TN populations (FIG. 7).

Figures 3A, 3B:
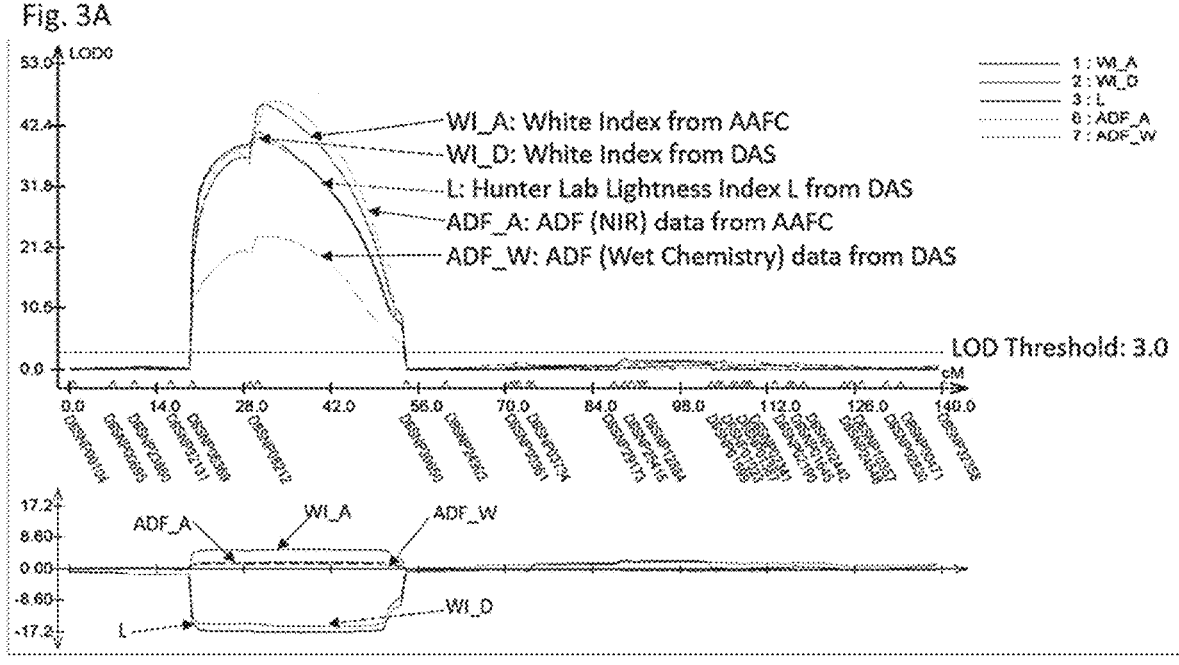
FIG. 3A shows the location (X-axis) and significance (LOD score on Y-axis) of the QTL identified on N09.
FIG. 3B shows the additive effect of the QTL identified on N09.
Figures 4A, 4B:
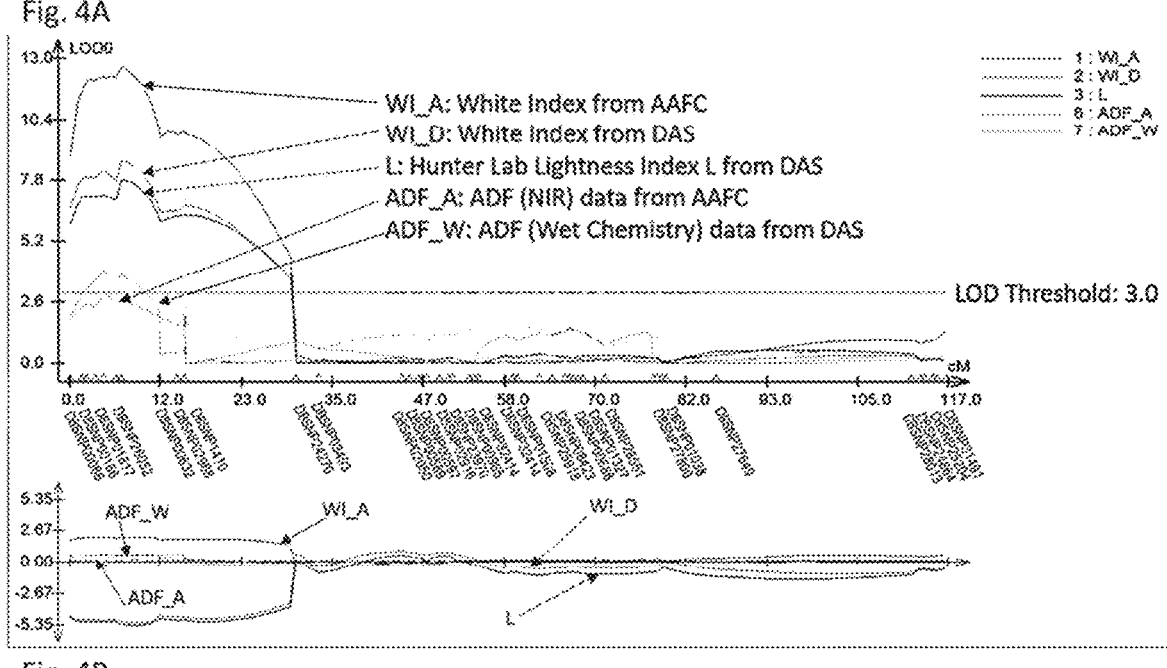
FIG. 4A shows the location (X-axis) and significance (LOD score on Y-axis) of the QTL identified on N11.
FIG. 4B shows the additive effect of the QTL identified on N09.
Figures 5A, 5B:
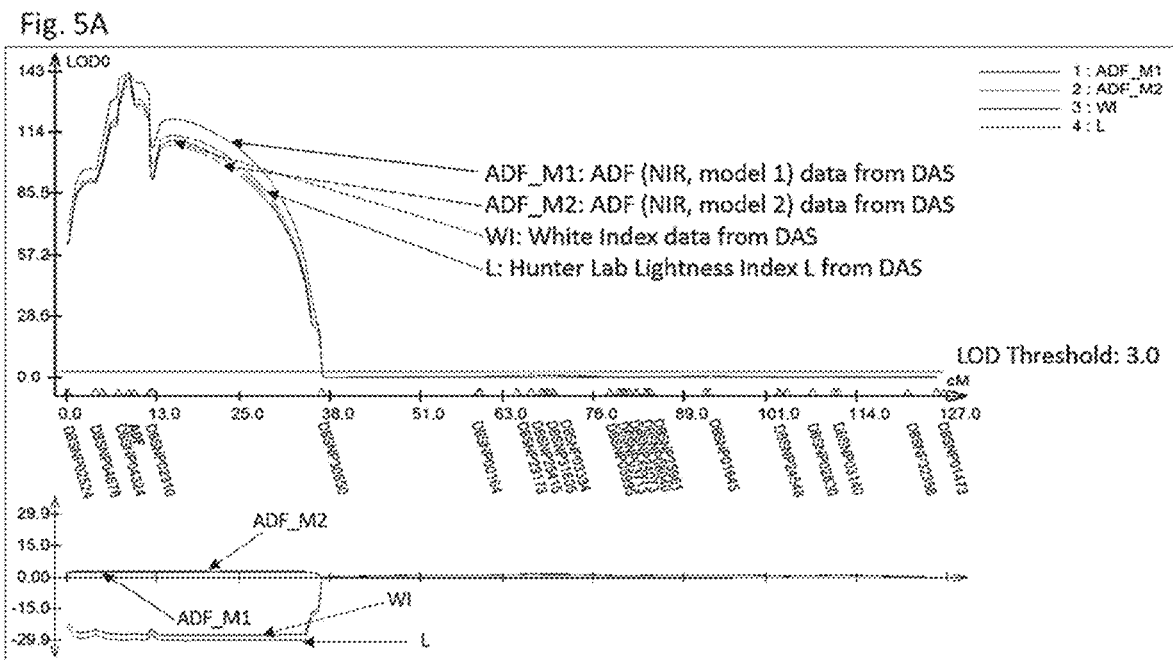
FIG. 5A shows the location (X-axis) and significance (LOD score on Y-axis) of the QTL identified on N09.
FIG. 5B shows the additive effect of the QTL identified on N09.
Figures 6A, 6B:
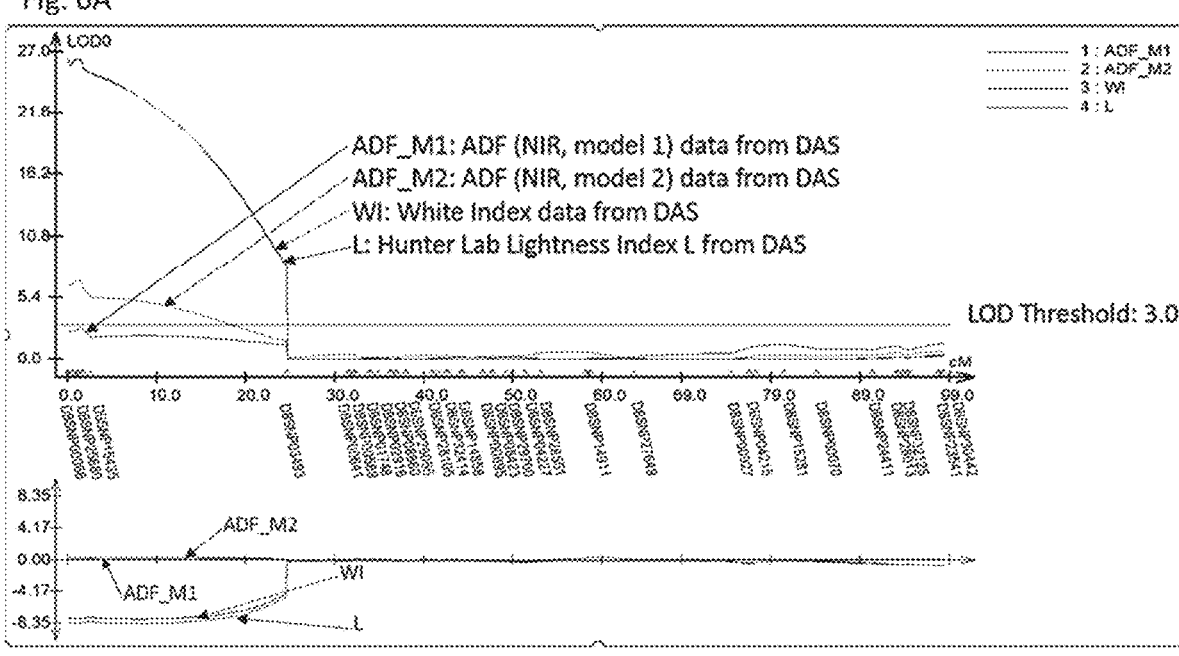
FIG. 6A shows the location (X-axis) and significance (LOD score on Y-axis) of the QTL identified on N11.
FIG. 6B shows the additive effect of the QTL identified on N11.

YSC and YDN populations segregated for fiber content and seed coat color traits and were used for QTL mapping, which further confirmed that seed coat color traits and fiber content traits were highly correlated (FIGS. 3-6). QTL mapping indicated that a major QTL was identified on linkage group (LG) N09 and a minor QTL was identified on LG N11 for all the seed coat color traits (WI and L) and ADF content in both populations (FIGS. 4-6).

In the YSC population, the major QTL identified on N09 explained 71.5% of ADF variance, and coincided with major QTL which explained 59.2% of WI and 60.8% of Lightness Index (L) variance at LOD scores ranged from 40 to 47 (FIG. 3). The minor QTL identified on N11 explained 2.4% of ADF variance, and coincided with the minor QTL which respectively explained 7.2% of WI and 6.3% of Lightness Index (L) variance at LOD scores ranged from 5 to 9 in Nex828 x YN01-429 population (FIG. 4).

QTL analysis of YDN population further confirmed the results from YSC population. The major QTL identified on N09 explained 73.4% of ADF variance and coincided with the major QTL which respectively explained 74.0% of WI and 74.7% of Lightness Index (L) variance at LOD score 143 (FIG. 5). The minor QTL identified on N11 explained 1.4% of ADF variance, and coincided with the minor QTL which respectively explained 5.9% of WI and 5.7% of Lightness Index (L) variance at LOD scores ranged from 3 to 32 (FIG. 6). The results were in accordance with Somers et al. (2001) results, which indicated that a major gene explained 72.3% of the variation in seed color, as well as two additional genes that appeared to be additive and explained 21.5% of the color variation. Since seed coat color QTL (WI and L) perfectly coincided with QTL for fiber content and explained the almost the same percentage of phenotypic variance (R2=77.4%) as QTL for ADF content in both YN01-429 derived DH populations, seed coat color indexes (WI and L) were good indicators for the fiber content in canola seed if YSC line YN01-429 or its lineage is used as a low ADF content source in breeding programs.

II. SNP Markers and QTL Underlying Low Fiber Content and YSC Traits from YN01-429

In some embodiments, the disclosure describes a major QTL which explains 59.2-74.7% of the phenotypic variance of fiber content and seed coat color traits in two dihaploid (DH) plant populations. In particular embodiments, a minor QTL has been found to explain 1.4-7.2% of the phenotypic variance of these traits in two dihaploid plant populations. High correlation is disclosed between seed coat color traits (WI and L) and ADF content in both populations.

In an alternative embodiment, a set of high throughput markers closely linked to fiber content and seed coat color traits from YSC line YN01-419. In other embodiments, nucleic acid sequences linked to QTL's are associated with desirable nutritional traits. The sequence can be derived from yellow-seeded coat (YSC) line YN01-429 or its lineage. Particular embodiments related to a set of 18 SNP markers that lie within 0.0-4.9 cM of the major ADF and seed color (WI) QTL identified in Nex828 x YN01-429 (YSC) and DN051493 x YN01-429 (YDN) DH populations.

In a particular embodiment, the SNP markers include those markers identified as DBSNP357222 through DBSNP2222111 in FIG. 7, which flanked by DSNP01120 and DSNP02172. In another embodiment, the SNP markers include DBSNP357223, DBSNP357224, DBSNP357226, DBSNP357227, DBSNP357228, DBSNP357230, DBSNP357231, DBSNP357233, DBSNP357234, DBSNP357244, DBSNP357247, DBSNP357250, DBSNP357252, DBSNP357253, DBSNP357254, DBSNP357255, DBSNP357256, DBSNP357257, DBSNP357258, DBSNP357273, DBSNP357287, DBSNP357288, DBSNP357290, DBSNP357291, DBSNP357292, DBSNP357293, and DBSNP357294, as shown in FIG. 7.

III. Marker-Assisted Selection (MAS) of Low Fiber Content and YSC Traits from YN01-429

Certain embodiments related to a method for selecting canola plants or germplasm for a desirable nutritional trait associated with QTL's using marker-assisted selection (MAS). For example, the YSC line YN01-429 may be used. Seed color measurement may be used to replace costly and time-consuming wet chemistry analysis of fiber content. SNP markers disclosed to be within 4.9 cM of the major fiber content and seed coat color QTL on N09 or the minor fiber content and seed coat color QTL on N11 can be used for MAS, and will greatly expedite the breeding of canola lines with low fiber content, one of the most important components of DAS Low Fiber product concept.

Particular embodiments describe a method for using the identified QTL in marker-assisted selection (MAS) of the complex fiber content and seed coat color traits from the YSC line YN01-429 to facilitate breeding in *Brassica* and more efficient selection of desirable nutritional traits. Particular embodiments are directed to marker-assisted selection of canola varieties to increase the nutritive value of canola meal, particularly for feed animals, including monogastric animals and ruminants.

According to certain embodiments, the method may be used to select canola seed or germplasm comprising, on average, at least about 44% crude protein, and not more than about 14% acid detergent fiber as determined by NIR on a dry mass basis. In alternative embodiments, the canola seed or germplasm may further comprise, on average, at least about 49% crude protein content. In other embodiments, the canola seed or germplasm may comprise on average, not more than about 12% acid detergent fiber content. Additionally, the canola seed or germplasm selected by the disclosed method may further comprise the following traits: reduced glucosinolate content, low tannin content, and/or low residual cell wall content.

IV. Abbreviations

ADF acid detergent fiber
AME apparent metabolizable energy
DAS Dow AgroSciences
DH dihaploid
FAME fatty acid/fatty acid methyl esters
NMR nuclear magnetic resonance
NIR near-infrared spectroscopy
QTL quantitative trait locus
RAPD random amplified polymorphic DNA
SNP Single nucleotide polymorphism
RCW residual cell walls

V. Terms

Allotetraploid: As used herein, "allotetraploid" generally refers to a hybrid organism that has a chromosome set that is four times that of a haploid organism.

Canola oil: Canola oil refers to oil extracted from commercial varieties of rapeseed. To produce canola oil, seed is typically graded and blended at grain elevators to produce an acceptably uniform product. The blended seed is then crushed, and the oil is typically extracted with hexane and subsequently refined. The resulting oil may then be sold for use. Oil content is typically measured as a percentage of the whole dried seed, and particular oil contents are characteristic of different varieties of canola. Oil content can be readily and routinely determined using various analytical techniques, for example and without limitation: NMR; NIR; and Soxhlet extraction. The percent composition of total fatty acids is typically determined by extracting a sample of oil from seed, producing methyl esters of fatty acids present in the oil sample, and analyzing the proportions of the various fatty acids in the sample using gas chromatography. The fatty acid composition may also be a distinguishing characteristic of particular varieties.

Elite line: As used herein, the term "elite line" means any line that has resulted from breeding and selection for superior agronomic performance. An elite plant is any plant from an elite line.

Enhanced canola meal: As used herein, the term "enhanced canola meal" means canola meal, produced from canola seeds, which has decreased fiber content, and may have increased protein and true metabolizable energy content, as well as reduced anti-nutritional factors such as glucosinolates, tannins, phytic acid, sinapine and erucic acid. Meal with some or all of these characteristics could allow increasing inclusion rates in the diet of animal species especially in monogastric animals.

Plant line: As used herein, a "line" refers to a group of plants that display little genetic variation (e.g., no genetic variation) between individuals for at least one trait. Inbred lines may be created by several generations of self-pollination and selection or, alternatively, by vegetative propagation from a single parent using tissue or cell culture techniques. As used herein, the terms "cultivar," "variety," and "type" are synonymous, and these terms refer to a line that is used for commercial production.

Plant material: As used herein, the term "plant material" refers to any processed or unprocessed material derived, in whole or in part, from a plant. For example and without limitation, a plant material may be a plant part, a seed, a fruit, a leaf, a root, a plant tissue, a plant tissue culture, a plant explant, or a plant cell.

Quantitative trait: As used herein, a "quantitative trait" may refer to a trait or phenotype that is expressed in varying degrees, along a generally continuous gradient and is frequently linked to two or more genes and is affected by environment.

Quantitative trait locus: As used herein, a "quantitative trait locus" refers to a segment or region of DNA containing or linked to a gene or genes underlying a quantitative trait.

Seed color: In some embodiments, this disclosure refers to canola varieties (e.g., inbred canola lines and hybrids) characterized by seed color. Canola seed color rating or "seed color" is generally scored on a 1-5 scale, based on seeds obtained from healthy plants at or near complete seed maturity. "1" signifies a good yellow color. "2" signifies mainly yellow with some brown. "3" indicates a mixture of brown and yellow. "4" and "5" signify brown and black, respectively. Whiteness index (WI) scores also may be used to describe canola varieties. For example, yellow-seeded lines YN97-262 and 9592 have whiteness index scores of −34.6 and −33.2, respectively, and seed color scores of 1. Dark-seeded lines, Nex 715 and Nex 705, have whiteness index scores of −0.2 and −4.4, respectively, and seed color scores of 4. Dark-seeded lines 46A65 and Q2 have whiteness index scores of 0.3 and −3.9, respectively, and seed color scores of 5. Color of particular seeds may also be described in terms of a percentage, or other ratio, as compared to any of these lines.

Stability: As used herein, the term "stability," or "stable," refers to a given plant component that is maintained at substantially the same level through multiple generations. For example, a stable component may be maintained for at least three generations at substantially the same level. In this context, the term "substantially the same" may refer in some embodiments to a component maintained to within 25% between two different generations; within 20%; within 15%; within 10%; within 5%; within 3%; within 2%; and/or within 1%, as well as a component that is maintained perfectly between two different generations. In some embodiments, a stable plant component may be, for example and without limitation, an oil component; a protein component; a fiber component; a pigment component; a glucosinolate component; and a lignin component. The stability of a component may be affected by one or more environment factors. For example, the stability of an oil component may be affected by, for example and without limitation: temperature; location; stress; and the time of planting. Subsequent generations of a plant having a stable component under field conditions will be expected to produce the plant component in a similar manner, for example, as set forth above.

Trait or phenotype: The terms "trait" and "phenotype" are used interchangeably herein. For the purposes of the present disclosure, the traits of particular interest are low fiber content and seed coat color. Some canola varieties exhibit a yellow seed coat, while further varieties exhibit a dark (e.g., black, dark, and mottled) seed coat.

A "variety" or "cultivar" is a plant line that is used for commercial production which is distinct, stable and uniform in its characteristics when propagated.

Unless indicated otherwise, the terms "a" and "an" as used herein refer to at least one.

All references, including publications, patents, and patent applications, cited herein are hereby incorporated by reference to the extent they are not inconsistent with the explicit details of this disclosure, and are so incorporated to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

EXAMPLES

The following Examples are provided to illustrate certain particular features and/or aspects. These Examples should not be construed to limit the disclosure to the particular features or aspects described.

Example 1: Plant Material and DNA Extraction

For fine mapping and validation of low fiber content and seed coat color traits from yellow seed coat (YSC) line YN01-429, two dihaploid (DH) populations, YSC and YDN, were developed from crosses between spring canola lines in 2007 and 2010, respectively. The 176 DH lines of YSC population were developed from a cross between the Agriculture and Agri-Food Canada (AAFC) yellow seeded, low fiber line YN01-429 and the DAS Nexera black seeded, high fiber variety Nex828. The 399 DH lines of the YDN population were developed from a cross between YN01-429 and DAS Nexera black seeded, high fiber variety DN051493. The DH population, TN, was derived from a cross between the European winter cultivar Tapidor and the Chinese semi-winter cultivar Ningyou7. This population was a reference mapping population widely used for trait mapping and genomics studies by the international canola research community (Shi et al. 2009), and was not segregating for fiber content and seed coat color traits. It was used for consensus map construction along with the YSC and YDN populations to identify more Single Nucleotide Polymorphic (SNP) markers tightly linked to the fiber content and seed coat color traits.

Genomic DNA for the populations was extracted from 8 leaf punches per sample using the DAS Biocel extraction method (Bohl et al. 2009). DNA samples were quantified with Quant-iT™ PicoGreen® Quantification Kit (Invitrogen, Carlsbad, CA) using the manufacturer's instructions or with the Nanodrop 8000 Spectrophotometer (Thermo Scientific, Waltham, MA) per manufacturer's instructions.

Example 2: Phenotypic Data

The 176 DH lines from the YSC population were grown along with the two parents as checks in paired row plots at the AAFC Saskatoon research farm and the DAS Rosthern research farm at Canada in 2007 for phenotyping. Seed samples from all established plots were collected from both locations and analyzed by AAFC using Near Infrared Spectroscopy (NIR) for Acid Detergent Fiber (ADF) and seed coat color White Index (WI). The population was also analyzed for ADF using the AOAC reference method (AOAC Official Method 973.18) in 2007 and for seed coat color White Index and Hunter Lab Lightness Index (L) in 2011.

The YDN population was grown along with the two parents as checks in paired row plots at Pike Lake and Cudworth, Canada in 2011 for phenotyping. Seed samples from 361 DH lines were analyzed for ADF using two NIR models and for seed coat color White Index and the HunterLab Lightness Index in 2011.

Significant differences were observed between the two mapping parents for fiber content and seed coat color for both populations, as illustrated in Table 1. Distributions of fiber content in DH lines revealed bi-modal distributions skewed towards the higher fiber range in both populations (FIGS. 1 and 2). High correlation was observed between the seed coat color traits WI and L ($R^2=0.81$-$0.99$) and between seed coat color traits and fiber content traits ($R^2=0.66$-$0.85$) in both populations (FIGS. 1 and 2).

TABLE 1

The % ADF and seed coat color data, WI and L of the parents and DH lines in YSC and YDN populations.

| | YSC population | | | | YDN population | | | |
|---|---|---|---|---|---|---|---|---|
| Trait | Nex828 | YN01-429 | DH lines with Nex828 alleles | DH lines with YN01-429 alleles | DN051493 | YN01-429 | DH lines with DN051493 alleles | DH lines with YN01-429 alleles |
| % ADF | 15.6% | 9.1% | 14.0 ± 1.6% | 10.0 ± 1.0% | 19.0% | 12.6% | 18.5 ± 1.4% | 12.8 ± 0.9% |
| WI | 68.0 | 145.6 | 67.1 ± 4.2 | 100.4 ± 19.2 | 67.9 | 159.3 | 68.0 ± 5.0 | 123.5 ± 19.6 |
| L | 74.4 | 157.7 | 73.1 ± 5.0 | 109.9 ± 20.8 | 74.4 | 172.1 | 74.1 ± 5.9 | 134.8 ± 20.8 |

Example 3: Genotypic Data

The three DH populations, YSC, YDN, and TN, were genotyped with 12,000 SNP markers developed at DAS on two Illumina Infinium chips on the BeadStation 500 G per manufacturer's protocol (Illumina, San Diego, CA). Genotypic data was analyzed using the GenomeStudio Genotyping Analysis Module v1.8.4 (Illumina, San Diego, CA), which converts fluorescent signals for each SNP into A and B signals whose values reflect the relative abundance of arbitrarily assigned A and B alleles. Signal is converted into polar coordinates, using the Manhattan distance metric for the intensity R, and with Theta∈[0,1] representing angle ∈[0,90] degrees. Each marker is clustered in Cartesian coordinates, and the genotypes {AA, AB, BB} are assigned to samples in clusters close to Theta={0, 12, 1}.

Example 4: Linkage Map and Consensus Map Construction

The individual maps of the YSC, YDN and TN populations were constructed with MAPMAKER/EXP 3.0 (Lander et al. 1987; Lincoln et al. 1992) at LOD score 10.0 and Haldane's mapping function, and the consensus map was constructed with Phenomap Enterprise 3.0 (GeneFlow Inc., Centreville, VA).

The YSC genetic map was constructed with 176 DH lines and 2,982 polymorphic SNP markers, and had a total length of 2,515.8 cM and an average length of 0.80 cM/marker. The YDN genetic map was constructed with 399 DH lines and 2,972 SNP markers, and had a total length of 2,189 cM and an average of 0.74 cM/marker. The TN genetic map was constructed with 181 DH lines and 2,716 polymorphic SNP markers, and had a total length of 1905.7 CM and an average of 0.70 cM/marker. A consensus map of 5,500 SNP markers was constructed with the YDN, YSC and TN populations.

Example 5: QTL Mapping

The Composite Interval Mapping (CIM), as implemented in QTL Cartographer V2.5 (Wang et al. 2011), was used for QTL mapping. A LOD score of 3.0 was used as threshold to identify genomic regions significantly affecting the seed coat color and fiber content traits.

Table 2 shows the details of the QTLs identified for seed coat color and fiber content. Results indicated that a major QTL was identified on linkage group (LG) N09 and a minor QTL was identified on N11 for the seed coat color traits, WI and L, and fiber content trait ADF, in both YSC and YDN populations. In the YSC population, the major QTL identified for ADF on N09 coincided with a major QTL for WI and L at LOD scores ranging from 40 to 47. The minor QTL identified for ADF on N11 coincided with a minor QTL for WI and L at LOD scores ranging from 3 to 9 in the YSC population. QTL analysis of the YDN population further confirmed the results from the YSC population. For the YDN population, the major QTL identified for ADF on N09 coincided with the major QTL for WI and L at LOD scores ranged from 136 to 143. The minor QTL identified for ADF on N11 coincided with the minor QTL for WI and L at LOD scores ranging from 7 to 26.

TABLE 2

The phenotypic variance explained (R2) by significant QTL underlying ADF content and seed coat color traits (WI and L) in YSC and YDN populations with LOD scores ≥ 3.

| Population | Trait | Linkage Group | % of Variance Explained ($R^2$) | LOD |
|---|---|---|---|---|
| YSC | Seed coat color_L | N09 | 60.8 | 41 |
| (n = 176) | Seed coat color_WI | N09 | 59.2 | 40 |
| | Fiber content_ADF | N09 | 71.5 | 47 |
| | Seed coat color_L | N11 | 6.3 | 8 |
| | Seed coat color_WI | N11 | 7.2 | 9 |
| | Fiber content_ADF | N11 | 2.4 | 3 |
| YDN | Seed coat color_L | N09 | 74.7 | 143 |
| (n = 399) | Seed coat color_WI | N09 | 74 | 141 |
| | Fiber content_ADF | N09 | 73.4 | 136 |
| | Seed coat color_L | N11 | 5.7 | 26 |
| | Seed coat color_WI | N11 | 5.9 | 26 |
| | Fiber content_ADF | N11 | 1.4 | 7 |

Example 6: Mapping of ADF and Seed Coat Color as Qualitative Traits

Because of the large effect of the major QTL ($R^2$=59.2%-74.7%) on N09, and the bi-modal distributions of fiber content and seed coat color traits in the DH lines (FIGS. 1 and 2), quantitative fiber content and seed coat color traits can be treated as qualitative traits. Based on their ADF content and seed coat color WI, DH lines of both populations were divided into two groups, one with low fiber/high WI and homozygous YN01-429 alleles and the other group with high fiber/low WI and homozygous Nex828 or DN051493 alleles (FIGS. 1 and 2).

In the YSC population, the DH lines with YN01-429 alleles had an average of 10.0±1.0% of ADF and the DH lines with Nex828 alleles had an average of 14.0±1.6% of ADF in canola seeds (FIG. 1). In the YDN population, the DH lines with YN01-429 alleles had an average of 12.8±0.9% of ADF and the DH lines with DN051493 alleles had an average of 18.5±1.4% of ADF in canola seeds (FIG. 2). After conversion of the quantitative traits of ADF and WI into qualitative traits, the ADF (ADF_09) and WI (WI_09) were mapped to the same genomic region where the major QTL were located on N09 in both the YSC and YDN populations. FIG. 7 shows the map location of the major ADF and WI QTL, ADF_09 and WI_09, on the YDN population map of N09.

Example 7: Fine-Mapping of the Major QTL on N09

The YDN population was later used for fine mapping and validation of the major QTL on N09. A new genetic map of N09 was constructed with 1387 SNPs. Flanking markers DBSNP01120 and DBSNP02172 defined a QTL interval of 4.9 cM, corresponding to 0.46 Mb on the B. napus reference genome, DH12075, which was sequenced at AAFC through an industry consortium. The major QTL has an $R^2$ of 75% on N09. Blind screenings of the markers within the QTL interval with multiple DAS proprietary DH populations from the breeding program confirmed that the concordance between marker-predicated phenotype and actual phenotype was ≥98%. FIG. 3 shows the genetic map of the ADF QTL interval along with the ADF_09 and WI_09 loci.

Within the 4.9 cM QTL interval on N09, 111 SNP markers were identified, including the flanking markers DBSNP01120 and DBSNP02172. Table 3 lists the SNPs, their genetic positions in cM, the YN01-429 allele as well as the physical positions of the SNPs on the *B. napus* reference genome (DH12075).

TABLE 3

| | | | | | | |
|---|---|---|---|---|---|---|
| SNP markers within the 4.9 cM QTL interval for ADF mapped on N09 with the YDN population. | | | | | | |
| SNP_Name | SEQ ID NO: | Map Position (CM) | SNP_Type | SNP_Forward | YN01429 genotype | Physical Pos on Ref Genome (bp) |
| DBSNP01120 | 1 | 117.4 | SNP | [T/G] | GG | N9:35982462 . . . 35983088 |
| DBSNP357202 | 2 | 117.4 | SNP | [C/G] | GG | N9:35982582 . . . 35984072 |
| DBSNP357203 | 3 | 117.4 | SNP | [T/G] | TT | N9:35982826 . . . 35984316 |
| DBSNP222203 | 4 | 117.4 | SNP | [A/C] | AC | N9:35987647 . . . 35987947 |
| DBSNP357208 | 5 | 117.4 | SNP | [T/G] | GG | N9:35994219 . . . 35995219 |
| DBSNP357214 | 6 | 117.7 | SNP | [A/G] | AA | N9:36025967 . . . 36026963 |
| DBSNP222206 | 7 | 117.7 | SNP | [A/G] | AA | N9:36027874 . . . 36028174 |
| DBSNP357215 | 8 | 118.2Q | INDEL | [-/A] | AA | N9:36030593 . . . 36031612 |
| DBSNP357216 | 9 | 118.2Q | SNP | [T/G] | TG | N9:36030597 . . . 36031616 |
| DBSNP357217 | 10 | 118.2Q | INDEL | [+/ATCAC GCACCTG CAAATGT] | ATCACG CACCTG CAAATGT | N9:36030617 . . . 36031636 |
| DBSNP357218 | 11 | 118.2Q | SNP | [A/G] | GG | N9:36030736 . . . 36031756 |
| DBSNP357219 | 12 | 118.7 | SNP | [A/G] | GG | N9:36030916 . . . 36031808 |
| DBSNP357221 | 13 | 119 | SNP | [C/G] | CC | N9:36038430 . . . 36039006 |
| DBSNP357222 | 14 | 119 | SNP | [T/G] | TT | N9:36038430 . . . 36039335 |
| DBSNP357223 | 15 | 119 | SNP | [A/G] | GG | N9:36038516 . . . 36039516 |
| DBSNP357224 | 16 | 119 | SNP | [T/C] | CC | N9:36038712 . . . 36039712 |
| DBSNP222208 | 17 | 119 | SNP | [T/C] | CC | N9:36039152 . . . 36039272 |
| DBSNP357226 | 18 | 119 | SNP | [C/G] | GG | N9:36039465 . . . 36040465 |
| DBSNP357227 | 19 | 119 | SNP | [A/C] | CC | N9:36039710 . . . 36040708 |
| DBSNP357228 | 20 | 119 | SNP | [T/C] | CC | N9:36039738 . . . 36040726 |
| DBSNP357229 | 21 | 119.3 | SNP | [T/G] | GG | N9:36040629 . . . 36041743 |
| DBSNP357230 | 22 | 119.8 | SNP | [T/C] | CC | N9:36041302 . . . 36042269 |
| DBSNP357231 | 23 | 119.8 | SNP | [A/G] | AA | N9:36041326 . . . 36042293 |
| DBSNP357232 | 24 | 119.8 | SNP | [T/C] | CC | N9:36041431 . . . 36042398 |
| DBSNP357233 | 25 | 119.8 | SNP | [T/C] | CC | N9:36041470 . . . 36042437 |
| DBSNP357234 | 26 | 119.8 | SNP | [T/C] | CC | N9:36041587 . . . 36042554 |
| DBSNP357235 | 27 | 119.8 | SNP | [A/T] | AA | N9:36042193 . . . 36043188 |
| DBSNP357236 | 28 | 119.8 | INDEL | [+/TT] | TT | N9:36042318 . . . 36043314 |
| DBSNP357237 | 29 | 119.8 | SNP | [T/C] | TT | N9:36042320 . . . 36043316 |
| DBSNP357238 | 30 | 119.8 | SNP | [A/T] | TT | N9:36042626 . . . 36043621 |
| DBSNP357239 | 31 | 119.8 | SNP | [T/C] | TT | N9:36042629 . . . 36043624 |
| DBSNP357240 | 32 | 119.8 | INDEL | [+/A] | + | N9:36042765 . . . 36043760 |
| DBSNP357241 | 33 | 119.8 | SNP | [A/G] | AG | N9:36043110 . . . 36044110 |
| DBSNP357242 | 34 | 119.8 | INDEL | [−/T] | T | N9:36043117 . . . 36044117 |
| DBSNP357244 | 35 | 119.8 | SNP | [T/C] | TT | N9:36043219 . . . 36044219 |
| DBSNP357245 | 36 | 119.8 | SNP | [T/C] | CC | N9:36043480 . . . 36044475 |
| DBSNP357246 | 37 | 119.8 | SNP | [A/T] | TT | N9:36044691 . . . 36045691 |
| DBSNP357247 | 38 | 119.8 | SNP | [A/T] | TT | N9:36045200 . . . 36046200 |
| DBSNP04324 | 39 | 119.8 | SNP | [T/C] | CC | N9:36046568 . . . 36047839 |
| DBSNP357249 | 40 | 119.8 | SNP | [A/G] | AA | N9:36046761 . . . 36047762 |
| DBSNP357250 | 41 | 119.8 | SNP | [A/G] | AA | N9:36046762 . . . 36047763 |
| DBSNP357251 | 42 | 119.8 | SNP | [A/G] | AA | N9:36046778 . . . 36047779 |
| DBSNP357252 | 43 | 119.8 | SNP | [A/G] | GG | N9:36046868 . . . 36047869 |
| DBSNP357253 | 44 | 119.8 | SNP | [A/G] | GG | N9:36046920 . . . 36047921 |
| DBSNP357254 | 45 | 119.8 | INDEL | [+/T] | + | N9:36047652 . . . 36048534 |
| DBSNP357255 | 46 | 119.8 | SNP | [T/C] | TT | N9:36047710 . . . 36048534 |
| DBSNP357256 | 47 | 119.8 | SNP | [A/G] | GG | N9:36047752 . . . 36048534 |
| DBSNP357257 | 48 | 119.8 | SNP | [T/C] | CC | N9:36047876 . . . 36048534 |
| DBSNP357258 | 49 | 119.8 | SNP | [A/G] | AA | N9:36047941 . . . 36048534 |
| DBSNP357259 | 50 | 119.8 | SNP | [T/C] | TT | N9:36048002 . . . 36048534 |
| DBSNP357260 | 51 | 119.8 | SNP | [C/G] | GG | N9:36048012 . . . 36048534 |
| DBSNP357262 | 52 | 119.8 | INDEL | [+/A] | + | N9:36048530 . . . 36049322 |
| DBSNP357263 | 53 | 119.8 | SNP | [A/T] | TT | N9:36048530 . . . 36049347 |
| DBSNP357264 | 54 | 119.8 | SNP | [A/T] | TT | N9:36048530 . . . 36049442 |
| DBSNP357265 | 55 | 119.8 | SNP | [A/G] | AG | N9:36048530 . . . 36049520 |
| DBSNP357266 | 56 | 119.8 | SNP | [A/G] | AA | N9:36048564 . . . 36049565 |
| DBSNP357267 | 57 | 119.8 | SNP | [C/G] | CG | N9:36048641 . . . 36049642 |
| DBSNP357268 | 58 | 119.8 | SNP | [A/C] | CC | N9:36048645 . . . 36049646 |
| DBSNP357269 | 59 | 119.8 | SNP | [T/C] | TC | N9:36048651 . . . 36049652 |
| DBSNP357270 | 60 | 119.8 | SNP | [C/G] | CC | N9:36048792 . . . 36049793 |
| DBSNP357271 | 61 | 119.8 | SNP | [T/C] | CC | N9:36048794 . . . 36049795 |
| DBSNP357272 | 62 | 119.8 | INDEL | [+/A] | + | N9:36048932 . . . 36049933 |
| DBSNP357273 | 63 | 119.8 | SNP | [A/T] | TT | N9:36048985 . . . 36049986 |
| DBSNP357274 | 64 | 119.8 | SNP | [A/G] | AG | N9:36049082 . . . 36050083 |
| DBSNP357275 | 65 | 119.8 | SNP | [T/C] | TC | N9:36049455 . . . 36050457 |
| DBSNP357276 | 66 | 119.8 | SNP | [A/G] | AA | N9:36049482 . . . 36050484 |

TABLE 3-continued

SNP markers within the 4.9 cM QTL interval
for ADF mapped on N09 with the YDN population.

| SNP_Name | SEQ ID NO: | Map Position (CM) | SNP_Type | SNP_Forward | YN01429 genotype | Physical Pos on Ref Genome (bp) |
|---|---|---|---|---|---|---|
| DBSNP357278 | 67 | 119.8 | SNP | [C/G] | CC | N9:36049554 . . . 36050556 |
| DBSNP357280 | 68 | 119.8 | SNP | [T/G] | TT | N9:36049653 . . . 36050643 |
| DBSNP357282 | 69 | 119.8 | SNP | [T/G] | TT | N9:36049758 . . . 36050643 |
| DBSNP357286 | 70 | 119.8 | SNP | [A/G] | AA | N9:36054018 . . . 36055018 |
| DBSNP222210 | 71 | 119.8 | SNP | [A/G] | AG | N9:36054461 . . . 36054578 |
| DBSNP357287 | 72 | 119.8 | SNP | [A/T] | TT | N9:36054757 . . . 36055757 |
| DBSNP357288 | 73 | 119.8 | SNP | [A/G] | GG | N9:36054789 . . . 36055789 |
| DBSNP357289 | 74 | 119.8 | SNP | [T/C] | CC | N9:36054810 . . . 36055810 |
| DBSNP357290 | 75 | 119.8 | SNP | [A/G] | AA | N9:36054813 . . . 36055813 |
| DBSNP357291 | 76 | 119.8 | SNP | [A/C] | AA | N9:36054956 . . . 36055956 |
| DBSNP357292 | 77 | 119.8 | SNP | [C/G] | CC | N9:36054966 . . . 36055966 |
| DBSNP357293 | 78 | 119.8 | SNP | [T/C] | TT | N9:36054983 . . . 36055983 |
| DBSNP357294 | 79 | 119.8 | SNP | [T/C] | TT | N9:36055008 . . . 36056008 |
| DBSNP84508 | 80 | 119.8 | SNP | [A/C] | AC | N9:36055121 . . . 36055879 |
| DBSNP222211 | 81 | 119.8 | SNP | [A/G] | GG | N9:36060768 . . . 36060968 |
| DBSNP222212 | 82 | 119.8 | SNP | [A/G] | GG | N9:36061805 . . . 36061924 |
| DBSNP222214 | 83 | 119.8 | SNP | [A/G] | AA | N9:36076182 . . . 36076301 |
| DBSNP222219 | 84 | 119.8 | SNP (dominant) | [T/G] | -- | N9:36096659 . . . 36096732 |
| DBSNP222220 | 85 | 119.8 | SNP (dominant) | [A/C] | -- | N9:36096733 . . . 36096814 |
| DBSNP240715 | 86 | 119.8 | SNP | [A/G] | AC | N9:36100799 . . . 36100917 |
| DBSNP222222 | 87 | 119.8 | SNP | [A/G] | GG | N9:36119793 . . . 36119830 |
| DBSNP38295 | 88 | 119.8 | SNP | [A/G] | GG | N9:36132536 . . . 36133536 |
| DBSNP222225 | 89 | 119.8 | SNP | [A/G] | GG | N9:36132936 . . . 36133136 |
| DBSNP222226 | 90 | 119.8 | SNP | [A/G] | AA | N9:36136254 . . . 36136558 |
| DBSNP08212 | 91 | 119.8 | SNP | [A/G] | AA | N9:36143105 . . . 36143329 |
| DBSNP08214 | 92 | 119.8 | SNP | [T/G] | TT | N9:36143105 . . . 36143329 |
| DBSNP222228 | 93 | 119.8 | SNP | [T/C] | CC | N9:36147820 . . . 36147940 |
| DBSNP222229 | 94 | 120.1 | SNP | [A/G] | AA | N9:36156553 . . . 36156673 |
| DBSNP42126 | 95 | 120.1 | SNP | [T/G] | GG | N9:36157370 . . . 36158339 |
| DBSNP222231 | 96 | 120.1 | SNP | [T/C] | TT | N9:36165969 . . . 36166169 |
| DBSNP222233 | 97 | 120.6 | SNP | [A/G] | AA | N9:36175905 . . . 36176121 |
| DBSNP222235 | 98 | 120.6 | SNP | [A/G] | AA | N9:36190213 . . . 36190333 |
| DBSNP146598 | 99 | 120.6 | SNP | [T/C] | TC | N9:36207823 . . . 36208597 |
| DBSNP147032 | 100 | 120.6 | SNP | [A/G] | AG | N9:36212362 . . . 36213110 |
| DBSNP94819 | 101 | 120.6 | SNP | [T/G] | TG | N9:36213988 . . . 36214561 |
| DBSNP158066 | 102 | 120.6 | SNP | [A/T] | TA | N9:36214885 . . . 36215409 |
| DBSNP158078 | 103 | 120.6 | SNP | [T/C] | CC | N9:36214926 . . . 36215606 |
| DBSNP63288 | 104 | 121.4 | SNP | [T/G] | TG | N9:36278558 . . . 36279063 |
| DBSNP52362 | 105 | 121.4 | SNP | [T/C] | + | N9:36279239 . . . 36280186 |
| DBSNP222241 | 106 | 121.4 | SNP | [T/C] | -- | N9:36291810 . . . 36291930 |
| DBSNP222242 | 107 | 121.4 | SNP | [T/C] | TT | N9:36308543 . . . 36308663 |
| DBSNP189108 | 108 | 121.4 | SNP | [T/C] | TC | N9:36308946 . . . 36309355 |
| DBSNP222244 | 109 | 121.7 | SNP | [T/C] | CC | N9:36353147 . . . 36353447 |
| DBSNP222246 | 110 | 122 | SNP | [T/G] | TT | N9:36372163 . . . 36372403 |
| DBSNP02172 | 111 | 122.3 | SNP | [C/G] | CC | N9:36447139 . . . 36448664 |

Within the 4.9 cm ADF QTL interval, flanked by DBSNP01120 and DBSNP02172, a sub-interval was defined in which the markers are most desired for marker assisted selection. Flanking markers DBSNP35722 and DBSNP222211 define a 0.5 cM sub-interval haplotype region unique to the donor YN01-429. The DBSNP35722 and DBSNP222211 flanking markers and the markers within the sub-interval can be used for marker assisted selection to track the QTL on N09 when breeding for enhanced ACM attributes.

What is claimed is:

1. A method of breeding *Brassica napus* plants comprising an N09 chromosomal interval:

crossing a first *Brassica napus* plant with a second *Brassica napus* plant and thereby producing progeny, wherein the first plant comprises an N09 chromosomal represented by the N09 chromosomal interval of *Brassica napus* line YN01-429 or YN-97-262 comprising and flanked by SEQ ID NO:2 and SEQ ID NO:111;

using marker assisted selection to analyze the progeny plants or germplasm thereof for the presence or the absence of the N09 chromosomal interval comprising the plurality of markers selected from the group of SEQ ID NO:2 through SEQ ID NO:111; and selecting one or more progeny plants or germplasm thereof having the N09 chromosomal interval, wherein the one or more selected progeny plants have lower ADF than the second *Brassica napus* plant.

2. The method of claim 1 wherein the plurality of markers are selected from the following: a guanine (G) at position 501 of SEQ ID NO:2, a thymine (T) at position 501 of SEQ ID NO:3, a G at position 501 of SEQ ID NO:5, an adenine (A) at position 501 of SEQ ID NO:6, an A at position 151 of SEQ ID NO:7, an A at position 501 of SEQ ID NO:8, a 19 nucleotide insertion at position 502 of SEQ ID NO:10, a G at position 501 of SEQ ID NO:11, a G at position 501 of SEQ ID NO:12, a cytosine (C) at position 501 of SEQ ID NO:13, a thymine (T) at position 501 of SEQ ID NO:14, a guanine (G) at position 501 of SEQ ID NO:15, a cytosine (C) at position 501 of SEQ ID NO:16, a C at position 61 of SEQ ID NO:17, a G at position 501 of SEQ ID NO:18, a C at position 501 of SEQ ID NO:19, a C at position 501 of SEQ ID NO:20, a G at position 501 of SEQ ID NO:21, a C at position 501 of SEQ ID NO:22, an adenine at position 501 of SEQ ID NO:23, a C at position 501 of SEQ ID NO:24, a C at position 501 of SEQ ID NO:25, a C at position 501 of SEQ ID NO:26, an A at position 501 of SEQ ID NO:27, a TT at position 502 of SEQ ID NO:28, a T at position 501 of SEQ ID NO:29, a T at position 501 of SEQ ID NO:30, a T at position 501 of SEQ ID NO:31, a T at position 502 of SEQ ID NO:32, a T at position 501 of SEQ ID NO:34, a T at position 501 of SEQ ID NO:35, a C at position 501 of SEQ ID NO:36, a T at position 501 of SEQ ID NO:37, a T at position 501 of SEQ ID NO:38, a C at position 536 of SEQ ID NO:39, an A at position 501 of SEQ ID NO:40, an A at position 501 of SEQ ID NO:41, an A at position 501 of SEQ ID NO:42, a G at position 501 of SEQ ID NO:43, a G at position 501 of SEQ ID NO:44, an A at position 502 of SEQ ID NO:45, a T at position 501 of SEQ ID NO:46, a G at position 501 of SEQ ID NO:47, a C at position 501 of SEQ ID NO:48, an A at position 501 of SEQ ID NO:49, a T at position 501 of SEQ ID NO:50, a G at position 501 of SEQ ID NO:51, a C at position 502 of SEQ ID NO:52, a T at position 501 of SEQ ID NO:53, a T at position 501 of SEQ ID NO:54, an A at position 501 of SEQ ID NO:56, a C at position 501 of SEQ ID NO:58, a C at position 501 of SEQ ID NO:60, a C at position 501 of SEQ ID NO:61, a C at position 502 of SEQ ID NO:62, a T at position 501 of SEQ ID NO:63, an A at position 501 of SEQ ID NO:66, a C at position 501 of SEQ ID NO:67, a T at position 501 of SEQ ID NO:68, a T at position 501 of SEQ ID NO:69, an A at position 501 of SEQ ID NO:70, a T at position 501 of SEQ ID NO:72, a G at position 501 of SEQ ID NO:73, a C at position 501 of SEQ ID NO:74, an A at position 501 of SEQ ID NO:75, an A at position 501 of SEQ ID NO:76, a C at position 501 of SEQ ID NO:77, a T at position 501 of SEQ ID NO:78, a T at position 501 of SEQ ID NO:79, or a G at position 101 of SEQ ID NO:81, a G at position 61 of SEQ ID NO:82, an A at position 61 of SEQ ID NO:83, a G at position 61 of SEQ ID NO:87, a G at position 501 of SEQ ID NO:88, a G at position 101 of SEQ ID NO:89, an A at position 151 of SEQ ID NO:90, an A at position 153 of SEQ ID NO:91, a T at position 48 of SEQ ID NO:92, a C at position 61 of SEQ ID NO:93, an A at position 61 of SEQ ID NO:94, a G at position 501 of SEQ ID NO:95, a T at position 101 of SEQ ID NO:96, an A at position 151 of SEQ ID NO:97, an A at position 61 of SEQ ID NO:98, a C at position 328 of SEQ ID NO:103, a T at position 61 of SEQ ID NO:107, a C at position 151 of SEQ ID NO:109, a T at position 151 of SEQ ID NO:110, and a C at position 848 of SEQ ID NO:111.

3. The method of claim 1 wherein the plurality of markers are selected from the following: a guanine (G) at position 501 of SEQ ID NO:15, a cytosine (C) at position 501 of SEQ ID NO:16, a G at position 501 of SEQ ID NO:18, a C at position 501 of SEQ ID NO:19, a C at position 501 of SEQ ID NO:20, a C at position 501 of SEQ ID NO:22, an adenine at position 501 of SEQ ID NO:23, a C at position 501 of SEQ ID NO:25, a C at position 501 of SEQ ID NO:26, a T at position 501 of SEQ ID NO:35, a T at position 501 of SEQ ID NO:38, an A at position 501 of SEQ ID NO:41, a G at position 501 of SEQ ID NO:43, a G at position 501 of SEQ ID NO:44, an A at position 502 of SEQ ID NO:45, a T at position 501 of SEQ ID NO:46, a G at position 501 of SEQ ID NO:47, a C at position 501 of SEQ ID NO:48, an A at position 501 of SEQ ID NO:49, a T at position 501 of SEQ ID NO:63, a T at position 501 of SEQ ID NO:72, a G at position 501 of SEQ ID NO:73, an A at position 501 of SEQ ID NO:75, an A at position 501 of SEQ ID NO:76, a C at position 501 of SEQ ID NO:77, a T at position 501 of SEQ ID NO:78, and a T at position 501 of SEQ ID NO:79.

4. The method of claim 1, further comprising using one or more of the selected progeny plants to make a *Brassica napus* plant line having the N09 chromosomal interval.

5. The method of claim 2, further comprising using one or more of the selected progeny plants to make a *Brassica napus* plant line having the N09 chromosomal interval.

6. The method of claim 3, further comprising using one or more of the selected progeny plants to make a *Brassica napus* plant line having the N09 chromosomal interval.

7. The method of claim 4, further comprising planting a field with the *Brassica napus* plant line having the N09 chromosomal interval, growing *Brassica napus* plants having the N09 chromosomal interval plants and collecting seed or grain from the grown plants.

8. The method of claim 5, further comprising planting a field with the *Brassica napus* plant line having the N09 chromosomal interval, growing *Brassica napus* plants having the N09 chromosomal interval plants and collecting seed or grain from the grown plants.

9. The method of claim 6, further comprising planting a field with the *Brassica napus* plant line having the N09 chromosomal interval, growing *Brassica napus* plants having the N09 chromosomal interval plants and collecting seed or grain from the grown plants.

10. The method of claim 7, further comprising producing meal from the collected seed or grain.

11. The method of claim 8, further comprising producing meal from the collected seed or grain.

12. The method of claim 9, further comprising producing meal from the collected seed or grain.

13. The method of claim 1 further comprising, using one or more of the selected progeny plants as a parent line to produce *Brassica napus* seed or grain having the N09 chromosomal interval.

14. The method of claim 2 further comprising, using one or more of the selected progeny plants as a parent line to produce *Brassica napus* seed or grain having the N09 chromosomal interval.

15. The method of claim 3 further comprising, using one or more of the selected progeny plants as a parent line to produce *Brassica napus* seed or grain having the N09 chromosomal interval.

\* \* \* \* \*

SEQUENCE LISTING

```
Sequence total quantity: 111
SEQ ID NO: 1              moltype = DNA  length = 532
FEATURE                   Location/Qualifiers
variation                 295
                          note = where n is a, t, c, or g
variation                 369
                          note = where n is a, t, c, or g
variation                 441
                          note = where n is a, t, c, or g
variation                 452
                          note = where n is a, t, c, or g
variation                 473
```

-continued

```
                           note = where n is a, t, c, or g
source                     1..532
                           mol_type = other DNA
                           organism = Brassica napus
SEQUENCE: 1
gaatttccgg gtcgacatca tcgaggccgg gttccccgcc gcgtccaaag acgacttcga    60
ggcggtcaag accatttccg aaaccgtcgg aaacgccgtc gacgagaacg gttacgtccc   120
cgtcatctgc ggtctctcga ggtgcaacga gagagatatc cagacggctt gggaggctgt   180
gagatacgcc aaaaggccta ggatccatac gttcatcgcc gcgagtgata ttcacttgga   240
gtataagctc aagaagagta aacaagaagt catcgagatc gckaggagca tggtntaggt   300
tcgctaggag cttggggtgt gatgacgtgg agtttagtcc tgaagatgca ggaaggtcgg   360
agagagagnt ttttgtatga gattcttgga gaagtgataa aagctggagc gacgacactt   420
aatattcctg atactgttgg ntatcacttt gncctagtga gtttggtcag ttngattgct   480
gatataaagg ctaataccc tgggattgag aacgttgtca tctcgactca tt            532

SEQ ID NO: 2              moltype = DNA    length = 1001
FEATURE                   Location/Qualifiers
source                    1..1001
                          mol_type = other DNA
                          organism = Brassica napus
SEQUENCE: 2
ctccagcttt tatcacttct ccaagaatct catacaaaaa ctctctctcc gacctgttaa    60
acaaattaaa ataaatataa acagttacag agaaagtgaa agcttggtaa tcaagattag   120
aactaattaa aataaataaa agataattaa accccccacc ttcctgcatc ttcaggacta   180
aactccacgt catcacaccc caagctccta gcgaacctaa ccatgctcct cgcgatctcg   240
atgacttctt gtttactctt cttgagctta tactccaagt gaatatcact cgtggcgatg   300
aacgtatgga tcctaggcct tttggcgtat ctcacagcct cccaagccgt ctggatatct   360
ctctcgttgc acctcgagag accgcagatg acggggacgt aaccgttctc gtcgacggcg   420
tttccgacgg tttcggaaat ggtcttgacc gcctcgaagt cgtctttgga cgcggcgggg   480
aacccggcct cgatgatgtc sacgccgagc ttcgcgagct gccgcgcgat cgtcgagcttc   540
tccttggagg tgagggtggc gccgggggac tgctcgccgt cgcggagcgt ggtgtcgaag   600
atgcggacgt agttggggtc ggaaatgcgg ttggggatgt agtccgggcg gcggcggcgg   660
aggggggtggg gagggagagg gggcggtgga tctgagatgg agcaggagag gcggaggagg   720
gcggaggagg agcggcggcg gtggtgggat ggtgggaaac ggaaggagag tggtgtggtg   780
attgttgtgg agaaggtggg gagagaaggt gttgttgttg atgatgagag tgaagggttt   840
ctgagaaggg aagacgccat tggagacgat tgtgagaaga atggtaaacc taaagagaga   900
gagagatgaa ggtttgaacg tggcggcggc agctacttgg ttaagctcta tctgttcgtt   960
cgtgtcactc ttctctttat ttgacaaaaa caaatctttt t                      1001

SEQ ID NO: 3              moltype = DNA    length = 1001
FEATURE                   Location/Qualifiers
source                    1..1001
                          mol_type = other DNA
                          organism = Brassica napus
SEQUENCE: 3
cttcttgttt actcttcttg agcttatact ccaagtgaat atcactcgtg gcgatgaacg    60
tatggatcct aggccttttg gcgtatctca cagcctccca agcctctgg atatctctct   120
cgttgcacct cgagagaccg cagatgacgg gacgtaacc gttctcgtcg acggcgtttc   180
cgacggtttc ggaaatggtc ttgaccgcct cgaagtcgtc tttggacgcg gcggggaacc   240
cggcctcgat gatgtcgacg ccgagcttcg cgagctgccg cgcgatgtcg agcttctcct   300
tggaggtgag ggtggcgccg ggggactgct cgccgtcgcc gtcgggtggtg tcgaagatg   360
ggacgtagtt ggggtcggaa atgcggttgg ggatgtagtc cgggcggcgg cggcggaggg   420
ggtggggagg gagagggggc ggtggatctg agatggagca ggagaggcgg agggaggcgg   480
aggaggagcg gcggcggtgg kgggatggtg ggaaacggaa ggagagtggt gtggtgattg   540
ttgtggagaa ggtggggaga gaaggtgttg ttgttgatga tgagagtgaa gggtttctga   600
gaagggaaga cgccattgga gacgattgtg agaagaatgg taaacctaaa gagagagaga   660
gatgaaggtt tgaacgtggc ggcggcagct acttggttaa gctctatctg ttcgttcgtg   720
tcactcttct ctttatttga caaaacaaa tctttttttt tggtcccact tgaatattct   780
ccacttaaaa aaatgagtac gacaactgtg ttatacttta aacggcgtcg ttataggata   840
caatagaaaa agtcgaccgg caacgataag gacgatgagt cgattgaaca gtttagaaag   900
gacgtagaac catgagattc accaataagc attgaacaag aagacatgga gatggaaagt   960
tgttaaaaca tttttttaaat gaacttaaca tgtcacattg t                     1001

SEQ ID NO: 4              moltype = DNA    length = 301
FEATURE                   Location/Qualifiers
source                    1..301
                          mol_type = other DNA
                          organism = Brassica napus
SEQUENCE: 4
caaracattt tcacatatat cacttycatg ctcacytcca ccaaccacaa aaaaatgacg    60
agtactataa agcaagaagg acaaagcata cccaatattt ataaataaat cccaccagct   120
gagtgcatct acatcgcctg agtattaaaa mataaaacaa ggagggccga taagaaggaa   180
gggaacgcaa taacattatc tatgaagata agacttcaga aggcagagag accaagtaag   240
aaaattatgt aggcaagcat tcaagagata caacattacc agtaagctty aggaggataa   300
a                                                                    301

SEQ ID NO: 5              moltype = DNA    length = 1001
FEATURE                   Location/Qualifiers
source                    1..1001
```

```
                          mol_type = other DNA
                          organism = Brassica napus
SEQUENCE: 5
tagcatgccc agtagtagca aaagaagtga gcacctaaca cgaaaaaacg ccaaagtcat      60
gctgctttca caagagcagg tagaaaacaa aagaaaaggg aatatacagg attcttagcc     120
atgaacaatg cctggaactt tgtattttc aaacattagc tctgccgccc tgtcaagcat     180
acaatttgag aacatcagta acacactcaa agatgaacta acataagaca aaagtaaata     240
tctataagca gataaatcag acttctctct atgctgttga gtgtttaaag gaggctcagc     300
tagcagcatg ggctgctcct taggatcaat catcaaacaa ctccttcaga cataaaaaaa     360
catattagag atgacatcaa acaataattt atgagaaaaa actaaagctt tatacagttt     420
acctgaatgc atgttcccat ttttgtttat taaaatattg caaaaataat tgactaaatc     480
ttcatataca aaattttgac kgaaaactgc agctttcatc ttcttcctgg agatttaggt     540
ttatatctcc aattggattg gatttgttct cttgaaggga ttaaaacgaa aaagagggaa     600
aacaaaataa aacgccgttg ccgggggatcg aacccggtc accgcgtga caggcgtgaa     660
tacttaccac tatactacaa cgactcagtt gattaaagat tcaatcaaaa tatactgaaa     720
taaaaaagtt tacgctttga aatgggagac agagctcaac gtacgcactc acgagattct     780
ccagcctcgc aaccaactcc atcagtagcg aagcgaatca aaatttactg aaataaaaaa     840
aaggttacac tttgaaactt actttctaag taattgacaa tacaatatac aaagaaatgg     900
catattaaag tctctttatc gctgtcttaa tcttcttggt tccactcttg ctccattcag     960
ctagtcagct ctcgcccaag gtccgagttg taacggcccg g                       1001

SEQ ID NO: 6              moltype = DNA  length = 1001
FEATURE                   Location/Qualifiers
source                    1..1001
                          mol_type = other DNA
                          organism = Brassica napus
SEQUENCE: 6
ctttgccttt gtcttattat ttgatcttct ttacagctgt gtacgagtca gctaaacatt      60
gctccgttac tcctctccag tattaaatca tgccaggcca gcgcaagatt gttatttgac     120
tacttttcct tccaattacg ttggattact tcttgatttt agttgtgccg caagatctca     180
gatttctaaa ctctgatgca tcaccttctc ctctattggg tttaaaagag ttaattaacc     240
agaagatcaa acatataatt tggatttgtg tttgttttga ccataaatat gttgaaagca     300
gcgtacatgc tactgctttt atctgggaat ggtgttagct taatatgaa agcgatcatg     360
attaggagca accttagacc ctatattttc tacacatggc tgaaggtgat atggtacgag     420
ataatataat tctatttatt tgtagttaat acccttctac atatatttga tgcagaatca     480
tcaaaccgta actctcccgc rgtaatttga aggccatgga aagtaatgtt tcttttactc     540
attgtaactt aatcatatgc tcttttcatg ttcgtcacat ctcacaactt aagaaatcgt     600
tgctacagtt cttcactttt ttccttgtgg taaagtatat ttttactatt ctttcataca     660
tctctttgta gttaaagtag caagagaatt atgagtctga tgtaggatac aagaggtatc     720
cccaaagaag attaactgcc caaaaacaca tgatatctac taaccagcct ctaattacca     780
aagtagtatc tttttctaat gcatatatac attgattttt atctatgtag gtttagtcac     840
tatatatata ggaggtgcga ctagccatca tttgaattta ttcccactct cattgcagtt     900
tgatcactgg tcagaaatgg gacggttaca cgatctgatt ggtagtagag gcacgcgcag     960
gggggggggg ggtacactta cagccatagt cggagaagtc t                       1001

SEQ ID NO: 7              moltype = DNA  length = 301
FEATURE                   Location/Qualifiers
source                    1..301
                          mol_type = other DNA
                          organism = Brassica napus
SEQUENCE: 7
aacatcagca agaaggtaac ttgtacacaa ttgaggttta tgttctggta ctttcggtta      60
ggtttgcact tggtgggcaa gaaattgtgg cttttgacct ggaattagtg tgtcacaata     120
ggcaaacaac ttcagtgacc catcttaaac rtaatgctaa gaagcagtgt atttgtttcg     180
tgctttttgaa gtttgaatat atttttttctt tctcctttttt attaccacaa actactctta     240
tttcctggtt aaaagataaa acgtatggga agcctggtcg tcttactga gtcattatgc     300
a                                                                     301

SEQ ID NO: 8              moltype = DNA  length = 1001
FEATURE                   Location/Qualifiers
variation                 501
                          note = where n is an insertion/deletion [-/A]
source                    1..1001
                          mol_type = other DNA
                          organism = Brassica napus
SEQUENCE: 8
caagttcaat gagaagggaa aaaaataaca gcgttaacac accttaaaag tattatcatc      60
aggaaacatc tcaagagcct gacccctggt cacttcaatc ctttcaaatg gatgtccttc     120
ctaagatgtc agaggaataa actcaaagct ttgtaaaaga agcaaagaaa tatactgtaa     180
ggagaaatac agagatatca aaaataaaga tatgacaaga ctgaataaga agcagtactc     240
gagcatcccc tgcttcagtt tcgggaaagt gttgctcgtt taaacccaga tcgccataga     300
atgcatcgta gaagaaaccc tggatagaca accaaacaaa taatagagag gcaagcacaa     360
agacacagac aaaaagaatc gctgcaggct cttagtctta cctcatctct agctttgcag     420
ggtccaacgc acagcttaca accatactcc tgttcgagaa ccatggtcaa tgtttaccac     480
aatcaagacg agataaaaaa ngtgtttta ccagggcgag aatgtgagcg ctagaacgcc     540
agaaagtatc acggcctttg tcgctgtcaa aactgaaaaa ctcaagcgaa caatcagctt     600
ccagtggcct attcatgtcc cagaggacat cgtttaccga agagatcagc gctgagtttg     660
ccaatcccac agaaatttgc ctcgcgattt ctgctgagt cgtctcccat ctcttccctt     720
ctttcacgtt tccaccatct cgaattgtaa ccctaattaa gttcacagca gaacaacatt     780
```

```
actgtagccc tagctacgca aagtatatat cagcatctat tgtgtttact tgatcggctc    840
gtgtggccga gactgaatct ccgcgagctg cttcgcttgg aactcctcga agagcctgat    900
acgcttctcg atgacggctg agagataagc ctcgtccctg ggatgttcat ccgccatcgt    960
tggacttgga ggagcacaga aagtgacgaa aggccaaggg a                        1001
```

SEQ ID NO: 9             moltype = DNA   length = 1001
FEATURE                  Location/Qualifiers
source                   1..1001
                         mol_type = other DNA
                         organism = Brassica napus
SEQUENCE: 9

```
ttcaatgaga agggaaaaaa ataacagcgt taacacacct taaaagtatt atcatcagga    60
aacatctcaa gagcctgacc cctggtcact tcaatccttt caaatggatg tccttcctaa    120
gatgtcagag gaataaaactc aaagctttgt aaaagaagca aagaaatata ctgtaaggag    180
aaatacagag atatcaaaaa taaagatatg acaagactga ataagaagca gtactcgagc    240
atcccctgct tcagtttcgg gaaagtgttg ctcgtttaaa cccagatcgc catagaatgc    300
atcgtagaag aaaccctgga tagacaacca aacaaataat agagaggcaa gcacaaagac    360
acagacaaaa agaatcgctg caggctctta gtcttacctc atctctagct ttgcagggtc    420
caacgcacag cttacaacca tactcctgtt cgagaaccat ggtcaatgtt taccacaatc    480
aagacgagat aaaaaaagtg kttttaccag ggcgagaatg tgagcgctag aacgccagaa    540
agtatccacg cctttgtcgc tgtcaaaact gaaaaactca agcgaacaat cagcttccag    600
tggcctattc atgtcccaga ggacatcgtt taccgaagag atcagcgctg agtttgccaa    660
tcccacagaa atttgcctcg cgatttctgc tggagtcgtc tcccatctct tcccttcttt    720
cacgtttcca ccatctcgaa ttgtaaccct aattaagttc acagcagaac aacattactg    780
tagccctagc tacgcaaagt atatatcagc atctattgtg tttacttgat cggctcgtgt    840
ggccgagact gaatctccgc gagctgcttc gcttggaac cctcgaagag cctgatacgc    900
ttctcgatga cggctgagag ataagcctcg tccctgggat gttcatccgc catcgttgga    960
cttggaggag cacagaaagt gacgaaaggc caagggatg t                        1001
```

SEQ ID NO: 10            moltype = DNA   length = 1002
FEATURE                  Location/Qualifiers
variation                502
                         note = where n is an insertion/deletion
                         [+/ATCACGCACCTGCAAATGT]
source                   1..1002
                         mol_type = other DNA
                         organism = Brassica napus
SEQUENCE: 10

```
ataacagcgt taacacacct taaaagtatt atcatcagga aacatctcaa gagcctgacc    60
cctggtcact tcaatccttt caaatggatg tccttcctaa gatgtcagag gaataaaactc    120
aaagctttgt aaaagaagca aagaaatata ctgtaaggag aaatacagag atatcaaaaa    180
taaagatatg acaagactga ataagaagca gtactcgagc atcccctgct tcagtttcgg    240
gaaagtgttg ctcgtttaaa cccagatcgc catagaatgc atcgtagaag aaaccctgga    300
tagacaacca aacaaataat agagaggcaa gcacaaagac acagacaaaa agaatcgctg    360
caggctctta gtcttacctc atctctagct ttgcagggtc caacgcacag cttacaacca    420
tactcctgtt cgagaaccat ggtcaatgtt taccacaatc aagacgagat aaaaaaagtg    480
tttttaccag ggcgagaatg tngagcgcta gaacgccaga aagtatcacg gcctttgtcg    540
ctgtcaaaac tgaaaaactc aagcgaacaa tcagcttcca gtggcctatt catgtcccag    600
aggacatcgt ttaccgaaga gatcagcgct gagtttgcca atcccacaga aatttgcctc    660
gcgatttctg ctggagtcgt ctcccatctc ttcccttctt tcacgtttcc accatctcga    720
attgtaaccc taattaagtt cacagcagaa caacattact gtagccctag ctacgcaaag    780
tatatatcag catctattgt gtttacttga tcggctcgtg tggccgagac tgaatctccg    840
cgagctgctt cgcttggaac tcctcgaaga gcctgatacg cttctcgatg acggctgaga    900
gataagcctc gtccctggga tgttcatccg ccatcgttgg acttggagga gcacagaaag    960
tgacgaaagg ccaagggatg atttttttaaa cgacgaatga ga                     1002
```

SEQ ID NO: 11            moltype = DNA   length = 1001
FEATURE                  Location/Qualifiers
source                   1..1001
                         mol_type = other DNA
                         organism = Brassica napus
SEQUENCE: 11

```
caaagctttg taaaagaagc aaagaaatat actgtaagga gaaatacaga gatatcaaaa    60
ataaagatat gacaagactg aataagaagc agtactcgag catcccctgc ttcagtttcg    120
ggaaagtgtt gctcgtttaa acccagatcg ccatagaatg catcgtagaa gaaaccctgg    180
atagacaacc aaacaaataa tagagaggca agcacaaaga cacagacaaa aagaatcgct    240
gcaggctctt agtcttacct catctctagc tttgcagggt ccaacgcaca gcttacaacc    300
atactcctgt tcgagaacca tggtcaatgt ttaccacaat caagacgagat taaaaaaagt    360
gtttttacca gggcgagaat gtgagcgcta gaacgccaga aagtatcacg gcctttgtcg    420
ctgtcaaaac tgaaaaactc aagcgaacaa tcagcttcca gtggcctatt catgtcccag    480
aggacatcgt ttaccgaaga ratcagcgct gagtttgcca atcccacaga aatttgcctc    540
gcgatttctg ctggagtcgt ctcccatctc ttcccttctt tcacgtttcc accatctcga    600
attgtaaccc taattaagtt cacagcagaa caacattact gtagccctag ctacgcaaag    660
tatatatcag catctattgt gtttacttga tcggctcgtg tggccgagac tgaatctccg    720
cgagctgctt cgcttggaac tcctcgaaga gcctgatacg cttctcgatg acggctgaga    780
gataagcctc gtccctggga tgttcatccg ccatcgttgg acttggagga gcacagaaag    840
tgacgaaagg ccaagggatg atttttttaaa cgacgaatga gagcagacgg gacgatttta    900
tgacaccact ttaccaaagt ttttagtatt taagattttt ttcaaaaaaa aaaaaaagaa    960
tttaattaat ttgcctattt tcacagattt aattcctttg c                       1001
```

```
SEQ ID NO: 12              moltype = DNA  length = 1001
FEATURE                    Location/Qualifiers
source                     1..1001
                           mol_type = other DNA
                           organism = Brassica napus
SEQUENCE: 12
atagacaacc aaacaaataa tagagaggca agcacaaaga cacagacaaa aagaatcgct    60
gcaggctctt agtcttacct catctctagc tttgcagggt ccaacgcaca gcttacaacc   120
atactcctgt tcgagaacca tggtcaatgt ttaccacaat caagacgaga taaaaaaagt   180
gtttttacca gggcgagaat gtgagcgcta gaacgccaga aagtatcacg gcctttgtcg   240
ctgtcaaaac tgaaaaactc aagcgaacaa tcagcttcca gtggcctatt catgtcccag   300
aggacatcgt ttaccgaaga gatcagcgct gagtttgcca atcccacaga aatttgcctc   360
gcgatttctg ctggagtcgt ctcccatctc ttcccttctt tcacgtttcc accatctcga   420
attgtaaccc taattaagtt cacagcagaa caacattact gtagccctag ctacgcaaag   480
tatatatcag catctattgt rtttacttga tcggctcgtg tggccgagac tgaatctccg   540
cgagctgctt cgcttggaac tcctcgaaga gcctgatacg cttctcgatg acggctgaga   600
gataagcctc gtccctggga tgttcatccg ccatcgttgg acttggagga gcacagaaag   660
tgacgaaagg ccaagggatg attttttaaa cgacgaatga gagcgacacg gacgatttta   720
tgacaccact ttaccaaagt tttttagtatt taagattttt ttcaaaaaaa aaaaaaagaa   780
tttaattaat ttgcctattt tcacagattt aattcctttg ctactacaga tttgttgttt   840
cttttcttta attctaattc atttacatgt atactagatt cgtttttccgc gctacgcgcg   900
gattacatga ttcaaatttg ttaatttaca aaaaatttca ctacatttac aatattacta   960
attgtttata aaacatttta aaacacaata attttatagt t                      1001

SEQ ID NO: 13              moltype = DNA  length = 1001
FEATURE                    Location/Qualifiers
source                     1..1001
                           mol_type = other DNA
                           organism = Brassica napus
SEQUENCE: 13
gaagattttt cgaaagaatt ttttcagctt tttttttttt tttttttggg gtttatgggg    60
aattcttctt tggtttcatt tgttttatat tttgattttc aggcgtctga atacctgggt   120
tgttggatta agcttgaaag aaaaagtaaa cttgagaaat aagttaactt ctaatcctac   180
tgagttatgg tttaaaggat tagaaaaatat ccgaataaat tatcctaatg aatttaggat   240
taagaaaaag gaaatatgtg ttttctaatg agtttaggaa atttgattta tatataagga   300
gatgcaaggg tgttgcataa cttatgagtt ttgtgattgt gtgagagctt gaggtttttg   360
agtgagtttt cctcaagaga ttaataagag agttattctt attatagagt ttatacaatt   420
cgagattcta tatgggtatg gaatcgctcg tggaactcac cacccagtca ttggcaaatt   480
atctcaaagg caagaatccc stcaccattc gatctttgtg gaaggtggaa ggcgacctca   540
ctgctgagga ggaagctaag gcgttggcga tgggcgtggc gaaattagga cattaagtcc   600
attgatgctc tacaaaatct tatgtgatta ctgaagtctg aagaagtttg tccaagtgtc   660
gtttgtttga agtcaaaaat aaagatgtag caggattatc aagttctgat cattaaaagt   720
cctattataa tttctatgtt tcatcatcac tttgaagttc agttaatcaa aagtacgatt   780
caagaatatt ccagtactgt ttctcgatcc attattacca aaaagtttag ctaattatct   840
tcctggaaac ttcttctgtt ccccccatag agaaagttgt cctgccttta gttccagatt   900
aaataagatg agtatcaagt acccatatgt attttcttcc aaaatataag aacataatat   960
ccaactataa tttaagaaaa aacaaagatt agtggagaac g                      1001

SEQ ID NO: 14              moltype = DNA  length = 1001
FEATURE                    Location/Qualifiers
source                     1..1001
                           mol_type = other DNA
                           organism = Brassica napus
SEQUENCE: 14
tttgtgattg tgtgagagct tgaggttttt gagtgagttt tcctcaagag attaataaga    60
gagttattct tattatagag tttatacaat tcgagattct atatgggtat ggaatcgctc   120
gtggaactca ccacccagtc attggcaaat tatctcaaag gcaagaatcc cctcaccatt   180
cgatctttgt ggaaggtgga aggcgacctc actgctgagg aggaagctaa ggcgttggcg   240
atgggcgtgg cgaaattagg acattaagtc cattgatgct ctacaaaatc ttatgtgatt   300
actgaagtct gaagaagttt gtccaagtgt cgtttgtttg aagtcaaaaa taaagatgta   360
gcaggattat caagttctga tcattaaaag tcctattata atttctatgt ttcatcatca   420
ctttgaagtt cagttaatca aaagtacgat tcaagaatat tccagtactg tttctcgatc   480
cattattacc aaaaagttta kctaattatc ttcctggaaa cttcttctgt tccccccata   540
gagaaagttg tcctgccttt agttccagat taaataagaa gagtatcaag tacccatatg   600
tattttcttc caaaatataa gaacataata tccaactata atttaagaaa aaacaaagat   660
tagtggagaa cgttaaaaaa tactcttata taaaagttta atatatttta tgaatattta   720
aattttagtt tttttttaaa aaaaagtctc aaaatcaatg acagagaggg tgacattaaa   780
ttaattaatc tttctttatt tggcctgaga tgcatgctgc ttataatagt tagttgcttc   840
cagaggaaac acatattcaa acagacaaga ttagctacga cagttgcctg gtaatatttt   900
ttattttatt aggcttcgtt tggaatgatt attataattt ggtatatgat agagagcttg   960
ggctgtgttc tcacattatt caaggtacat tctttctcac t                      1001

SEQ ID NO: 15              moltype = DNA  length = 1001
FEATURE                    Location/Qualifiers
source                     1..1001
                           mol_type = other DNA
                           organism = Brassica napus
SEQUENCE: 15
```

```
gatctttgtg gaaggtggaa ggcgacctca ctgctgagga ggaagctaag gcgttggcga   60
tgggcgtggc gaaattagga cattaagtcc attgatgctc tacaaaatct tatgtgatta  120
ctgaagtctg aagaagtttg tccaagtgtc gtttgtttga agtcaaaaat aaagatgtag  180
caggattatc aagttctgat cattaaaagt cctattataa tttctatgtt tcatcatcac  240
tttgaagttc agttaatcaa aagtacgatt caagaatatt ccagtactgt ttctcgatcc  300
attattacca aaaagtttag ctaattatct tcctggaaac ttcttctgtt cccccccatag  360
agaaagttgt cctgccttta gttccagatt aaataagatg agtatcaagt acccatatgt  420
attttcttcc aaaatataag aacataatat ccaactataa tttaagaaaa aacaaagatt  480
agtggagaac gttaaaaaat rctcttatat aaaagtttaa tatattttat gaatatttaa  540
attttagttt ttttaaaaa aaaagtctca aaatcaatga cagagagggt gacattaaat  600
taattaatct ttctttattt ggcctgagat gcatgctgct tataatagtt agttgcttcc  660
agaggaaaca catattcaaa cagacaagat tagctacgac agttgcctgg taatattttt  720
tattttatta ggcttcgttt ggaatgatta ttataatttg gtatatgata gagagcttgg  780
gctgtgttct cacattattc aaggtacatt ctttctcact ataattttct ttttacgtta  840
aattcaactc aaaaccaatt gctcaagtaa tactaatttc accattaatt ttgcaatatt  900
ttggtagcaa tcgacgagac caattttggg acgaatcggt ttattgatcg tattgcatgg  960
acaccatatt atttttaggta aactttcaac gcaaaaccaa t                     1001

SEQ ID NO: 16            moltype = DNA   length = 1001
FEATURE                  Location/Qualifiers
source                   1..1001
                         mol_type = other DNA
                         organism = Brassica napus
SEQUENCE: 16
tgatcattaa aagtcctatt ataatttcta tgtttcatca tcactttgaa gttcagttaa   60
tcaaaagtac gattcaagaa tattccagta ctgtttctcg atccattatt accaaaaagt  120
ttagctaatt atcttcctgg aaacttcttc tgttcccccc atagagaaag ttgtcctgcc  180
tttagttcca gattaaataa gatgagtatc aagtacccat atgtatttc ttccaaaata  240
taagaacata atatccaact ataatttaag aaaaaacaaa gattagtgga gaacgttaaa  300
aaatactctt atataaaagt ttaatatatt ttatgaaattta gtttttttta  360
aaaaaaaagt ctcaaaatca atgacagaga gggtgacatt aaattaatta atctttcttt  420
atttggcctg agatgcatgc tgcttataat agttagttgc ttccagagga aacacatatt  480
caaacagaca agattagcta ygacagttgc ctggtaatat tttttatttt attaggcttc  540
gtttggaatg attattataa tttggtatat gatagagagc ttgggctgtg ttctcacatt  600
attcaaggta cattctttct cactataatt ttctttttac gttaaattca actcaaaacc  660
aattgctcaa gtaatactaa tttcaccatt aattttgcaa tattttggta gcaatcgacg  720
agaccaattt tgggacgaat cggtttattg atcgtattgc atggacacca tattatttta  780
ggtaaacttt caacgcaaaa ccaatagacc ttaatgataa atcgtttcaa acttttgatt  840
taactttca tttcagtgca aacgttatcg cttttagatt ccttgttaaa ctttcaggca  900
aataaactgg aagcagactc aaaacgataa ggaaagagct cgaagaacca actgaagtgg  960
aaagtgaact gaaacgaaga cttgaccagc taactaatca t                     1001

SEQ ID NO: 17            moltype = DNA   length = 121
FEATURE                  Location/Qualifiers
source                   1..121
                         mol_type = other DNA
                         organism = Brassica napus
SEQUENCE: 17
tgcttataat agttagttgc ttccagaggr aacacatatt caaacagaca agattagcta   60
ygacagttgc ctggtaatat ttttatttt attaggcttc gtttggaatg attattataa  120
t                                                                  121

SEQ ID NO: 18            moltype = DNA   length = 1001
FEATURE                  Location/Qualifiers
source                   1..1001
                         mol_type = other DNA
                         organism = Brassica napus
SEQUENCE: 18
gtattgcatg gacaccatat tattttaggt aaactttcaa cgcaaaacca atagacctta   60
atgataaatc gtttcaaact tttgatttaa cttttcattt cagtgcaaac gttatcgctt  120
ttagattcct tgttaaactt tcaggcaaat aaactggaag cagactcaaa cgataagga  180
aagagctcga agaaccaact gaagtggaaa gtgaactgaa acgaagactt gaccagctaa  240
ctaatcatct tactcaaaaa caatcccagg tatatgaata cttttaaata aaagagaatt  300
cagacaaaac taatataaaa acttccaact ctcctgccaa atttaccaag tcgactttcc  360
tcataggaag caactctatc gtttagaatc catattttaa ctacttcaca ctattctctc  420
cataatctct ctctcataca aatacattga aggttttgac aacaaacaca aagctctaga  480
actcaagcag gagcaattga sactctttca atctcaacta catactccag cgaagcagaa  540
ggcggtatct gaaaacccga ttcaagttca gcaccctctt ctccaaatcc taaagctggt  600
ggaacgatca ctctccttt acctccggcc ttcatcgacc tcagaacata atctacgcct  660
tcgcataatc ctttgctata tggctttgaa cccaccacaa gtgccaatgg cttcttattc  720
ttgtctttgc ttccaaatgt gtcaacaaac acttgtcccg tttcttcac ttgtccctc  780
atattaatca ctaccaaatc acctgctctt ggtgttgccc ctcctccaag ccgtagatca  840
tagtacctgc atagtttgat tcaatatagt ccaagacttg accgaagcta aggagaccca  900
ttgacaaaat gtacctaatg ccattgggca agacaatctc cttctcttct tcgacgtctc  960
tacaaacaca ccatacaaaa gcagttcaa agctttgtga g                     1001

SEQ ID NO: 19            moltype = DNA   length = 1001
FEATURE                  Location/Qualifiers
source                   1..1001
```

```
                         mol_type = other DNA
                         organism = Brassica napus
SEQUENCE: 19
atcatcttac tcaaaaacaa tcccaggtat atgaatactt ttaaataaaa gagaattcag     60
acaaaactaa tataaaaact tccaactctc ctgccaaatt taccaagtcg actttcctca    120
taggaagcaa ctctatcgtt tagaatccat attttaacta cttcacacta ttctctccat    180
aatctctctc tcatacaaat acattgaagg ttttgacaac aaaacacaaag ctctagaact    240
caagcaggag caattgagac tctttcaatc tcaactacat actccagcga agcagaaggc    300
ggtatctgaa aacccgattc aagttcagca ccctcttctc caaatcctaa agctggtgga    360
acgatcactc tcctttacc tccggccttc atcgacctca gaacataatc tacgccttcg     420
cataatcctt tgctatatgg ctttgaaccc accacaagtg ccaatggctt cttattcttg    480
tctttgcttc caaatgtgtc macaaacact tgtcccgttt cttgcacttg tcccttcata    540
ttaatcacta ccaaatcacc tgctcttggt gttgcccctc ctccaagccg tagatcatag    600
tacctgcata gtttgattca atatagtcca agacttgacc gaagctaagg agacccattg    660
acaaaatgta cctaatgcca ttgggcaaga caatctcctt ctcttcttcg acgtctctac    720
aaacacacca tacaaaagca gttccaaagc tttgtgagag tgatgacaac taagacagta    780
acttgaagct atggagatgt gaaaaccttg tgttagcttc ttcttgagaa acctcaagcc    840
gtgttttgat ctgctcggag atcacaccga aagctagaaa ccccgcccag gcaagacccg    900
caccgattcc aaaccgtctg gtcaaagaag aagcgaccca atccgtcgtc tcaacgctgg    960
tcttcttcct cttctgttgc gatgcgaggg gttgctccgt c                       1001

SEQ ID NO: 20           moltype = DNA  length = 1001
FEATURE                 Location/Qualifiers
source                  1..1001
                        mol_type = other DNA
                        organism = Brassica napus
SEQUENCE: 20
atgaatactt ttaaataaaa gagaattcag acaaaactaa tataaaaact tccaactctc     60
ctgccaaatt taccaagtcg actttcctca taggaagcaa ctctatcgtt tagaatccat    120
attttaacta cttcacacta ttctctccat aatctctctc tcatacaaat acattgaagg    180
ttttgacaac aaaacacaaag ctctagaact caagcaggag caattgagac tctttcaatc    240
tcaactacat actccagcga agcagaaggc ggtatctgaa aacccgattc aagttcagca    300
ccctcttctc caaatcctaa agctggtgga acgatcactc tccttttacc tccggccttc    360
atcgacctca gaacataatc tacgccttcg cataatcctt tgctatatgg ctttgaaccc    420
accacaagtg ccaatggctt cttattcttg tctttgcttc caaatgtgtc aacaaacact    480
tgtcccgttt cttgcacttg ycccttcata ttaatcacta ccaaatcacc tgctcttggt    540
gttgcccctc ctccaagccg tagatcatag tacctgcata gtttgattca atatagtcca    600
agacttgacc gaagctaagg agacccattg acaaaatgta cctaatgcca ttgggcaaga    660
caatctcctt ctcttcttcg acgtctctac aaacacacca tacaaaagca gttccaaagc    720
tttgtgagag tgatgacaac taagacagta acttgaagct atggagatgt gaaaaccttg    780
tgttagcttc ttcttgagaa acctcaagcc gtgttttgat ctgctcggag atcacaccga    840
aagctagaaa ccccgcccag gcaagacccg caccgattcc aaaccgtctg gtcaaagaag    900
aagcgaccca atccgtcgtc tcaacgctgg tcttcttcct cttctgttgc gatgcgaggg    960
gttgctccgt ctttacggat tgagtcggag tagaagaaga c                       1001

SEQ ID NO: 21           moltype = DNA  length = 1001
FEATURE                 Location/Qualifiers
source                  1..1001
                        mol_type = other DNA
                        organism = Brassica napus
SEQUENCE: 21
tcaaagaaga agcgacccaa tccgtcgtct caacgctggt cttcttcctc ttctgttgcg     60
atgcgagggg ttgctccgtc tttacggatt gagtcggagt agaagaagac tctggctgag    120
aaggagggt ctgctccgga ggagtggaag aagaggcgca acagaggtga tacggcgccg     180
tcttcgtgaa cggctttgaa aggaacggag ctgtaacggt gaatagattc gccatttcgg    240
cataaaataa aataaaaacc tcagctttat tataagtata taaacgctta tcctgttcgt    300
gtgattcatt ttaaagacag aagtcaagcc aagttcttgt cactgtcagt gataaaccga    360
atccggttag gctaaaccgg gtcgtcgaaa ttattaaaaa aaattaaatt gtttcttctt    420
cttcttctcc tttctctctc caatcagtta ggaagaaggt cgtgacccac tccgaaggac    480
aaaaccgaga gacgatccga kaaataaggt gaatttgacg agaatcatta ggctgagaag    540
gaaactcgga gacccaaaat cgtaaatcac caatctttaa tctgtttttc taattcagta    600
gtagtagttg atgggtggtg gtgggaatct cgtcgacggt gttcgtcgtt ggcttttttca    660
acgaccctct tcttccaata ataatcctca cgaacccatt gttccaaagt ctgatacttt    720
ttctattccc catcatcaat ctgagcttat cattaccgaa gatctcgatt tctctggtct    780
caagcttatc aaagttccca aacgtcatca cttacccatg gatcctcaaa agaaggtacc    840
ttttggcgcg atcactgatt gtgtagacat catttgatct gtgatctttg tttgattgaa    900
gtttacttct attaatgttt tgtacattgt tcaacaagta gctagatttt gattaggcct    960
tttatagggt gttattgatt attgatttat ttatttattt g                       1001

SEQ ID NO: 22           moltype = DNA  length = 1001
FEATURE                 Location/Qualifiers
source                  1..1001
                        mol_type = other DNA
                        organism = Brassica napus
SEQUENCE: 22
attaggctga gaaggaaact cggagaccca aaatcgtaaa tcaccaatct ttaatctgtt     60
tttctaattc agtagtagta gttgatgggt ggtggtggga atctcgtcga cggtgttcgt    120
cgttggcttt ttcaacgacc ctcttcttcc aataataatc ctcacgaacc cattgttcca    180
aagtctgata ctttttctat tccccatcat caatctgagc ttatcattac cgaagatctc    240
```

-continued

```
gatttctctg gtctcaagct tatcaaagtt cccaaacgtc atcacttacc catggatcct    300
caaaagaagg taccttttgg cgcgatcact gattgtgtag acatcatttg atctgtgatc    360
tttgtttgat tgaagtttac ttctattaat gttttgtaca ttgttcaaca agtagctaga    420
ttttgattag gcctttata gggtgttatt gattattgat ttatttattt atttgattgg    480
atcctactgt ttgttcaggg ygtgcaggaa aaggacttct tcacggagta cggagaagca    540
aacaggtacc aggttcaaga agtcgttggt aaaggaagct acggtgttgt ggcctctgct    600
ctagacacac acactggcga aagagttgct atcaagaaga tcaacgacgt ctttgagcat    660
gtctctgatg caaccaggat tctcagggag atcaagctgc tgaggttgct taagcatccg    720
gatgttgtgg agattaagca tattatgctg cctccttctc gtagagagt cagggatatt    780
tacgttgtgt ttgagctgat ggagtctgat cttcatcagg tgattaaggc gaatgatgat    840
ttgactcctg atcattatca gttcttcttg tatcagcttc tccgtggtct caaatatgtc    900
cacgcaggtt aagtttctgg ttttaaaaca gtcttctctt ttgtctgtct ttattgaaac    960
gtttgtgtgt tttcagctaa tgtgtttcat cgggatttga a                        1001
```

```
SEQ ID NO: 23          moltype = DNA   length = 1001
FEATURE                Location/Qualifiers
source                 1..1001
                       mol_type = other DNA
                       organism = Brassica napus SEQUENCE: 23
gacccaaaat cgtaaatcac caatctttaa tctgtttttc taattcagta gtagtagttg    60
atgggtggtg gtgggaatct cgtcgacggt gttcgtcgtt ggcttttttca acgaccctct    120
tcttccaata ataatcctca cgaacccatt gttccaaagt ctgatacttt ttctattccc    180
catcatcaat ctgagcttat cattaccgaa gatctcgatt tctctggtct caagcttatc    240
aaagttccca aacgtcatca cttacccatg gatcctcaaa agaaggtacc ttttggcgcg    300
atcactgatt gtgtagacat catttgatct gtgatctttg tttgattgaa gtttacttct    360
attaatgttt tgtacattgt tcaacaagta gctagatttt gattaggcct tttataggg    420
gttattgatt attgatttat ttatttattt gattggatcc tactgtttgt tcagggtgtg    480
caggaaaagg acttcttcac rgagtacgga gaagcaaaca ggtaccaggt tcaagaagtc    540
gttggtaaag gaagctacgg tgttgtggcc tctgctctag acacacacac tggcgaaaga    600
gttgctatca agaagatcaa cgacgtcttt gagcatgtct ctgatgcaac caggattctc    660
agggagatca agctgctgag gttgcttaag catccggatg ttgtggagat taagcatatt    720
atgctgcctc cttctcgtag agagttcagg gatatttacg ttgtgtttga gctgatggag    780
tctgatcttc atcaggtgat taaggcgaat gatgatttga ctcctgatca ttatcagttt    840
ttcttgtatc agcttctccg tggtctcaaa tatgtccacg caggttaagt ttctggtttt    900
aaaacagtct tctcttttgt ctgtcttat tgaaacgttt gtgtgttttc agctaatgtg    960
tttcatcggg atttgaaacc aaagaacatt ctagctaatg c                        1001
```

```
SEQ ID NO: 24          moltype = DNA   length = 1001
FEATURE                Location/Qualifiers
source                 1..1001
                       mol_type = other DNA
                       organism = Brassica napus SEQUENCE: 24
tttcaacgac cctcttcttc caataataat cctcacgaac ccattgttcc aaagtctgat    60
acttttcta ttccccatca tcaatctgag cttatcatta ccgaagatct cgatttctct    120
ggtctcaagc ttatcaaagt tcccaaacgt catcacttac ccatggatcc tcaaaagaag    180
gtaccttttg gcgcgatcac tgattgtgta gacatcattt gatctgtgat ctttgtttga    240
ttgaagtttac cttctattaa tgttttgtac attgttcaac aagtagctag attttgatta    300
ggcctttat agggtgttat tgattattga tttatttatt tatttgattg gatcctactg    360
tttgttcagg gtgtgcagga aaaggacttc ttcacggagt acggagaagc aaacaggtac    420
caggttcaag aagtcgttgg taaaggaagc tacggtgttg tggcctctgc tctagacaca    480
cacactggcg aaagagttgc yatcaagaag atcaacgacg tctttgagca tgtctctgat    540
gcaaccagga ttctcaggga gatcaagctg ctgaggttgc ttaagcatcc ggatgttgtg    600
gagattaagc atattatgct gcctccttct cgtagagagt tcagggatat ttacgttgtg    660
tttgagctga tggagtctga tcttcatcag gtgattaagg cgaatgatga tttgactcct    720
gatcattatc agttcttctt gtatcagctt ctccgtggtc tcaaatatgt ccacgcaggt    780
taagtttctg gttttaaaac agtcttctct tttgtctgtc tttattgaaa cgtttgtgtg    840
ttttcagcta atgtgtttca tcgggatttg aaaccaaaga acattctagc taatgctgat    900
tgcaagttga agatctgtga tttttggactc gctcgtgtct cttttaacga cgcaccaact    960
gctatattct ggactgtgag tcctctaatt tgaatgcagc a                        1001
```

```
SEQ ID NO: 25          moltype = DNA   length = 1001
FEATURE                Location/Qualifiers
source                 1..1001
                       mol_type = other DNA
                       organism = Brassica napus SEQUENCE: 25
cccattgttc caaagtctga tactttttct attccccatc atcaatctga gcttatcatt    60
accgaagatc tcgatttctc tggtctcaag cttatcaaag ttcccaaacg tcatcactta    120
cccatggatc ctcaaaagaa ggtacctttt ggcgcgatca ctgattgtgt agacatcatt    180
tgatctgtga tctttgtttg attgaagttt acttctatta atgttttgta cattgttcaa    240
caagtagcta gattttgatt aggccttta agggtgttta ttgattattg atttatttat    300
ttatttgatt ggatcctact gtttgttcag gtgtgtgcagg aaaaggactt cttcacggag    360
tacggagaag caaacaggta ccaggttcaa gaagtcgttg gtaaaggaag ctacggtgtt    420
gtggcctctg ctctagacac acacactggc gaaagagttg ctatcaagaa gatcaacgac    480
gtctttgagc atgtctctga ygcaaccagg attctcaggg agatcaagct gctgaggttg    540
cttaagcatc cggatgttgt ggagattaag catattatgc tgcctccttc tcgtagagag    600
ttcagggata tttacgttgt gtttgagctg atggagtctg atcttcatca ggtgattaag    660
```

```
gcgaatgatg atttgactcc tgatcattat cagttcttct tgtatcagct tctccgtggt   720
ctcaaatatg tccacgcagg ttaagtttct ggttttaaaa cagtcttctc ttttgtctgt   780
ctttattgaa acgtttgtgt gttttcagct aatgtgtttc atcgggattt gaaaccaaag   840
aacattctac ctaatgctga ttgcaagttg aagatctgtg attttggact cgctcgtgtc   900
tcttttaacg acgcaccaac tgctatattc tggactgtga gtcctctaat ttgaatgcag   960
cagagcttct cattaaactg tttgtgaact cactcttttat t                      1001
```

SEQ ID NO: 26            moltype = DNA  length = 1001
FEATURE                  Location/Qualifiers
source                  1..1001
                            mol_type = other DNA
                            organism = Brassica napus
SEQUENCE: 26

```
ttacccatgg atcctcaaaa gaaggtacct tttggcgcga tcactgattg tgtagacatc   60
atttgatctg tgatctttgt ttgattgaag tttacttcta ttaatgtttt gtacattgtt   120
caacaagtag ctagattttg attaggcctt ttataggg tg ttattgatta ttgatttatt   180
tatttatttg attggatcct actgtttgtt cagggtgtgc aggaaaagga cttcttcacg   240
gagtacggag aagcaaacag gtaccaggtt caagaagtcg ttggtaaagg aagctacggt   300
gttgtggcct ctgctctaga cacacacact ggcgaaagag ttgctatcaa gaagatcaac   360
gacgtctttg agcatgtctc tgatgcaacc aggattctca gggagatcaa gctgctgagg   420
ttgcttaagc atccggatgt tgtggagatt aagcatatta tgctgcctcc ttctcgtaga   480
gagttcaggg atatttacgt ygtgtttgag ctgatgagat ctgatcttca tcaggtgatt   540
aaggcgaatg atgatttgac tcctgatcat tatcagttct tcttgtatca gcttctccgt   600
ggtctcaaat atgtccacgc aggttaagtt tctggtttta aaacagtctt ctcttttgtc   660
tgtctttatt gaaacgtttg tgtgttttca gctaatgtgt ttcatcggga tttgaaacca   720
aagaacattc tagctaatgc tgattgcaag ttgaagatct gtgattttgg actcgctcgt a   780
gtctctttta acgacgcacc aactgctata ttctggactc tgagtcctct aatttgaatg   840
cagcagagct tctcattaaa ctgtttgtga actcactctt ttatctatgt tttgtaggat   900
tatgtagcta ctcggtggta ccgtgcccct gaactctgtg gatcgttttt ctccaaagta   960
agattctttt ttttgttta ttcactgaac ctctctgtat c                       1001
```

SEQ ID NO: 27            moltype = DNA  length = 1001
FEATURE                  Location/Qualifiers
source                  1..1001
                            mol_type = other DNA
                            organism = Brassica napus
SEQUENCE: 27

```
aaaacagtct tctcttttgt ctgtctttat tgaaacgttt gtgtgttttc agctaatgtg   60
tttcatcggg atttgaaacc aaagaacatt ctagctaatg ctgattgcaa gttgaagatc   120
tgtgattttg gactcgctcg tgtctctttt aacgacgcac caactgctat attctggact   180
gtgagtcctc taatttgaat gcagcagagc ttctcattaa actgtttgtg aactcactct   240
tttatctatg ttttgtagga ttatgtagct actcggtggt accgtgcccc tgaactctgt   300
ggatcgtttt tctccaaagt aagattcttt ttttttgtt attcactgaa cctctctgta   360
tcacaagaac ggacttcttg atctaggtcc tatattttca taagatatac cgtctaatgc   420
taagttaact ttcagtacac tcctgcgatt gatatatgga gtgttggttg cattttttgcg   480
gaaatgatat tgggaaagcc wttgtttccc gggaagaacg tggtgcacca acttgatctt   540
atgactgact ttcttggcac tcctccgcct gagtccatat caagggttag tcactcaaac   600
atgtgttaca ttcccatcat ttgagagcta gttaatgagt tttttttgtt tttttttgca   660
atcttgaaat tatgacagat aagaaatgaa aaggcgagga gatatctaag cagcatgagg   720
aagaaacagc cggttccttt ctctcacaag ttccctaaag ctgatccttt ggctctccgc   780
cttctcgaac gccttattgc ctttgatcct aaagatcgtg tctcagctga agatgtagt   840
gacaagcaac tttcattttt tttttaatta caaagactta aaactctcaa gttcattatt   900
ctgatttggt tatttacagg cactagctga tccttatttc agtggtctgt caaactcaga   960
gcgtgaacca tcaacgcagc caatctcaaa gcttgagttt g                       1001
```

SEQ ID NO: 28            moltype = DNA  length = 1002
FEATURE                  Location/Qualifiers
variation             502
                            note = where n is an insertion/deletion [+/TT]
source                  1..1002
                            mol_type = other DNA
                            organism = Brassica napus
SEQUENCE: 28

```
ttttggactc gctcgtgtct cttttaacga cgcaccaact gctatattct ggactgtgag   60
tcctctaatt tgaatgcagc agagcttctc attaaactgt ttgtgaactc actcttttat   120
ctatgttttg taggattatg tagctactcg gtggtaccgt gccctgaac tctgtggatc   180
gttttctcc aaagtaagat tctttttttt tgtttattca ctgaacctct ctgtatcaca   240
agaacggact tcttgatcta ggtcctatat tttcataaga tataccgtct aatgctaagt   300
taactttcag tacactcctg cgattgatat atggagtgtt ggttgcattt ttgcggaaat   360
gatattggga aagcctttgt ttcccgggaa gaacgtggtg caccaacttg atcttatgac   420
tgactttctt ggcactcctc cgcctgagtc catatcaagg gttagtcact caaacatgtg   480
ttacattccc atcatttgag angctagtta atgagttttt tttgtttttt tttgcaatct   540
tgaaattatg acagataaga aatgaaaagg cgaggagata tctaagcagc atgaggaaga   600
aacagccggt tcctttctct cacaagttcc ctaaagctga tcctttggct ctccgccttc   660
tcgaacgcct tattgccttt gatcctaaag atcgtgtctc agctgaagat gtaagcgaca   720
agcaactttc attttttttt taattacaaa gacttaaaac tctcaagttc attattctga   780
tttggttatt tacaggcact agctgatcct tatttcagtg tctgtcaaa ctcagagcgt   840
gaaccatcaa cgcagccaat ctcaaagctt gagtttgatt tgagagaaa gaagttgaac   900
aaagatgacg tcagagaatt aatctaccga gaggtaacac aaaaaaaaat gctttttgact   960
```

```
atgtcttatt gttctcttca ttgatctaac attcacttta tc                        1002

SEQ ID NO: 29          moltype = DNA  length = 1001
FEATURE                Location/Qualifiers
source                 1..1001
                       mol_type = other DNA
                       organism = Brassica napus
SEQUENCE: 29
ttggactcgc tcgtgtctct tttaacgacg caccaactgc tatattctgg actgtgagtc     60
ctctaatttg aatgcagcag agcttctcat taaactgttt gtgaactcac tcttttatct     120
atgttttgta ggattatgta gctactcggt ggtaccgtgc ccctgaactc tgtgatcgt      180
ttttctccaa agtaagattc tttttttttg tttattcact gaacctctct gtatcacaag     240
aacggacttc ttgatctagg tcctatattt tcataagata taccgtctaa tgctaagtga     300
actttcagta cactcctgcg attgatatat ggagtgttgg ttgcattttt gcggaaatga     360
tattgggaaa gcctttgttt cccgggaaga acgtggtgca ccaacttgat cttatgactg     420
actttcttgg cactcctccg cctgagtcca tatcaagggt tagtcactca aacatgtgtt     480
acattcccat catttgagag ytagttaatg agtttttttt gttttttttt gcaatcttga     540
aattatgaca gataagaaat gaaaaggcga ggagatatct aagcagcatg aggaagaaac     600
agccggttcc tttctctcac aagttcccta aagctgatcc tttggctctc cgccttctcg     660
aacgccttat tgcctttgat cctaaagatc gtgtctcagc tgaagatgta agcgacaagc     720
aactttcatt ttttttttaa ttacaaagac ttaaaactct caagttcatt attctgattt     780
ggttatttac aggcactagc tgatccttat ttcagtggtc tgtcaaactc agagcgtgaa     840
ccatcaacgc agccaatctc aaagcttgag tttgattttg agagaaagaa gttgaacaaa     900
gatgacgtca gagaattaat ctaccgagag gtaacacaaa aaaaaatgct tttgactatg     960
tcttattgtt ctcttcattg atctaacatt cactttatct t                        1001

SEQ ID NO: 30          moltype = DNA  length = 1001
FEATURE                Location/Qualifiers
source                 1..1001
                       mol_type = other DNA
                       organism = Brassica napus
SEQUENCE: 30
agtacactcc tgcgattgat atatggagtg ttggttgcat ttttgcggaa atgatattgg     60
gaaagccttt gtttcccggg aagaacgtgg tgcaccaact tgatcttatg actgactttc     120
ttggcactcc tccgcctgag tccatatcaa gggttagtca ctcaaacatg tgttacattc     180
ccatcatttg agagctagtt aatgagtttt ttttgttttt ttttgcaatc ttgaaattat     240
gacagataag aaatgaaaag gcgaggagat atctaagcag catgaggaag aaacagccgg     300
ttcctttctc tcacaagttc cctaaagctg atcctttggc tctccgcctt ctcgaacgcc     360
ttattggcct tgatcctaaa gatcgtgtct cagctgaaga tgtaagcgac aagcaacttt     420
cattttttt ttaattacaa agacttaaaa ctctcaagtt cattattctg atttggttat     480
ttacaggcac tagctgatcc wtatttcagt ggtctgtcaa actcagagcg tgaaccatca     540
acgcagccaa tctcaaagct tgagtttgat tttgagagaa agaagttgaa caaagatgac     600
gtcagagaat taatctaccg agaggtaaca caaaaaaaaa tgcttttgac tatgtcttat     660
tgttctcttc attgatctaa cattcacttt atctttggga aaaacattta gatattggag     720
tatcatcctc agatgctgga ggagtacaag cgcggtggtg atcagctcag cttcatgtac     780
cctaggttag ctaattaaac acctcatgaa ctataattcc ctgaaaacag aatgaaacca     840
agaactcttc tgttgtttac gcagtggggt tgatcggttc agaggcagt ttgctcacct     900
tgaagagaat caaggtaaac caggagcagg ggcaggagga ggaagaagta ctgcaatgca     960
tagacaccat gcttccttgc caatgtaatg tcttttttcac a                       1001

SEQ ID NO: 31          moltype = DNA  length = 1001
FEATURE                Location/Qualifiers
source                 1..1001
                       mol_type = other DNA
                       organism = Brassica napus
SEQUENCE: 31
acactcctgc gattgatata tggagtgttg gttgcatttt tgcggaaatg atattgggaa     60
agcctttgtt tcccgggaag aacgtggtgc accaacttga tcttatgact gactttcttg     120
gcactcctcc gcctgagtcc atatcaaggg ttagtcactc aaacatgtgt tacattccca     180
tcatttgaga gctagttaat gagttttttt tgttttttt tgcaatcttg aaattatgac     240
agataagaaa tgaaaaggcg aggagatatc taagcagcat gaggaagaaa cagccggttc     300
ctttctctca agttccct aaagctgatc ctttggctct ccgccttctc gaacgcctta     360
ttgcctttga tcctaaagat cgtgtctcag ctgaagatgt aagcgacaag caactttcat     420
tttttttta attacaaaga cttaaaactc tcaagttcat tattctgatt tggttattta     480
caggcactag ctgatcctta yttcagtggt ctgtcaaact cagagcgtga accatcaacg     540
cagccaatct caaagcttga gtttgatttt gagagaaaga gttgaacaa agatgacgtc     600
agagaattaa tctaccgaga ggtaacacaa aaaaaaatgc ttttgactat gtcttattgt     660
tctcttcatt gatctaacat tcactttatc tttgggaaaa acatttagat attggagtat     720
catcctcaga tgctggagga gtacaagcgc ggtggtgatc agctcagctt catgtaccct     780
aggttagcta attaaacacc tcatgaacta taattccctg aaaacagaat gaaaccaaga     840
actcttctgt tgtttacgca gtgggttga tcggttcaag aggcagtttg ctcaccttga     900
agagaatcaa ggtaaccag gagcagggc aggaggagga gaagtactg caatgcatag     960
acaccatgct tccttgccaa tgtaatgtct ttttcacaga a                        1001

SEQ ID NO: 32          moltype = DNA  length = 1002
FEATURE                Location/Qualifiers
variation              502
                       note = where n is an insertion/deletion [+/A]
source                 1..1002
```

```
                         mol_type = other DNA
                         organism = Brassica napus
SEQUENCE: 32
gtccatatca agggttagtc actcaaacat gtgttacatt cccatcattt gagagctagt    60
taatgagttt tttttgtttt tttttgcaat cttgaaatta tgacagataa gaaatgaaaa   120
ggcgaggaga tatctaagca gcatgaggaa gaaacagccg gttcctttct ctcacaagtt   180
ccctaaagct gatcctttgg ctctccgcct tctcgaacgc cttattgcct ttgatcctaa   240
agatcgtgtc tcagctgaag atgtaagcga caagcaactt tcattttttt tttaattaca   300
aagacttaaa actctcaagt tcattattct gatttggtta tttacaggca ctagctgatc   360
cttatttcag tggtctgtca aactcagagc gtgaaccatc aacgcagcca atctcaaagc   420
ttgagtttga ttttgagaga aagaagttga acaaagatga cgtcagagaa ttaatctacc   480
gagaggtaac acaaaaaaaa antgcttttg actatgtctt attgttctct tcattgatct   540
aacattcact ttatctttgg gaaaaacatt tagatattgg agtatcatcc tcagatgctg   600
gaggagtaca agcgcggtgg tgatcagctc agcttcatgt accctaggtt agctaattaa   660
acacctcatg aactataatt ccctgaaaac agaatgaaac caagaactct tctgttgttt   720
acgcagtggg gttgatcggt tcaagaggca gtttgctcac cttgaagaga atcaaggtaa   780
accaggagca ggggcaggag gaggaagaag tactgcaatg catagacacc atgcttcctt   840
gccaatgtaa tgtctttttc acagaatctc ttgctttgct ctctcttct ctgaaagcgt    900
tgggcttctt tgtgattgtg tgttgcagag agagagttcc tgctcagagt ggtcagactg   960
tagaagaaag cagtgatgtt gagagaagag cagcagctgc tg                      1002

SEQ ID NO: 33             moltype = DNA   length = 1001
FEATURE                   Location/Qualifiers
source                    1..1001
                          mol_type = other DNA
                          organism = Brassica napus
SEQUENCE: 33
ctagctgatc cttatttcag tggtctgtca aactcagagc gtgaaccatc aacgcagcca    60
atctcaaagc ttgagtttga ttttgagaga aagaagttga acaaagatga cgtcagagaa   120
ttaatctacc gagaggtaac acaaaaaaaa atgcttttg ctatgtctta ttgttctctt    180
cattgatcta acattcactt tatctttggg aaaaacattt agatattgga gtatcatcct   240
cagatgctgg aggagtacaa gcgcggtggt gatcagctca gcttcatgta ccctaggtta   300
gctaattaaa cacctcatga actataattc cctgaaaaca gaatgaaacc aagaactct    360
ctgttgttta cgcagtgggg ttgatcggtt caagaggca gtttgctcacc ttgaagaga    420
tcaaggtaaa ccaggagcag ggggcaggag aggaagaagt actgcaatgc atagacacca   480
tgcttccttg ccaatgtaat rtctttttca cagaatctct tgctttgctc tctctttctc   540
tgaaagcgtt gggcttcttt gtgattgtgt gttgcagaga gagagttcct gctcagagtg   600
gtcagactgt agaagaaagc agtgatgttg agagaagagc agcagctgct gtggcttcaa   660
ctttggaatc tgaggaagca gacaatggag gaggttacag tgctcgtagc ctcatgaaga   720
gttcgagcat cagtggttct aaatgcatcg gtgtccaatc taaaaccgac aaagaggtta   780
gttagttagt tagttagtgg agttaaaaaa acagaggatc ttgaaaggaa catggagatg   840
gagtttgctt acttactgtt gtttctgttc tgtgttgtag acaccatag ctgaggaagg    900
agatgatgaa tcagtggcgg agcttactga tagagttgct tctcttcgta attcttaaaa   960
cgtttttgtt ttttttttg gcgtttggtg aaagcttttct g                       1001

SEQ ID NO: 34             moltype = DNA   length = 1001
FEATURE                   Location/Qualifiers
variation                 501
                          note = where n is an insertion/deletion [-/T]
source                    1..1001
                          mol_type = other DNA
                          organism = Brassica napus
SEQUENCE: 34
atccttattt cagtggtctg tcaaactcag agcgtgaacc atcaacgcag ccaatctcaa    60
agcttgagtt tgattttgag agaaagaagt tgaacaaaga tgacgtcaga gaattaatct   120
accgagaggt aacacaaaaa aaaatgcttt tgactatgtc ttattgttct cttcattgat   180
ctaacattca ctttatcttt gggaaaaaca tttagatatt ggagtatcat cctcagatgc   240
tggaggagta caagcgcggt ggtgatcagc tcagcttcat gtaccctagg ttagctaatt   300
aaacacctca tgaactataa ttccctgaaa acagaatgaa ccaagaact cttctgttgt    360
ttacgcagtg gggttgatcg gttcaagagg cagtttgctc accttgaaga gaatcaaggt   420
aaaaccagga gcaggggcag gaggaggaag agtactgcaa tgcatagaca ccatgcttcc   480
ttgccaatg aatgtctttt ncacagaatc tcttgctttg ctctctcttt ctctgaaagc   540
gttgggcttc tttgtgattg tgtgttgcag agagagagtt cctgctcaga gtggtcagac   600
tgtagaagaa agcagtgatg ttgagagaag agcagcagct gctgtggctt caacttggga   660
atctgaggaa gcagacaatg gaggaggtta cagtgctcgt agcctcatga gagttcgag    720
catcagtggt tctaaatgca tcggtgtcca atctaaaacc gacaaagagg ttagttagtt   780
agttagttag tggagttaaa aaaacagagg atcttgaaag gaacatggag atggagtttg   840
cttacttact gttgtttctg ttctgtgttg taggacacca tagctgagga aggagatgat   900
gaatcagtgg tcggagctta ctgatagagt tgcttctctt cgtaattctta aaacgtttt    960
gtttttttt ttggcgtttg gtgaaagctt tctggtgaaa a                        1001

SEQ ID NO: 35             moltype = DNA   length = 1001
FEATURE                   Location/Qualifiers
source                    1..1001
                          mol_type = other DNA
                          organism = Brassica napus
SEQUENCE: 35
acgtcagaga attaatctac cgagaggtaa cacaaaaaaa aatgcttttg actatgtctt    60
attgttctct tcattgatct aacattcact ttatctttgg gaaaaacatt tagatattgg   120
```

-continued

```
agtatcatcc tcagatgctg gaggagtaca agcgcggtgg tgatcagctc agcttcatgt    180
accctaggtt agctaattaa acacctcatg aactataatt ccctgaaaac agaatgaaac    240
caagaactct tctgttgttt acgcagtggg gttgatcggt tcaagaggca gtttgctcac    300
cttgaagaga atcaaggtaa accaggagca ggggcaggag gaggaagaag tactgcaatg    360
catagacacc atgcttcctt gccaatgtaa tgtctttttc acagaatctc ttgctttgct    420
ctctctttct ctgaaagcgt tgggcttctt tgtgattgtg tgttgcagag agagagttcc    480
tgctcagagt ggtcagactg yagaagaaag cagtgatgtt gagagaagag cagcagctgc    540
tgtggcttca actttggaat ctgaggaagc agacaatgga ggaggttaca gtgctcgtag    600
cctcatgaag agttcgagca tcagtggttc taaatgcatc ggtgtccaat ctaaaaccga    660
caaagaggtt agttagttag ttagttagtg gagttaaaaa aacagaggat cttgaaagga    720
acatggagat ggagtttgct tacttactgt tgtttctgtt ctgtgttgta ggacaccata    780
gctgaggaag gagatgatga atcagtggcg gagcttactg atagagttgc ttctcttcgt    840
aattcttaaa acgtttttgt tttttttttt ggcgtttggt gaaagctttc tggtgaaaat    900
tggtttctac attttatttt cacttcttcc acatctatct tcgtggttgg gtttgatttg    960
ttggatttaa tagtttgggg gcgagaatga gaccttttta a                       1001
```

SEQ ID NO: 36    moltype = DNA  length = 1001
FEATURE          Location/Qualifiers
source           1..1001
                 mol_type = other DNA
                 organism = Brassica napus
SEQUENCE: 36
```
acgcagtggg gttgatcggt tcaagaggca gtttgctcac cttgaagaga atcaaggtaa    60
accaggagca ggggcaggag gaggaagaag tactgcaatg catagacacc atgcttcctt    120
gccaatgtaa tgtctttttc acagaatctc ttgctttgct ctctctttct ctgaaagcgt    180
tgggcttctt tgtgattgtg tgttgcagag agagagttcc tgctcagagt ggtcagactg    240
tagaagaaag cagtgatgtt gagagaagag cagcagctgc tgtggcttca actttggaat    300
ctgaggaagc agacaatgga ggaggttaca gtgctcgtag cctcatgaag agttcgagca    360
tcagtggttc taaatgcatc ggtgtccaat ctaaaaccga caaagaggtt agttagttag    420
ttagttagtg gagttaaaaa aacagaggat cttgaaagga acatggagat ggagtttgct    480
tacttactgt tgtttctgtt ytgtgttgta ggacaccata gctgaggaag gagatgatga    540
atcagtggcg gagcttactg atagagttgc ttctcttcgt aattcttaaa acgtttttgt    600
tttttttttt ggcgtttggt gaaagctttc tggtgaaaat tggtttctac attttatttt    660
cacttcttcc acatctatct tcgtggttgg gtttgatttg ttggatttaa tagtttgggg    720
gcgagaatga gaccttttta ataagaacat ctatctccat gtaatttctt ttatcctttt    780
ctataaattg ttctttcaat ctttttaccg attcagtttg cttaagtaca tcatgaaatc    840
agaattaaac taaaaaatag tatactaaaa aaggaaaaca tccaaaaaac ctttatagtt    900
gaagtaaaca tatatatata tatatatata tatatgcagt ttgctttata ttatgatctg    960
aattagttat atatacatac taagtgtttt tcaaaaatag t                       1001
```

SEQ ID NO: 37    moltype = DNA  length = 1001
FEATURE          Location/Qualifiers
source           1..1001
                 mol_type = other DNA
                 organism = Brassica napus
SEQUENCE: 37
```
agataccacc ttcaccggtt gaaaacaagt tttgcgagaa tcacgttcga gtaaaattta    60
tgcacttcat ttaaatatta caagtgttta tttattcgac tataaatgtt cgtaaagacc    120
acaattcatt tgaagattta ttttattttt cactctcata aaatcctttt gtattcacca    180
gggtcatcaa tatacataca ctcatctgat ttatatagtt gcatggcagt taattgcaat    240
ttagtcctag gtgatttgtt ctattataaa tcaaaccaag agagttgcat gttttccatg    300
acgaagtatc ttctactagt agattactgg cagttggtgt aatagttacc accagtagaa    360
actagtttac caacgagtac aacgaggatc atccacgtgc aaggagtgat cctcgtaact    420
gacggcagga atgatgtaac gtggcaggac gaaccaaagg gatcgtgggt aacagctgag    480
accgtgatac ggcacgtgtc wtgtttgtgg atgaaaagaa gtgtgaaatg gcctatgcat    540
ggtctatagg ttacactaat ctgaccaaaa gcttctttta acctttttcct tttgtttctt    600
ctttcgctta taaccaagtg agaaactgta ttgtatttcc ctgaaaacat tagattaagt    660
atgagggatt acatatactt aaggcatctt taaccttagt ttatttatga taaagttagt    720
ttcagagtaa tatagcatta ttagctttga tggtttgtac aatagtgatg aatttggaca    780
tgaccataaa ctacaagaca cgagtggatt ctcataatat ttgcaccact aaggacaaaa    840
taactcatca tgctactttg ttgaaatata ttaccattat tattaatgta ttataaaaat    900
acgaacaagt tattattgaa ttgggtttac agctttcaag atatatttta tataaaaatg    960
aaaataaaaa caagaatttg tttacatata aaaagcaaac a                       1001
```

SEQ ID NO: 38    moltype = DNA  length = 1001
FEATURE          Location/Qualifiers
source           1..1001
                 mol_type = other DNA
                 organism = Brassica napus
SEQUENCE: 38
```
gatgaaaaga agtgtgaaat ggcctatgca tggtctatag gttacactaa tctgaccaaa    60
agcttctttt aacctttttcc ttttgtttct tctttcgctt ataaccaagt gagaaactgt    120
attgtatttc cctgaaaaca ttagattaag tatgagggat tacatatact taaggcatct    180
ttaaccttag tttatttatg ataaagttag tttcagagta atatagcatt attagctttg    240
atggtttgta caatagtgat gaatttggac atgaccataa actacaagac acgagtggat    300
tctcataata tttgcaccac taaggacaaa ataactcatc atgctacttt gttgaaatat    360
attaccatta ttattaatgt attataaaaa tacgaacaag ttattattga attgggttta    420
cagctttcaa gatatatttt atataaaaat gaaaataaaa acaagaattt gtttacatat    480
aaaaagcaaa cacgcatgta waataaattg gactgcatgt aaatcattgt tcaaattcat    540
```

-continued

```
tgtatttgtc gatggattaa ttaaatatct ttttgctata aaataaaatt ttatctttta  600
accaaaaaaa ataaaaaaaa taaaaaaaaa taaaattta tctatataaa ccattacata  660
gatgtccatc ccaatacgga catgcgctga acacaacaaa cgattctttt taagagaatc  720
tctctctctc tattctctcc acttctctct ctgtggatcg atggcagctt cggttgatcc  780
tttggtggtt ggaagagtga tcggagatgt gttggacatg ttcatcccca ccgccaacat  840
gtctgtctac tttggcccca aacacataac taacggctgc gagatcaaac cctctgccgc  900
agtcaaccct ccaaaagtca acatctccgg caactccaat gagctttaca ctctcgtata  960
catattaatc ttctcgcttc tatccatttt ttgtgctagc t                     1001
```

SEQ ID NO: 39　　　　　moltype = DNA　length = 685
FEATURE　　　　　　　　Location/Qualifiers
source　　　　　　　　 1..685
　　　　　　　　　　　 mol_type = other DNA
　　　　　　　　　　　 organism = Brassica napus
SEQUENCE: 39
```
tgtggatcga tggcagcttc ggttgatcct ttggtggttg gaagagtgat cggagatgtg  60
ttggacatgt tcatccccac cgccaacatg tctgtctact ttggccccaa acacataact  120
aacggctgcg agatcaaacc ctctgccgca gtcaaccctc caaaagtcaa catctccggc  180
aactccaatg agctttacac tctcgtgatg actacccggg acgcacctag cccgagtgag  240
ccgaacatga gagaatgggt ccattggatt gtcgtggata tcccgggagg caccaacccc  300
tcaaaaggaa aggagatact gccatatatg gagccgagac caccggtggg gattcaccgt  360
tacatatttg tacttttcag gcagaactca ccggtggtca tgatggtgca gcagccgcct  420
tcgcgagcca acttcagcac ccgaatgttc gctggacatc tcgatcttgg tttgcctgtg  480
gccacagttt acttcaacgc ccagaaagag ccagcttcac gcagacgctg atgcaygtca  540
accaaaataa aagagagagc cttttccggt tttacctaaa aaccgaccg gaaagaaata  600
tggggtttat atatcaaacc atattttgta tcatccggtt ctcgactata tatatgtgta  660
gatgcatata caattataca aatat                                       685
```

SEQ ID NO: 40　　　　　moltype = DNA　length = 1001
FEATURE　　　　　　　　Location/Qualifiers
source　　　　　　　　 1..1001
　　　　　　　　　　　 mol_type = other DNA
　　　　　　　　　　　 organism = Brassica napus
SEQUENCE: 40
```
atgatttatt atgtttcagg attgtcgtgg atatcccggg aggcaccaac ccctcaaaag  60
gtatgaaaat aaaagccaaa actaaatttt cgattttga atttttaattg tttcgctatt  120
ttccggaatc tcttaattat tattttttcta aactttttt acaaatgaat ttcacttttt  180
aactcacttt ctaactcact tgcttagata taaaataacg ttagtgtgaa agccactaag  240
aacacatgat aatggttaac tatgtccatg aagacgtgtt tgaatctaat tgaaaaatcc  300
gatacactag tatgtttttat tcatttaaac atattatctg tgcaacgtgg tgctttcggt  360
ttgatatgaa atggattccc cgtattgcac gatattgatt ggttcaacaa cacaaatatg  420
catgactctc acatgcatat aggtataaga gtcactatgt aattttcctt ggtttcaagt  480
tatgccccaa aataatacgt ratgtcttct aaaaccaaca ctaatgtat gtctgtacgt  540
gtacactgat gtatatcaac taaacaacg acacatgtct tcataaaaaa accttaaaca  600
tgacaaagca taagtgaata gaggatgata attattttat ttttattatt agtaccacgg  660
gaaactttga aatcgatata ctagcatgtt tttcattttta ggaaaggaga tactgccata  720
tatggagccg agaccaccgg tggggattca ccgttacata tttgtacttt tcaggcagaa  780
ctcaccggtg ggtatgatgg tgcagcagcc gccttcgcga gccaacttca gcacccgaat  840
gttcgctgga catctcgatc ttggtttgcc tgtggccaca gttacttca acgcccagaa  900
agagccagct tcacgcagac gctgatgcac gcaaccaaaa taaaagagag agccttttcc  960
ggttttacct aaaaaccgga ccggaaagaa atatgggggt t                     1001
```

SEQ ID NO: 41　　　　　moltype = DNA　length = 1001
FEATURE　　　　　　　　Location/Qualifiers
source　　　　　　　　 1..1001
　　　　　　　　　　　 mol_type = other DNA
　　　　　　　　　　　 organism = Brassica napus
SEQUENCE: 41
```
tgatttatta tgtttcagga ttgtcgtgga tatcccggga ggcaccaacc cctcaaaagg  60
tatgaaaata aaagccaaaa ctaaattttc gatttttgaa ttttaattgt ttcgctattt  120
tccggaatct cttaattatt attttttctaa acttttttta caaatgaatt tcactttta  180
actcactttc taactcactt gcttagatat aaaataacgt tagtgtgaaa gccactaaga  240
acacatgata atggttaact atgtccatga agacgtgttt gaatctaatt gaaaaatccg  300
atacactagt atgtttttatt catttaaaca tattatctgt gcaacgtggt gctttcggtt  360
tgatatgaaa tggattcccc gtattgcacg atattgattg gttcaacaac acaaatatgc  420
atgactctca catgcatata ggtataagag tcactatgta attttccttg gtttcaagtt  480
atgccccaaa ataatacgta rtgtcttcta aaaccaacat ctaatgtatg tctgtacgtg  540
tacactgatg tatatcaact aaacaacgga cacatgtct cataaaaaaa ccttaaacat  600
gacaaagcat aagtgaatag aggatgataa ttattttatt tttattatta gtaccacggg  660
aaactttgaa atcgatatac tagcatgttt ttcattttag gaaaggagat actgccatat  720
atggagccga ccaccggt ggggattcac cgttacatat ttgtacttt caggcagaac  780
tcaccggtgg gtatgatggt gcagcagccg ccttcgcgag ccaacttcag cacccgaatg  840
ttcgctggac atctcgatct tggtttgcct gtggccacac tttacttcaa cgcccagaaa  900
gagccagctt cacgcagacg ctgatgcacg caaccaaaat aaaagagaga gcctttccg  960
gttttaccta aaaaccggac cggaaagaaa tatggggttt a                     1001
```

SEQ ID NO: 42　　　　　moltype = DNA　length = 1001
FEATURE　　　　　　　　Location/Qualifiers
source　　　　　　　　 1..1001

```
                         mol_type = other DNA
                         organism = Brassica napus
SEQUENCE: 42
aggattgtcg tggatatccc gggaggcacc aacccctcaa aaggtatgaa aataaaagcc      60
aaaactaaat tttcgatttt tgaattttaa ttgtttcgct attttccgga atctcttaat     120
tattattttt ctaaactttt tttacaaatg aatttcactt tttaactcac tttctaactc     180
acttgcttag atataaaata acgttagtgt gaaagccact aagaacacat gataatggtt     240
aactatgtcc atgaagacgt gtttgaatct aattgaaaaa tccgatacac tagtatgttt     300
tattcattta aacatattat ctgtgcaacg tggtgctttc ggtttgatat gaaatggatt     360
ccccgtattg cacgatattg attggttcaa caacacaaat atgcatgact ctcacatgca     420
tataggtata agagtcacta tgtaattttc cttggtttca agttatgccc caaaataata     480
cgtaatgtct ctaaaacca rcatctaatg tatgtctgta cgtgtacact gatgtgtatc     540
aactaaacaa cggacacatg tcttcataaa aaaaccttaa acatgacaaa gcataagtga     600
atagaggatg ataattattt tatttttatt attagtacca cgggaaactt tgaaatcgat     660
atactagcat gttttttcatt ttaggaaagg agatactgcc atatatggag ccgagaccac     720
cggtgggggat tcaccgttac atatttgtac ttttcaggca gaactcaccg gtgggtatga     780
tggtgcagca gccgccttcg cgagccaact tcagcacccg aatgttcgct ggacatctcg     840
atcttggttt gcctgtggcc acagtttact tcaacgccca gaaagagcca gcttcacgca     900
gacgctgatg cacgcaacca aaataaaaga gagagccttt tccggtttta cctaaaaacc     960
ggaccggaaa gaaatatggg gtttatatat caaaccatat t                       1001

SEQ ID NO: 43          moltype = DNA   length = 1001
FEATURE                Location/Qualifiers
source                 1..1001
                       mol_type = other DNA
                       organism = Brassica napus
SEQUENCE: 43
ttgtttcgct attttccgga atctcttaat tattattttt ctaaactttt tttacaaatg      60
aatttcactt tttaactcac tttctaactc acttgcttag atataaaata acgttagtgt     120
gaaagccact aagaacacat gataatggtt aactatgtcc atgaagacgt gtttgaatct     180
aattgaaaaa tccgatacac tagtatgttt tattcattta aacatattat ctgtgcaacg     240
tggtgctttc ggtttgatat gaaatggatt ccccgtattg cacgatattg attggttcaa     300
caacacaaat atgcatgact ctcacatgca tataggtata agagtcacta tgtaattttc     360
cttggtttca agttatgccc caaaataata cgtaatgtct ctaaaacca acatctaatg     420
tatgtctgta cgtgtacact gatgtgtatc aactaaacaa cggacacatg tcttcataaa     480
aaaaccttaa acatgacaaa rcataagtga atagaggatg ataattattt tatttttatt     540
attagtacca cgggaaactt tgaaatcgat atactagcat gttttttcatt ttaggaaagg     600
agatactgcc atatatggag ccgagaccac cggtgggggat tcaccgttac atatttgtac     660
ttttcaggca gaactcaccg gtgggtatga tggtgcagca gccgccttcg cgagccaact     720
tcagcacccg aatgttcgct ggacatctcg atcttggttt gcctgtggcc acagtttact     780
tcaacgccca gaaagagcca gcttcacgca gacgctgatg cacgcaacca aaataaaaga     840
gagagccttt tccggtttta cctaaaaacc ggaccggaaa gaaatatggg gtttatatat     900
caaaccatat tttgtatcat ccggttctcg actatatata tgtgtagatg catatacaat     960
tatacaaata tgtttatgtt tgtgtgttat attaagtggc t                       1001

SEQ ID NO: 44          moltype = DNA   length = 1001
FEATURE                Location/Qualifiers
source                 1..1001
                       mol_type = other DNA
                       organism = Brassica napus
SEQUENCE: 44
tacaaatgaa tttcactttt taactcactt tctaactcac ttgcttagat ataaaataac      60
gttagtgtga aagccactaa gaacacatga taatggttaa ctatgtccat gaagacgtgt     120
ttgaatctaa ttgaaaaatc cgatacacta gtatgtttta ttcatttaaa catattatct     180
gtgcaacgtg gtgctttcgg tttgatatga aatggattcc ccgtattgcg cgatattgat     240
tggttcaaca acacaaatat gcatgactct cacatgcata taggtataag agtcactatg     300
taattttcct tggtttcaag ttatgcccca aaataatacg taatgtcttc taaaaccaac     360
atctaatgta tgtctgtacg tgtacactga tgtatatcaa ctaaacaacg gacacatgtc     420
ttcataaaaa aaccttaaac atgacaaagc ataagtgaat agaggatgaa aattatttta     480
ttttttattat tagtaccacg rgaaactttg aaatcgatat actacatgt ttttcatttt     540
aggaaaggag atactgccat atatggagcc gagaccaccg gtgggggattc accgttacat     600
atttgtactt tcaggcaga actcaccggt gggtatgatg gtgcagcagc cgccttcgcg     660
agccaacttc agcacccgaa tgttcgctgg acatctcgat cttggtttgc ctgtggccac     720
agtttacttc aacgcccaga aagagccagc ttcacgcaga cgctgatgca cgcaaccaaa     780
ataaaagaga gagccttttc cggttttacc taaaaaccgg accggaaaga aatatggggt     840
ttatatatca aaccatattt gtatcatcc ggttctcgac tatatatatg tgtagatgca     900
tatacaatta tacaaatatg tttatgtttg tgtgttatat taagtggctt gcgtataata     960
tatggttttc gttttctttt atctttaaat aaactaaaaa a                       1001

SEQ ID NO: 45          moltype = DNA   length = 1002
FEATURE                Location/Qualifiers
variation              502
                       note = where n is an insertion/deletion [+/T]
source                 1..1002
                       mol_type = other DNA
                       organism = Brassica napus
SEQUENCE: 45
cgcccagaaa gagccagctt cacgcagacg ctgatgcacg caaccaaaat aaaagagaga      60
gcctttccg gttttaccta aaaaccggac cggaaagaaa tatgggggttt atatatcaaa     120
```

-continued

```
ccatattttg tatcatccgg ttctcgacta tatatatgtg tagatgcata tacaattata   180
caaatatgtt tatgtttgtg tgttatatta agtggcttgc gtataatata tggttttcgt   240
tttcttttat ctttaaataa actaaaaaat aaaggtatgt atcaaattat aaagaaacaa   300
gaagagagga taaacaaaaa aaatgaaaat tctagtatac tgccttatta aaaaaaaaaa   360
atactattag ttcttaaacc gaaattcaga aatataaatg tcggttacaa atttgattcg   420
aacaaaatga accatttccc gtttaaataa actagtttca accaccacat ttaagttaaa   480
atatatcata ttattaattt tnaacccaaa actcaagaat acaaatgtca gttacaagct   540
taattccaac aaaatgattt aattctaact taaataaact agcttgcttg accgccggct   600
gacttaaata aactagcttt tcttgttgat cattagcctt cttctcctct gaacctatgt   660
agcttgtttt ctaaagattt tgatccacgc actctccttg aatttcaact acatcttctg   720
tggactcata tctttccttc tctctattct cagagtcttg ttttattcca gaatcatcaa   780
agcttggaca aatcgaatgt aacttcacgt tgatccactg aaaaatcttg ttcgtaagag   840
tttggtgttg aagtaacatc tagtgcttcg ccattggttt cttagagcat gattattgca   900
aagacccata ttaggggttc ttattatttt ttaatgcttt taagtacaaa aagtgattta   960
agagacaaat ttaagaaacc ctaacattta attgctccat tg                     1002
```

SEQ ID NO: 46  moltype = DNA length = 1001
FEATURE    Location/Qualifiers
source     1..1001
       mol_type = other DNA
       organism = Brassica napus
SEQUENCE: 46

```
agagcctttt ccggttttac ctaaaaaccg gaccggaaag aaatatgggg tttatatatc   60
aaaccatatt ttgtatcatc cggttctcga ctatatatat gtgtagatgc atatacaatt   120
atacaaatat gtttatgttt gtgtgttata ttaagtggct tgcgtataat atatggtttt   180
cgtttctctt tatctttaaa taaactaaaa aataaaggta tgtatcaaat tataaagaaa   240
caagaagaga ggataaacaa aaaaaaatgaa aattctagta tactgcctta ttaaaaaaaa   300
aaaatactat tagttcttaa accgaaattc agaaatataa atgtcggtta caaatttgat   360
tcgaacaaaa tgaaccattt cccgtttaaa taaactagtt caaccacca catttaagtt   420
aaaatatatc atattattaa ttttaaccca aactcaagaa tacaaatgt cagttacaag   480
cttaattcca acaaaatgat ytaattctaa cttaaataaa ctagcttgct tgaccgccgg   540
ctgacttaaa taaactagct tttcttgttg atcattagcc ttcttctcct ctgaacctat   600
gtagcttgtt ttctaaagat tttgatccac gcactctcct tgaatttcaa ctacatcttc   660
tgtggactca tatctttcct tctctctatt ctcagagtct tgttttattc cagaatcatc   720
aaagcttgga caaatcgaat gtaacttcac gttgatccac tgaaaaatct tgttcgtaag   780
agtttggtgt tgaagtaaca tctagtgctt cgccattggt ttcttagagc atgattattg   840
caaagaccca ttaggggt tcttattatt ttttaatgct tttaagtaca aaaagtgatt   900
taagagacaa atttaagaaa ccctaacatt taattgctcc attgcaaggt tcttacaaca   960
ttactttcac tcttcttact tgatcttctt tagccaatgt t                      1001
```

SEQ ID NO: 47  moltype = DNA length = 1001
FEATURE    Location/Qualifiers
source     1..1001
       mol_type = other DNA
       organism = Brassica napus
SEQUENCE: 47

```
atatggggtt tatatatcaa accatatttt gtatcatccg gttctcgact atatatatgt   60
gtagatgcat atacaattat acaaatatgt ttatgtttgt gtgttatatt aagtggcttg   120
cgtataatat atggttttcg ttttctttta tctttaaata aactaaaaaa taaaggtatg   180
tatcaaatta taaagaaaca agaagagagg ataaacaaaa aaaatgaaaa ttctagtata   240
ctgccttatt aaaaaaaaaa atactatta gttcttaaac cgaaattcag aaatataaat   300
gtcggttaca aatttgattc gaacaaaatg aaccatttcc cgtttaaata aactagtttc   360
aaccaccaca tttaagttaa aatatatcat attattaatt ttaacccaaa actcaagaat   420
acaaatgtca gttacaagct taattccaac aaaatgattt aattctaact taaataaact   480
agcttgcttg accgccggct racttaaata aactagcttt tcttgttgat cattagcctt   540
cttctcctct gaacctatgt agcttgtttt ctaaagattt tgatccacgc actctccttg   600
aatttcaact acatcttctg tggactcata tctttccttc tctctattct cagagtcttg   660
ttttattcca gaatcatcaa agcttggaca aatcgaatgt aacttcacgt tgatccactg   720
aaaaatcttg ttcgtaagag tttggtgttg aagtaacatc tagtgcttcg ccattggttt   780
cttagagcat gattattgca aagacccata ttaggggttc ttattatttt ttaatgcttt   840
taagtacaaa aagtgattta agagacaaat ttaagaaacc ctaacattta attgctccat   900
tgcaaggttc ttacaacatt actttcactc ttcttacttg atcttcttta gccaatgttg   960
ttccaatgtc aaagacgatg aaacagaaac aagaaaacct c                      1001
```

SEQ ID NO: 48  moltype = DNA length = 1001
FEATURE    Location/Qualifiers
source     1..1001
       mol_type = other DNA
       organism = Brassica napus
SEQUENCE: 48

```
taatatatgg ttttcgtttt cttttatctt taaataaact aaaaaataaa ggtatgtatc   60
aaattataaa gaaacaagaa gagaggataa acaaaaaaaa tgaaaattct agtatactgc   120
cttattaaaa aaaaaaata ctattagttc ttaaaccgaa attcagaaat ataaatgtcg   180
gttacaaatt tgattcgaac aaaatgaacc atttcccgtt taaataaact agtttcaacc   240
accacattta agttaaaata tcatatta ttaattttaa cccaaaactc aagaatacaa   300
atgtcagtta caagcttaat tccaacaaaa tgatttaatt ctaacttaaa taaactagct   360
tgcttgaccg ccggctgact aaataaact agcttttctt gttgatcatt agccttcttc   420
tcctctgaac ctatgtagct tgttttctaa agattttgat ccacgcactc tccttgaatt   480
tcaactacat cttctgtgga ytcatatctt tccttctctc tattctcaga gtcttgtttt   540
```

-continued

```
attccagaat catcaaagct tggacaaatc gaatgtaact tcacgttgat ccactgaaaa    600
atcttgttcg taagagtttg gtgttgaagt aacatctagt gcttcgccat tggtttctta    660
gagcatgatt attgcaaaga cccatattag gggttcttat tatttttttaa tgctttttaag    720
tacaaaaagt gatttaagag acaaatttaa gaaaccctaa catttaattg ctccattgca    780
aggttcttac aacattactt tcactcttct tacttgatct tctttagcca atgttgttcc    840
aatgtcaaag acgatgaaac agaaacaaga aaacctcaat aaaatgaatc aataaccaga    900
accttgaaac atgaaacaaa acaacaaagc atatcattct cattactcaa acagaacaag    960
aacattaaca tgaaacagag acagaataag caaaacaacg t                       1001

SEQ ID NO: 49          moltype = DNA  length = 1001
FEATURE                Location/Qualifiers
source                 1..1001
                       mol_type = other DNA
                       organism = Brassica napus
SEQUENCE: 49
ataaagaaac aagaagagag gataaacaaa aaaaatgaaa attctagtat actgccttat    60
taaaaaaaaa aaatactatt agttcttaaa ccgaaattca gaaatataaa tgtcggttac    120
aaatttgatt cgaacaaaat gaaccatttc ccgtttaaat aaactagttt caaccaccac    180
atttaagtta aaatatatca tattattaat tttaacccaa aactcaagaa tacaaatgtc    240
agttacaagc ttaattccaa caaaatgatt taattctaac ttaaataaac tagcttgctt    300
gaccgccggc tgacttaaat aaactagctt ttcttgttga tcattagcct tcttctcctc    360
tgaacctatg tagcttgttt tctaaagatt ttgatccacg cactctcctt gaatttcaac    420
tacatcttct gtggactcat atctttcctt ctctctattc tcagagtctt gttttattcc    480
agaatcatca aagcttggac raatcgaatg taacttcacg ttgatccact gaaaaatctt    540
gttcgtaaga gtttggtgtt gaagtaacat ctagtgcttc gccattggtt tcttagagca    600
tgattattgc aaagacccat attaggggtt cttattattt tttaatgctt ttaagtacaa    660
aaagtgattt aagagacaaa tttaagaaac cctaacattt aattgctcca ttgcaaggtt    720
cttacaacat tactttcact cttcttactt gatcttcttt agccaatgtt gttccaatgt    780
caaagacgat gaaacagaaa caagaaaacc tcaataaaat gaatcaataa ccagaacctt    840
gaaacatgaa acaaaacaac aaagcatatc attctcatta ctcaaacaga acaagaacat    900
taacatgaaa cagagacaga ataagcaaaa caacgtgtag ttccccgtac gtcttgtgca    960
gcattgtaat tcttcacgga atcagtagta aaagttattc a                       1001

SEQ ID NO: 50          moltype = DNA  length = 1001
FEATURE                Location/Qualifiers
source                 1..1001
                       mol_type = other DNA
                       organism = Brassica napus
SEQUENCE: 50
attaaaaaaa aaaaatacta ttagttctta aaccgaaatt cagaaatata aatgtcggtt    60
acaaatttga ttcgaacaaa atgaaccatt tcccgtttaa ataaactagt ttcaaccacc    120
acatttaagt taaaatatat catattatta attttaaccc aaaactcaag aatacaaatg    180
tcagttacaa gcttaattcc aacaaaatga tttaattcta acttaaataa actagcttgc    240
ttgaccgccg gctgacttaa ataaactagc ttttcttgtt gatcattagc cttcttctcc    300
tctgaaccta tgtagcttgt tttctaaaga ttttgatcca cgcactctcc ttgaatttca    360
actacatctt ctgtggactc atatctttcc ttctctctat tctcagagtc ttgtttttatt    420
ccagaatcat caaagcttgg acaaatcgaa tgtaacttca cgttgatcca ctgaaaaatc    480
ttgttcgtaa gagtttggtg ytgaagtaac atctagtgct tcgccattgg tttcttagag    540
catgattatt gcaaagaccc atattagggg ttcttattat tttttaatgc ttttaagtac    600
aaaaagtgat ttaagagaca aatttaagaa accctaacat ttaattgctc cattgcaagg    660
ttcttacaac attactttca ctcttcttac ttgatcttct tagccaatgt tgttccaat    720
gtcaaagacg atgaaacaga aacaagaaaa cctcaataaa atgaatcaat aaccagaacc    780
ttgaaacatg aaacaaaaca aaagcata tcattctcat tactcaaaca gaacaagaac    840
attaacatga aacagagaca gaataagcaa acaacgtgt agttccccgt acgtcttgtg    900
cagcattgta attcttcacg gaatcagtag taaaagttat ttattaaacc gttctaacag    960
tagtaaacaa acatccaggt gctgtgaaaa aaatctatca a                       1001

SEQ ID NO: 51          moltype = DNA  length = 1001
FEATURE                Location/Qualifiers
source                 1..1001
                       mol_type = other DNA
                       organism = Brassica napus
SEQUENCE: 51
tactattagt tcttaaaccg aaattcagaa atataaatgt cggttacaaa tttgattcga    60
acaaaatgaa ccatttcccg tttaaataaa ctagtttcaa ccaccacatt taagttaaaa    120
tatatcatat tattaattt aacccaaaac tcaagaatac aaatgtcagt tacaagctta    180
attccaacaa aatgatttaa ttctaactta ataaaactag cttgcttgac cgccggctga    240
cttaaataaa ctagcttttc ttgttgatca ttagccttct tctcctctga acctatgtag    300
cttgtttttct aaagattttg atccacgcac tctccttgaa tttcaactac atctctgtg    360
gactcatatc tttccttctc tctattctca gagtcttgtt ttattccaga atcatcaaag    420
cttggacaaa tcgaatgtaa cttcacgttg atccactgaa aaatcttgtt cgtaagagtt    480
tggtgttgaa gtaacatcta stgcttcgcc attggtttct tagagcatga ttattgcaaa    540
gacccatatt aggggttctt attattttt aatgctttta agtacaaaaa gtgatttaag    600
agacaaattt aagaaaccct aacatttaat tgctccattg caaggttctt acaacattac    660
tttcactctt cttacttgat cttcttttagc caatgttgtt ccaatgtcaa agacgatgaa    720
acagaaacaa gaaaacctca ataaaatgaa tcaataacca gaaccttgaa acatgaaaca    780
aaacaacaaa gcatatcatt ctcattactc aaacagaaca gaacattaa catgaaacag    840
agacagaata agcaaaacaa cgtgtagttc ccgtacgtt tgtgcagca ttgtaattct    900
tcacggaatc agtagtaaaa gttatttatt aaaccgttct aacagtagta aacaaacatc    960
```

```
caggtgctgt gaaaaaaatc tatcaattga aacaacgatc t                      1001

SEQ ID NO: 52          moltype = DNA   length = 1002
FEATURE                Location/Qualifiers
variation              502
                       note = where n is an insertion/deletion [+/A]
source                 1..1002
                       mol_type = other DNA
                       organism = Brassica napus
SEQUENCE: 52
tggtggaaga agaagactca gctttgttgt tgttgcagag ataaccgcgg ctcagaggta   60
aggacgaaga agaatgcgac agctgtctca taagagacgt cccttgcgga gccaaattaa   120
gagacgtctt ctccgtgttt tgtattttc attttttttt aatcacaata acctaagaga   180
catgcttagg agactgcgat aatggtgctc ttacagaccc cacgacagga gggcttgttc   240
actgtattct aattggtgga aaagaaagct acgggaaaga aatactcttg tgagcacata   300
tgttgttgtt caattctaag ggcagaaacg agttgctaga gttccatttt aaccagtttc   360
tgtacacctt taaacattgt aattgttgca tacacgccag cttattaaga aaatacaaat   420
tcaagtgtga ctactctgtt ccctcatttt gataggatta tcaaagatat cacattgaaa   480
caaaacagaa gcaactaaaa ancagtaaga tctctcacaa acaatataaa agatcgaaac   540
ctagaattga cataaaacaa aacattattg caaaatctca gtttgttgac aaaacaaaag   600
tgtgatagat aaaaaacaca tccaaggaga gagacagggc aaagagatgg gataaactag   660
taacggccaa taccccaaac tctgataact ccatcggtgt atccactgaa caaggtgctt   720
ccatccgcac tccagctcag gctagtgcag taaataacct gtccaaaaaa gtaaatgttt   780
aagtctagtt tctcaatcta ggcaagaaaa aaaacagtt cttaccaaaa tataaaaaca   840
ttcaaaaatt gccatagata gaaaaatcta tatcagatct atcgattaca ttcacatatt   900
gataaaacac tagccaacaa tatactgcaa tctatggcaa acatgtataa aagtaaattc   960
agacaaaaga acacaagaca tttgagcatc cacatgaaaa ac                     1002

SEQ ID NO: 53          moltype = DNA   length = 1001
FEATURE                Location/Qualifiers
source                 1..1001
                       mol_type = other DNA
                       organism = Brassica napus
SEQUENCE: 53
gttgttgttg cagagataac cgcggctcag aggtaaggac gaagaagaat gcgacagctg   60
tctcataaga gacgtccctt gcggagccaa attaagagac gtcttctccg tgttttgtat   120
ttttcatttt tttttaatca caataaccta agagacatgc ttaggagact gcgataatgg   180
tgctcttaca gaccccacga caggagggct tgttcactgt attctaattg gtggaaaaga   240
aagctacgtg gg aaagaaatac tcttgtgagc acatatgtt ttgttcaatt ctaagggcag   300
aaacgagttg ctagagttcc attttaacca gtttctgtac accttaaac attgtaattg   360
ttgcatacac gccagcttat taagaaaata caaattcaag tgtgactact ctgttccctc   420
attttgatag gattatcaaa gatatcacat tgaaacaaaa cagaagcaac taaaaacagt   480
aagatctctc acaaacaata waaagatcg aaacctgaaa ttgacataaa acaaaacatt   540
attgcaaaat ctcagtttgt tgacaaaaca aaagtgtgat agataaaaaa cacatccaag   600
gagagagaca gggcaaagag atgggataaa ctagtaacgg ccaataccc aaactctgat   660
aactccatcg gtgtatccac tgaacaaggt gcttccatcc gcactccagc tcaggctagt   720
gcagtaaata acctgtccaa aaaagtaaat gtttaagtc agtttctcaa tctaggcaag   780
aaaaaaaaac agttcttacc aaaatataaa aacattcaaa aattgccata gatagaaaaa   840
tctatatcag atctatcgat tacattcaca tattgataaa acactagcca acaatatact   900
gcaatctatg gcaaacatgt ataaaagtaa attcagacaa aagaacacaa gacatttgag   960
catccacatg aaaaacaaac atatttacaa aacataaaca a                      1001

SEQ ID NO: 54          moltype = DNA   length = 1001
FEATURE                Location/Qualifiers
source                 1..1001
                       mol_type = other DNA
                       organism = Brassica napus
SEQUENCE: 54
agagacgtct tctccgtgtt ttgtattttt catttttttt taatcacaat aacctaagag   60
acatgcttag gagactgcga taatggtgct cttacagacc ccacgacagg agggcttgtt   120
cactgtattc taattggtgg aaaagaaagc tacgggaaag aaatactctt gtgagcacat   180
atgttgttgt tcaattctaa gggcagaaac gagttgctag agttccattt taaccagttt   240
ctgtacacct ttaaacattg taattgttgc atacacgcca gcttattaag aaaatacaaa   300
ttcaagtgtg actactctgt tccctcattt tgataggatt atcaaagata tcacattgaa   360
acaaaacaga agcaactaaa aacagtaaga tctctcacaa acaatataaa agatcgaaac   420
ctagaattga cataaaacaa aacattattg caaaatctca gtttgttgac aaaacaaaag   480
tgtgatagat aaaaaacaca wccaaggaga gagacagggc aaagagatgg gataaactag   540
taacggccaa taccccaaac tctgataact ccatcggtgt atccactgaa caaggtgctt   600
ccatccgcac tccagctcag gctagtgcag taaataacct gtccaaaaaa gtaaatgttt   660
aagtctagtt tctcaatcta ggcaagaaaa aaaacagtt cttaccaaaa tataaaaaca   720
ttcaaaaatt gccatagata gaaaaatcta tatcagatct atcgattaca ttcacatatt   780
gataaaacac tagccaacaa tatactgcaa tctatggcaa acatgtataa aagtaaattc   840
agacaaaaga acacaagaca tttgagcatc cacatgaaaa acaaacatat ttacaaaaca   900
taaacaagga tataaaacca aatcataac cataagcatg catcgtttat ttgcatttca   960
atagatcaat ccaaagaac catttctata aacactatcc t                       1001

SEQ ID NO: 55          moltype = DNA   length = 1001
FEATURE                Location/Qualifiers
source                 1..1001
```

```
                          mol_type = other DNA
                          organism = Brassica napus
SEQUENCE: 55
gataatggtg ctcttacaga cccccacgaca ggagggcttg ttcactgtat tctaattggt    60
ggaaaagaaa gctacgggaa agaaatactc ttgtgtgcac atatgttgtt gttcaattct   120
aagggcagaa acgagttgct agagttccat tttaaccagt ttctgtacac cttttaaacat   180
tgtaattgtt gcatacacgc cagcttatta agaaaataca aattcaagtg tgactactct   240
gttccctcat tttgatagga ttatcaaaga tatcacattg aaacaaaaca gaagcaacta   300
aaaacagtaa gatctctcac aaacaatata aaagatcgaa acctagaatt gacataaaac   360
aaaacattat tgcaaaatct cagtttgttg acaaaacaaa agtgtgatag ataaaaaaca   420
catccaagga gagagacagg gcaaagagat gggataaaact agtaacggcc aatacccccaa   480
actctgataa ctccatcggt rtatccactg aacaaggtgc ttccatccgc actccagctc   540
aggctagtgc agtaaataac ctgtccaaaa aagtaaatgt ttaagtctag tttctcaatc   600
taggcaagaa aaaaaaacag ttcttaccaa aatataaaa cattcaaaaa ttgccataga   660
tagaaaaatc tatatcagat ctatcgatta cattcacata ttgataaaac actagccaac   720
aatatactgc aatctatggc aaacatgtat aaaagtaaat tcagacaaaa gaacacaaga   780
catttgagca tccacatgaa aaacaaacat atttacaaaa cataaacaag gatataaaac   840
cacaatcata accataagca tgcatcgttt atttgcattt caagaatatca atccaaaaga   900
accatttcta taaacactat cctctatcaa cagtttacct aaaactaaaga aatattatcc   960
atacaataag catcaaactt gcatgtcttt gtacctttct t                       1001

SEQ ID NO: 56          moltype = DNA   length = 1001
FEATURE                Location/Qualifiers
source                 1..1001
                       mol_type = other DNA
                       organism = Brassica napus
SEQUENCE: 56
tgtattctaa ttggtggaaa agaaagctac gggaaagaaa tactcttgtg agcacatatg    60
ttgttgttca attctaaggg cagaaacgag ttgctagagt tccattttaa ccagtttctg   120
tacacctttta aacattgtaa ttgttgcata cacgccagct tattaagaaa atacaaattc   180
aagtgtgact actctgttcc ctcattttga taggattatc aaagatatca cattgaaaca   240
aaacagaagc aactaaaaac agtaagatct ctcacaaaca atataaaaga tcgaaaccta   300
gaattgacat aaaacaaaac attattgcaa aatctcagtt tgttgacaaa acaaaagtgt   360
gatagataaa aaacacatcc aaggagagag acagggcaaaa gagatgggat aaactagtaa   420
cggccaatac cccaaactct gataactcca tcggtgtatc cactgaacaa ggtgcttcca   480
tccgcactcc agctcaggct rgtgcagtaa ataacctgtc caaaaaagta aatgtttaag   540
tctagtttct caatctaggc aagaaaaaaa aacagttctt accaaaatat aaaaacattc   600
aaaaattgcc atagatagaa aaatctatat cagatctatc gattacattc acatattgat   660
aaaacactag ccaacaatat actgcaatct atggcaataa tgtataaaag taattcaga   720
caaaagaaca caagacattt gagcatccac atgaaaaaca aacatattta caaaacataa   780
acaaggatat aaaaccacaa tcataaccat aagcatgcat cgtttatttg catttcaata   840
gatcaatcca aagaaccat ttctataaac actatcctct atcaacagtt tacctaaact   900
aaagaaatat tatccataca ataagcatca aacttgcatg tctttgtacc tttctttggg   960
tggcagcagt accattcca tcggacttct cagcctcagc c                        1001

SEQ ID NO: 57          moltype = DNA   length = 1001
FEATURE                Location/Qualifiers
source                 1..1001
                       mol_type = other DNA
                       organism = Brassica napus
SEQUENCE: 57
gggcagaaac gagttgctag agttccattt taaccagttt ctgtacacct ttaaacattg    60
taattgttgc atacacgcca gcttattaag aaaatacaaa ttcaagtgtg actactctgt   120
tccctcattt tgataggatt atcaaagata tcacattgaa acaaaacaga agcaactaaa   180
aacagtaaga tctctcacaa acaatataaa agatcgaa ctagaattg acaaaaacaa   240
aacattattg caaaatctca gtttgttgac aaaacaaaag tgtgatagat aaaaaacaca   300
tccaaggaga gagacagggc aaagagatgg gataaactag taacggccaa tacccccaaac   360
tctgataact ccatcggtgt atccactgaa caaggtgctt ccatccgcac tccagctcag   420
gctagtgcag taaataacct gtccaaaaaa gtaaatgttt aagtctagt tctcaatcta   480
ggcaagaaa aaaaacagtt sttaccaaaa tataaaaaca ttcaaaaatt gccatagata   540
gaaaaatcta tatcagatct atcgattaca ttcacatatt gataaaacac tagccaacaa   600
tatactgcaa tctatggcaa acatgtataa aagtaaattc agacaaaaga acacaagaca   660
tttgagcatc cacatgaaaa acaaacatat ttacaaaaca taaacaagga tataaaacca   720
caatcataac cataagcatg catcgtttat ttgcatttca atagatcaat ccaaaagaac   780
catttctata aacactatcc tctatcaaca gtttacctaa actaaagaaa tattatccat   840
acaataagca tcaaacttgc atgtctttgt acctttcttt tggtggcagc agtaccactt   900
ccatcggact tctcagcctc agccttgaga tcaaccttca agtcctcaac aacactcttg   960
ctctcaagat cccaaatctt aatacccctgc tcagtcgcag c                      1001

SEQ ID NO: 58          moltype = DNA   length = 1001
FEATURE                Location/Qualifiers
source                 1..1001
                       mol_type = other DNA
                       organism = Brassica napus
SEQUENCE: 58
agaaacgagt tgctagagtt ccattttaac cagtttctgt acacctttaa acattgtaat    60
tgttgcatac acgccagctt attaagaaaa tacaaattca agtgtgacta ctctgttccc   120
tcattttgat aggattatca aagatatcac attgaaacaa aacagaagca actaaaaaca   180
gtaagatctc tcacaaacaa tataaaagat cgaaacctag aattgacata aaacaaaaca   240
```

```
ttattgcaaa atctcagttt gttgacaaaa caaaagtgtg atagataaaa aacacatcca  300
aggagagaga cagggcaaag agatgggata aactagtaac ggccaatacc ccaaactctg  360
ataactccat cggtgtatcc actgaacaag gtgcttccat ccgcactcca gctcaggcta  420
gtgcagtaaa taacctgtcc aaaaaagtaa atgtttaagt ctagtttctc aatctaggca  480
agaaaaaaaa acagttctta mcaaaatata aaaacattca aaaattgcca tagatagaaa  540
aatctatatc agatctatcg attacattca catattgata aaacactagc caacaatata  600
ctgcaatcta tggcaaacat gtataaaagt aaattcagac aaaagaacac aagacatttg  660
agcatccaca tgaaaaacaa acatatttac aaaacataaa caaggatata aaaccacaat  720
cataaccata agcatgcatc gtttatttgc atttcaatag atcaatccaa aagaaccatt  780
tctataaaca ctatcctcta tcaacagttt acctaaacta aagaaatatt atccatacaa  840
taagcatcaa acttgcatgt ctttgtacct ttcttttggt ggcagcagta ccacttccat  900
cggacttctc agcctcagcc ttgagatcaa ccttcaagtc ctcaacaaca ctcttgctct  960
caagatccca aatcttaata ccctgctcag tcgcagcaca a                      1001
```

SEQ ID NO: 59          moltype = DNA   length = 1001
FEATURE                Location/Qualifiers
source                 1..1001
                       mol_type = other DNA
                       organism = Brassica napus SEQUENCE: 59
```
gagttgctag agttccattt taaccagttt ctgtacacct ttaaacattg taattgttgc  60
atacacgcca gcttattaag aaaatacaaa ttcaagtgtg actactctgt tccctcattt  120
tgataggatt atcaaagata tcacattgaa acaaaacaga agcaactaaa aacagtaaga  180
tctctcacaa acaatataaa agatcgaaac ctagaattga cataaaacaa aacattattg  240
caaaatctca gtttgttgac aaaacaaaag tgtgatagat aaaaaacaca tccaaggaga  300
gagacagggc aaagagatgg gataaactag taacggccaa taccccaaac tctgataact  360
ccatcggtgt atccactgaa caaggtgctt ccatccgcac tccagctcag gctagtgcag  420
taaataacct gtccaaaaaa gtaaatgttt aagtctagtt tctcaatcta ggcaagaaaa  480
aaaaacagtt cttaccaaaa yataaaaaca ttcaaaaatt gccatagata gaaaaatcta  540
tatcagatct atcgattaca ttcacatatt gataaaacac tagccaacaa tatactgcaa  600
tctatggcaa acatgtataa aagtaaaatc agacaaaaga acacaagaca tttgagcatc  660
cacatgaaaa acaaacatat ttacaaaaca taaacaagga tataaaacca caatcataac  720
cataagcatg catcgtttat ttgcatttca atagatcaat ccaaaagaac catttctata  780
aacactatcc tctatcaaca gtttacctaa actaaagaaa tattatccat acaataagca  840
tcaaacttgc atgtctttgt acctttcttt tggtggcagc agtaccactt ccatcggact  900
tctcagcctc agccttgaga tcaaccttca agtcctcaac aacactcttg ctctcaagat  960
cccaaatctt ataccctgc tcagtcgcag cacaaagcca g                       1001
```

SEQ ID NO: 60          moltype = DNA   length = 1001
FEATURE                Location/Qualifiers
source                 1..1001
                       mol_type = other DNA
                       organism = Brassica napus SEQUENCE: 60
```
cacattgaaa caaaacagaa gcaactaaaa acagtaagat ctctcacaaa caatataaaa  60
gatcgaaacc tagaattgac ataaaacaaa acattattgc aaaatctcag tttgttgaca  120
aaacaaaagt gtgatagata aaaaacacat ccaaggagag agacagggca aagagatggg  180
ataaactagt aacggccaat accccaaact ctgataactc catcggtgta tccactgaac  240
aaggtgcttc catccgcact ccagctcagg ctagtgcagt aaataacctg tccaaaaaag  300
taaatgttta agtctagttt ctcaatctag gcaagaaaaa aaaacagttc ttaccaaaat  360
ataaaaacat tcaaaaattg ccatagatag aaaaatctat atcagatctc tcgattacat  420
tcacatattg ataaaacact agccaacaat atactgcaat ctatggcaaa catgtataaa  480
agtaaaattca gacaaaagaa sacaagacat ttgagcatcc acatgaaaaa caaacatatt  540
tacaaaacat aaacaaggat ataaaaccac aatcataacc ataagcatgc atcgtttatt  600
tgcatttcaa tagatcaatc caaaagaacc atttctataa acactatcct ctatcaacag  660
tttacctaaa ctaaagaaat attatccata caataagcat caaacttgca tgtctttgta  720
cctttctttt ggtggcagca gtaccacttc catcggactt ctcagcctca gccttgagat  780
caaccttcaa gtcctcaaca acactcttgc tctcaagatc ccaaatctta ataccctgct  840
cagtcgcagc acaaagccag tacctattag gactaaagca aagagcgtga atcacagagt  900
tggcttcaag agagtaaagc ttcttcccct cagccaaatc ccagagcaaa acgacaccgt  960
ctttgcctcc actagcacac agagaaccat caggcgacac a                      1001
```

SEQ ID NO: 61          moltype = DNA   length = 1001
FEATURE                Location/Qualifiers
source                 1..1001
                       mol_type = other DNA
                       organism = Brassica napus SEQUENCE: 61
```
cattgaaaca aaacagaagc aactaaaaac agtaagatct ctcacaaaca atataaaaga  60
tcgaaaccta gaattgacat aaaacaaaac attattgcaa aatctcagtt tgttgacaaa  120
acaaaagtgt gatagataaa aaacacatcc aaggagagag acaggcaaa gagatgggat  180
aaactagtaa cggccaatac cccaaactct gataactcca tcggtgtatc cactgaacaa  240
ggtgcttcca tccgcactcc agctcaggct agtgcagtaa ataacctgtc caaaaaagta  300
aatgtttaag tctagtttct caatctaggc aagaaaaaaa aaacagttctt accaaaatat  360
aaaaacattc aaaaattgcc atagataaaa aatctatat cagatctatc gattacattc  420
acatattgat aaaacactag ccaacaatat actgcaatct atggcaaaca tgtataaaag  480
taaattcaga caaaagaaca yaagacattt gagcatccac atgaaaaaca acatattta  540
caaaacataa acaaggatat aaaaccacaa tcataaccat aagcatgcat cgtttatttg  600
catttcaata gatcaatcca aaagaaccat ttctataaac actatcctct atcaacagtt  660
```

-continued

```
tacctaaact aaagaaatat tatccataca ataagcatca aacttgcatg tctttgtacc   720
tttcttttgg tggcagcagt accacttcca tcggacttct cagcctcagc cttgagatca   780
accttcaagt cctcaacaac actcttgctc tcaagatccc aaatcttaat accctgctca   840
gtcgcagcac aaagccagta cctattagga ctaaagcaaa gagcgtgaat cacagagttg   900
gcttcaagag agtaaagctt cttcccctca gccaaatccc agagcaaaac gacaccgtct   960
ttgcctccac tagcacacag agaaccatca ggcgacacag c                      1001
```

SEQ ID NO: 62          moltype = DNA   length = 1002
FEATURE                Location/Qualifiers
variation              502
                       note = where n is an insertion/deletion [+/A]
source                 1..1002
                       mol_type = other DNA
                       organism = Brassica napus
SEQUENCE: 62

```
aaaaacacat ccaaggagag agacagggca aagagatggg ataaactagt aacggccaat   60
accccaaact ctgataactc catcggtgta tccactgaac aaggtgcttc catccgcact   120
ccagctcagg ctagtgcagt aaataacctg tccaaaaaag taaatgttta agtctagttt   180
ctcaatctag gcaagaaaaa aaaacagttc ttaccaaaat ataaaaacat tcaaaaattg   240
ccatagatag aaaaatctat atcagatcta tcgattacat tcacatattg ataaaacact   300
agccaacaat atactgcaat ctatggcaaa catgtataaa agtaaattca gacaaaagaa   360
cacaagacat ttgagcatcc acatgaaaaa caaacatatt tacaaaacat aaacaaggat   420
ataaaaccac aatcataacc ataagcatgc atcgtttatt tgcatttcaa tagatcaatc   480
caaaagaacc atttctataa ancactatcc tctatcaaca gtttacctaa actaaagaaa   540
tattatccat acaataagca tcaaacttgc atgtctttgt acctttcttt tggtggcagc   600
agtaccactt ccatcggact tctcagcctc agccttgaga tcaaccttca agtcctcaac   660
aacactcttg ctctcaagat cccaaatctt aataccctgc tcagtcgcag cacaaagcca   720
gtacctatta ggactaaagc aaagagcgtg aatcacagag ttggcttcaa gagagtaaag   780
cttcttcccc tcagccaaat cccagagcaa aacgacaccg tctttgcctc cactagcaca   840
cagagaacca tcaggcgaca gccacagt actaacgtaa ccagtgtgac cagcaagagt   900
cgacctcagc ttacagttcg acaagttcca aactttcacg gtcttgtccc acgacgccga   960
cacaatcgtc ggctggagcg tgttgggact gaacctaacg ca                     1002
```

SEQ ID NO: 63          moltype = DNA   length = 1001
FEATURE                Location/Qualifiers
source                 1..1001
                       mol_type = other DNA
                       organism = Brassica napus
SEQUENCE: 63

```
ggccaatacc ccaaactctg ataactccat cggtgtatcc actgaacaag gtgcttccat   60
ccgcactcca gctcaggcta gtgcagtaaa taacctgtcc aaaaagtaa atgtttaagt   120
ctagtttctc aatctaggca agaaaaaaaa acagttctta ccaaaatata aaaacattca   180
aaaattgcca tagatagaaa aatctatatc agatctatcg attacattca catattgata   240
aaacactagc caacaatata ctgcaatcta tggcaaacat gtataaaagt aaattcagac   300
aaaagaacac aagacatttg agcatccaca tgaaaaacaa acatatttac aaaacataaa   360
caaggatata aaaccacaat cataaccata agcatgcatc gtttatttgc atttcaatag   420
atcaatccaa aagaaccatt tctataaaca ctatcctcca tcaacagttt acctaaacta   480
aagaaatatt atccatacaa waagcatcaa acttgcatgt ctttgtacct tctttttggt   540
ggcagcagta ccacttccat cggacttctc agcctcagcc ttgagatcaa ccttcaagtc   600
ctcaacaaca ctcttgctct caagatccca atcttaata ccctgctcag tcgcagcaca   660
aagccagtac ctattaggac taaagcaaag agcgtgaat cacagagttgg cttcaagaga   720
gtaaagcttc ttcccctcag ccaaatccca gagcaaaacg acaccgtctt tgcctccact   780
agcacacaga gaaccatcag gcgacacagc cacagtacta acgtaaccag tgtgaccagc   840
aagagtcgac ctcagcttac agttcgacaa gttccaaact tcacggtct tgtcccacga   900
cgccgacaca atcgtcggct ggagcgtgtt gggactgaac ctaacgcagc tgacccagtc   960
acggtgccct tcgcctcctt cggagattgt gtacttacac t                      1001
```

SEQ ID NO: 64          moltype = DNA   length = 1001
FEATURE                Location/Qualifiers
source                 1..1001
                       mol_type = other DNA
                       organism = Brassica napus
SEQUENCE: 64

```
tccaaaaaag taaatgttta agtctagttt ctcaatctag gcaagaaaaa aaaacagttc   60
ttaccaaaat ataaaaacat tcaaaaattg ccatagatag aaaaatctat atcagatcta   120
tcgattacat tcacatattg ataaaacact agccaacaat atactgcaat ctatggcaaa   180
catgtataaa agtaaattca gacaaaagaa cacaagacat ttgagcatcc acatgaaaaa   240
caaacatatt tacaaaacat aaacaaggat ataaaaccac aatcataacc ataagcatgc   300
atcgtttatt tgcatttcaa tagatcaatc caaaagaacc atttctataa acactatcct   360
ctatcaacag tttacctaaa ctaaagaaat attatccata caataagcat caaacttgca   420
tgtctttgta cctttctttt ggtggcagca gtaccacttc catcggactt ctcagcctca   480
gccttgagat caaccttcaa rtcctcaaca acactcttgc tctcaagatc ccaaatctta   540
ataccctgct cagtcgcagc acaaagccag tacctattag gactaaagca aagagcgtga   600
atcacagagt tggcttcaag agagtaaagc ttcttcccct cagccaaatc ccagagcaaa   660
acgacaccgt ctttgcctcc actagcacac agagaaccat caggcgacac agccacagta   720
ctaacgtaac cagtgtgacc agcaagagtc gacctcagct tacagttcga caagttccaa   780
actttcacgg tcttgtccca cgacgccgac acaatcgtcg ctggagcgt gttgggactg   840
aacctaacgc agctgaccca gtcacggtgc ccttcgcctc cttcggagat gtgtactta   900
cactcccccca gagtgttcca gagcttgatc gtgcggtcac gggaggccga cacgatctga   960
```

```
cggttgtcga gcgagaaggc cacggagagg acgtctttgg t                            1001

SEQ ID NO: 65          moltype = DNA   length = 1001
FEATURE                Location/Qualifiers
source                 1..1001
                       mol_type = other DNA
                       organism = Brassica napus SEQUENCE: 65
tacctaaact aaagaaatat tatccataca ataagcatca aacttgcatg tctttgtacc        60
tttcttttgg tggcagcagt accacttcca tcggacttct cagcctcagc cttgagatca       120
accttcaagt cctcaacaac actcttgctc tcaagatccc aaatcttaat accctgctca       180
gtcgcagcac aaagccagta cctattagga ctaaagcaaa gagcgtgaat cacagagttg       240
gcttcaagag agtaaagctt cttcccctca gccaaatccc agagcaaaac gacaccgtct       300
ttgcctccac tagcacacag agaaccatca ggcgacacg ccacagtact aacgtaacca       360
gtgtgaccag caagagtcga cctcagctta cagttcgaca agttccaaac tttcacggtc       420
ttgtcccacg acgccgacac aatcgtcggc tggagcgtgt tgggactgaa cctaacgcag       480
ctgacccagt cacggtgccc ytcgcctcct tcggagattg tgtacttaca ctcccccaga       540
gtgttccaga gcttgatcgt gcggtcacgg gaggccgaca cgatctgacg gttgtcgac       600
gagaaggcca cggagaggac gtctttggtg tgtccgacga atctgcgagt ggagacgccg       660
gcggcgaggt cccagagacg aagctcgccg tcccagctgc cggaaagcgc gaattggccg       720
tcggaggaga ggacgacgtc ttcgacgaag tgggagtggc cggtgaggcg tctctgggct       780
acgccgtagg atttgtcgtc ctttgtgagt ttccagacga tgatgattt gtcgcgggaa       840
gcggacacga tggtgtcgga gttgtcgatg ggggtggcga ttgcggtgac catgtcggtg       900
tgagcacgca tggtgccctt gaggacgagt ccttccgcca ttgtcgaagt ctggtgaagc       960
ttagggttat cagtttctcg ggggaggcgg agattcagac g                           1001

SEQ ID NO: 66          moltype = DNA   length = 1001
FEATURE                Location/Qualifiers
source                 1..1001
                       mol_type = other DNA
                       organism = Brassica napus SEQUENCE: 66
acaataagca tcaaacttgc atgtctttgt acctttcttt tggtggcagc agtaccactt        60
ccatcggact tctcagcctc agccttgaga tcaaccttca agtcctcaac aacactcttg       120
ctctcaagat cccaaatctt aataccctgc tcagtcgcag cacaaagcca gtacctatta       180
ggactaaagc aaagagcgtg aatcacagag ttggcttcaa gagagtaaag cttcttcccc       240
tcagccaaat cccagagcaa aacgacaccg tctttgcctc cactagcaca cagagaacca       300
tcaggcgaca cagccacagt actaacgtaa ccagtgtgac cagcaagagt cgacctcagc       360
ttacagttcg acaagttcca aactttcacg gtcttgtccc acgacgccga cacaatcgtc       420
ggctggagcg tgtttgggact gaacctaacg cagctgaccc agtcacggtg cccttcgcct       480
ccttcggaga ttgtgtactt rcactccccc agagtgttcc agagcttgat cgtgcggtca       540
cgggaggccg acacgatctg acggttgtcg cgaatctgcg agtggagacg ccggcggcga      600
gtgtgtccga cgaatctgcg agtggagacg ccggcggcga acgaagctcg       660
ccgtcccagc tgccggaaag cgcgaattgg ccgtcggagg agaggacgac gtcttcgacg       720
aagtgggagt ggccggtgag gcgtctctgg gctacgccgt aggatttgtc gtcctttgtg       780
agtttccaga cgatgatgga tttgtcgcgg gaagcggaca cgatggtgtc ggagttgtcg       840
atggggtgg cgattgcggt gaccatgtcg gtgtgagcac gcatggtgcc cttgaggacg       900
agtccttccg ccattgtcga gtctggtgaa gcttagggt tatcagtttc tcggggggagg       960
cggagattca gacgaaatgg cgtcgagagg taagattcag t                           1001

SEQ ID NO: 67          moltype = DNA   length = 1001
FEATURE                Location/Qualifiers
source                 1..1001
                       mol_type = other DNA
                       organism = Brassica napus SEQUENCE: 67
tcagcctcag ccttgagatc aaccttcaag tcctcaacaa cactcttgct ctcaagatcc        60
caaatcttaa taccctgctc agtcgcagca caaagccagt acctattagg actaaagcaa       120
agagcgtgaa tcacagagtt ggcttcaaga gagtaaagct tcttcccctc agccaaatcc       180
cagagcaaaa cgacaccgtc tttgcctcca ctagcacaca gagaaccatc aggcgacaca       240
gccacagtac taacgtaacc agtgtgacca gcaagagtcg acctcagctt acagttcgac       300
aagttccaaa ctttcacggt cttgtcccac gacgccgaca caatcgtcgg ctggagcgtg       360
ttgggactga acctaacgca gctgacccag tcacggtgcc cttcgcctcc ttcggagatt       420
gtgtacttac actcccccag agtgttccag agcttgatcg tgcggtcacg ggaggccgac       480
acgatctgac ggttgtcgag sgagaaggcc acggagagga cgtctttggt gtgtccgacg       540
aatctgcgag tggagacgcc ggcggcgagg tcccagagac gaagctcgcc gtcccagctg       600
ccggaaagcg cgaattggcc gtcggaggag aggacgacgt cttcgacgaa gtgggagtgg       660
ccggtgaggc gtctctgggc tacgccgtag gatttgtcgt cctttgtgag tttccagacg       720
atgatggatt tgtcgcggga agcggacacg atggtgtcgg agttgtcgat ggggtggcg      780
attgcggtga ccatgtcggt gtgagcacgc atggtgccct tgaggacgag tccttccgcc       840
attgtcgaag tctggtgaag cttagggtta tcagtttctc ggggaggcg gagattcaga       900
cgaaatggcg tcgagaggta agattcagtt tatatcagag acaacacaat ggattagggt       960
ttactttat tgggctttga tgattaagtt taatgaatg g                             1001

SEQ ID NO: 68          moltype = DNA   length = 1001
FEATURE                Location/Qualifiers
source                 1..1001
                       mol_type = other DNA
                       organism = Brassica napus
```

-continued

```
SEQUENCE: 68
tacctattag gactaaagca aagagcgtga atcacagagt tggcttcaag agagtaaagc   60
ttcttcccct cagccaaatc ccagagcaaa acgacaccgt ctttgcctcc actagcacac  120
agagaaccat caggcgacac agccacagta ctaacgtaac cagtgtgacc agcaagagtc  180
gacctcagct tacagttcga caagttccaa actttcacgg tcttgtccca cgacgccgac  240
acaatcgtcg gctggagcgt gttgggactg aacctaacgc agctgaccca gtcacggtgc  300
ccttcgcctc cttcggagat tgtgtactta cactcccca gagtgttcca gagcttgatc  360
gtgcggtcac gggaggccga cacgatctga cggttgtcga gcgagaaggc cacggagagg  420
acgtctttgg tgtgtccgac gaatctgcga gtggagacgc cggcggcgag gtcccagaga  480
cgaagctcgc cgtcccagct kccggaaagc gcgaattggc cgtcggagga gaggacgacg  540
tcttcgacga agtgggagtg gccggtgagg cgtctctggg ctacgccgta ggatttgtcg  600
tcctttgtga gtttccagac gatgatggat ttgtcgcggg aagcggacac gatggtgtcg  660
gagttgtcga tgggggtggc gattgcggtg accatgtcgg tgtgagcacg catggtgccc  720
ttgaggacga gtccttccgc cattgtcgaa gtctgtggaa gcttagggtt atcagtttct  780
cgggggaggc ggagattcag acgaaatggc gtcgagaggt aagattcagt ttatatcaga  840
gacaacacaa tggattaggg tttacttta ttgggctttg atgattaagt ttaatgaatg  900
ggtcttgcgt aaatgggctt tttttgtact ggtaagagtt tttttggttt tacttggtgt  960
taagaattta ccaatgttcg agaatcggta actagactag c                    1001

SEQ ID NO: 69              moltype = DNA   length = 1001
FEATURE                    Location/Qualifiers
source                     1..1001
                           mol_type = other DNA
                           organism = Brassica napus SEQUENCE: 69
cctccactag cacacagaga accatcaggc gacacagcca cagtactaac gtaaccagtg   60
tgaccagcaa gagtcgacct cagcttacag ttcgacaagt tccaaacttt cacggtcttg  120
tcccacgacg ccgacacaat cgtcggctgg agcgtgttgg gactgaacct aacgcagctg  180
acccagtcac ggtgcccttc gcctccttcg gagattgtgt acttacactc ccccagagtg  240
ttccagagct tgatcgtgcg gtcacgg
gag gccgacacga tctgacggtt gtcgagcgag  300
aaggccacgg agaggacgtc tttggtgtgt ccgacgaatc tgcgagtgga gacgccggcg  360
gcgaggtccc agagacgaag ctcgccgtcg cagctgccgg aaagcgcgaa ttggccgtcg  420
gaggagagga cgacgtcttc gacgaagtgg gagtggccgg tgaggcgtct ctgggctacg  480
ccgtaggatt tgtcgtcctt kgtgagtttc cagacgatga tggattttgtc gcgggaagtg  540
gacacgatgg tgtcggagtt gtcgatgggg gtggcgattg cggtgaccat gtcggtgtga  600
gcacgcatgg tgcccttgag gacgagtcct tccgccattg tcgaagtctg gtgaagctta  660
gggttatcag tttctcgggg gaggcggaga ttcagacgaa atggcgtcga gaggtaagat  720
tcagttttata tcagagacaa cacaatggat tagggtttac ttttattggg ctttgatgat  780
taagtttaat gaatgggtct tgcgtaaatg ggctttttt gctgttttttt gctgttttttt  840
ggttttactt ggtgttaaga atttaccaat gttcgagaat cggtaactag actagcgcct  900
agacggatta ttcagaacct aaacgagatc tagatattaa cgaattatta atttattta   960
tatttatata aaacatttta atttttaatt ataaaattat t                    1001

SEQ ID NO: 70              moltype = DNA   length = 1001
FEATURE                    Location/Qualifiers
source                     1..1001
                           mol_type = other DNA
                           organism = Brassica napus SEQUENCE: 70
gattcggcag gttattcctg aagatgacaa gcttaatcat cttttttttg tttcgcattg   60
gtgctaaatg tttgtgttga tatatgctgc agaagaaaac aacggagttg ttatcccgga  120
agctcataac tctgatgaag ttgagaaatt ggatacagca gaagaaggtt cattgtagca  180
tgagcatgac attttttgt ttatgcttc tttgttacac tgtttaaaat ttggctatct  240
gtgggtcgtt tattagatgc gtaagacatt aactagtggt taagggaggg ttatactatc  300
atgagattgg atactgattc taatactagg tatcatcctt gctttgcaga cctgaaagac  360
aaggtggaag agtcagcacc ggttcctgat gagcaacaag gttcaatctt ttatcttctc  420
tttctgtctc atttttctta acgtttagtt taatatatct gagtttggcg agtttttattt  480
atttttgctt gtcattggtg rtttcagtgt ccgaggatca tgatcaagaa gtgcaccatg  540
cagtgcataa cccagcgaaa ggttcataga tctctcattc tacagtcttc tcatcttatg  600
agcgttcatg ttgtctggtt gaagatttat ttatctcttt cgtatatttt atccattcag  660
ctaaagagaa ggcagcccaa gagaaggctg ccaaagagga agctgaagaa gaggcagaag  720
caaacaagaa aagacacttg aacgtggtgt tcatcgggca tgttggtatg ctacttgtt  780
gatttctttt catcagctct actttcataa tagatatatc atctgcactt gtttagactc  840
agggcttaaa agcgtatgta acacattctt gaaattagaa tcatgagctt ttagtcggtg  900
tgtttttaact tttaagcttc ttgatttaat ctttacatgg tcaccttttc aattgtagat  960
gctggaaagt ctacaattgg aggacaaatt ctcttcctta g                    1001

SEQ ID NO: 71              moltype = DNA   length = 121
FEATURE                    Location/Qualifiers
source                     1..121
                           mol_type = other DNA
                           organism = Brassica napus
SEQUENCE: 71
acrtttagtt taatatatct gagtttggcg agtttttattt attttttgctt gtcattggtg   60
rtttcagykt ccgaggatca tgatcwagaa gtgcaccatg cagtgcataa cccagcgaaa  120
g                                                                 121

SEQ ID NO: 72              moltype = DNA   length = 1001
FEATURE                    Location/Qualifiers
```

```
source                    1..1001
                          mol_type = other DNA
                          organism = Brassica napus
SEQUENCE: 72
gaacgtggtg ttcatcgggc atgttggtat ggctacttgt tgatttcttt tcatcagctc   60
tactttcata atagatatat catctgcact tgtttagact cagggcttaa aagcgtatgt  120
aacacattct tgaaattagg atcatgagct tttagtcggt gtgttttaac ttttaagctt  180
cttgatttaa tctttacatg gtcacctttt caattgtaga tgctggaaag tctacaattg  240
gaggacaaat tctcttcctt agcggtcagg tggacgaccg acaaatccaa aagtatgaaa  300
aagaagcaaa agaaaaaagt agagaaagct ggtgggtggt tctgattaat ttgaaatgat  360
aaggaattct tttgttctct ttttcttttt gtttttataa acttgttatc gttctgtatg  420
ctaggtatat ggcttatata atggatacaa atgaagaaga gagggcgaag gtatttcctg  480
atttttttatt tatgtttctt wgtgtgctat aaatgtgtca gagatgataa gaattcacgt  540
gtctgtagaa ttttcagcaa tgtttatggt tgaatttaac ttagctaact gttatgactt  600
acttgctaca ttgaacaggg caaaacagtt gaagttggaa gggctcattt tgaaactgcg  660
agtacgagat ttaccatttt ggatgctccg gtaagagacc aacttaaaag aataattttt  720
tgttcacttg tctttatgag agtattttgt tctaattctt ttgcgccttt tttgaacttg  780
tagggtcaca agagttatgt accaaatatg attagtggag catctcaagc ggacattggt  840
gtactggtaa gttattatct taatttggtc ggagtcgtta ctgtgtagtg tgcgtctttg  900
gtaggaagct tattaatttt catgtccttg tccctctgtt gtaggtgatt tcggctcgta  960
aaggtgaatt tgaaacggga tatgagaggg gtgggcagac c                     1001

SEQ ID NO: 73            moltype = DNA   length = 1001
FEATURE                  Location/Qualifiers
source                   1..1001
                         mol_type = other DNA
                         organism = Brassica napus
SEQUENCE: 73
ctacttgttg atttcttttc atcagctcta ctttcataat agatatatca tctgcacttg   60
tttagactca gggcttaaaa gcgtatgtaa cacattcttg aaattaggat catgagcttt  120
tagtcggtgt gttttaactt ttaagcttct tgatttaatc tttacatggt caccttttca  180
attgtagatg ctggaaagtc tacaattgga ggacaaattc tcttccttag cggtcaggtg  240
gacgaccgac aaatccaaaa gtatgaaaaa gaagcaaaag aaaaaagtag agaaagctgg  300
tgggtggttc tgattaattt gaaatgataa ggaattcttt tgttctcttt ttcttttttgt  360
ttttataaac ttgttatcgt tctgtatgct aggtatatgg cttatataat ggatacaaat  420
gaagaagaga gggcgaaggt atttcctgat tttttatata tgtttcttag tgtgctataa  480
atgtgtcaga gatgataaga rttcacgtgt ctgtagaatt ttcagcaatg tttatggttg  540
aatttaactt agctaactgt tatgacttac ttgctacatt gaacagggca aaacagttga  600
agttggaagg gctcattttg aaactgcgag tacgagattt accattttgg atgctccgta  660
aagagaccaa cttaaaagaa taattttttt ttcacttgtc tttatgagag tattttgttc  720
taattctttt gcgccttttt tgaacttgta gggtcacaag agttatgtac caaatatgat  780
tagtggagca tctcaagcgg acattggtgt actggtaagt tattatctta atttggtcgg  840
agtcgttact gtgtagtgtg cgtctttggt aggaagctta ttaattttca tgtccttgtc  900
cctctgttgt aggtgatttc ggctcgtaaa ggtgaatttg aaacgggata tgagaggggt  960
gggcagaccc gtgaacatgt tcaacttgca aaaacattgg g                     1001

SEQ ID NO: 74            moltype = DNA   length = 1001
FEATURE                  Location/Qualifiers
source                   1..1001
                         mol_type = other DNA
                         organism = Brassica napus
SEQUENCE: 74
tcagctctac tttcataata gatatatcat ctgcacttgt ttagactcag ggcttaaaag   60
cgtatgtaac acattcttga aattaggatc atgagctttt agtcggtgtg ttttaacttt  120
taagcttctt gatttaatct ttacatggtc accttttca ttgtagatgg tggaaagtct  180
acaattggag gacaaattct cttccttagc ggtcaggtgg acgaccgaca atccaaaag  240
tatgaaaaag aagcaaaaga aaaaagtaga gaaagctggt gggtggttct gattaatttg  300
aaatgataag gaattctttt gttctctttt cttttttgtt tttataaact tgttatcgtt  360
ctgtatgcta ggtatatggc ttatataatg gatacaaatg aagaagagag gggcgaaggta  420
tttcctgatt tttttattat gtttcttagt gtgctataaa tgtgtcagag atgataagaa  480
ttcacgtgtc tgtagaattt ycagcaatgt ttatggttga atttaactta gctaactgtt  540
atgacttact tgctacattg aacagggcaa aacagttgaa gttggaaggg ctcatttga  600
aactgcgagt acgagattta ccattttgga tgctccggta agagaccaac ttaaaagaat  660
aattttttgt tcacttgtct ttatgagagt attttgttct aattctttgc gcctttttt  720
gaacttgtag ggtcacaaga gttatgtacc aaatatgatt agtggagcat ctcaagcgga  780
cattggtgta ctggtaagtt attatcttaa tttggtcgga gtcgttactg tgtagtgtgc  840
gtctttggta ggaagcttat taattttcat gtccttgtcc ctctgttgta ggtgatttcg  900
gctcgtaaag tgaatttga acgggatat gagaggggtg gcagacccg tgaacatgtt  960
caacttgcaa aaacattggg cgtgtcgaag ctggttgtc t                      1001

SEQ ID NO: 75            moltype = DNA   length = 1001
FEATURE                  Location/Qualifiers
source                   1..1001
                         mol_type = other DNA
                         organism = Brassica napus
SEQUENCE: 75
gctctacttt cataatagat atatcatctg cacttgttta gactcagggc ttaaaagcgt   60
atgtaacaca ttcttgaaat aggatcatg agcttttagt cggtgtgttt taacttttaa  120
gcttcttgat ttaatcttta catggtcacc ttttcaattg tagatgctgg aaagtctaca  180
```

-continued

```
attggaggac aaattctctt ccttagcggt caggtggacg accgacaaat ccaaaagtat   240
gaaaaagaag caaaagaaaa aagtagagaa agctggtggg tggttctgat taatttgaaa   300
tgataaggaa ttcttttgtt ctctttttct ttttgttttt ataaacttgt tatcgttctg   360
tatgctaggt atatggctta tataatggat acaaatgaag aagagagggc gaaggtattt   420
cctgattttt tatttatgtt tcttagtgtg ctataaatgt gtcagagatg ataagaattc   480
acgtgtctgt agaattttca rcaatgttta tggttgaatt taacttagct aactgttatg   540
acttacttgc tacattgaac agggcaaaac agttgaagtt ggaagggctc attttgaaac   600
tgcgagtacg agatttacca ttttggatgc tccggtaaga gaccaactta aaagaataat   660
tttttgttca cttgtcttta tgagagtatt ttgttctaat tcttttgcgc ctttttttgaa   720
cttgtagggt cacaagagtt atgtaccaaa tatgattagt ggagcatctc aagcggacat   780
tggtgtactg gtaagttatt atcttaattt ggtcggagtc gttactgtgt agtgtgcgtc   840
tttggtagga agcttattaa ttttcatgtc cttgtccctc tgttgtaggt gatttcggct   900
cgtaaaggtg aatttgaaac gggatatgag aggggtgggc agacccgtga acatgttcaa   960
cttgcaaaaa cattgggcgt gtcgaagctg gttgtcgttg t                       1001

SEQ ID NO: 76                moltype = DNA   length = 1001
FEATURE                      Location/Qualifiers
source                       1..1001
                             mol_type = other DNA
                             organism = Brassica napus
SEQUENCE: 76
ggtcaccttt tcaattgtag atgctggaaa gtctacaatt ggaggacaaa ttctcttcct   60
tagcggtcag gtggacgacc gacaaatcca aaagtatgaa aaagaagcaa aagaaaaag    120
tagagaaagc tggtgggtgg ttctgattaa tttgaaatga taaggaattc ttttgttctc   180
ttttttctttt tgtttttata aacttgttat cgttctgtat gctaggtata tggcttatat   240
aatggataca aatgaagaag agagggcgaa ggtatttcct gattttttat ttatgtttct   300
tagtgtgcta aaatgtgtc agagatgata agaattcacg tgtctgtaga attttcagca   360
atgtttatgg ttgaatttaa cttagctaac tgttatgact tacttgctac attgaacagg   420
gcaaaacagt tgaagttgga agggctcatt ttgaaactgc gagtacgaga tttaccattt   480
tggatgctcc ggtaagagac aacttaaaa gaataatttt ttgttcactt gtctttatga   540
gagtattttg ttctaattct tttgcgcctt ttttgaactt gtagggtcac aagagttatg   600
taccaaatat gattagtgga gcatctcaag cggacattgg tgtactggta agttattatc   660
ttaatttggt cggagtcgtt actgtgtagt gtgcgtcttt ggtaggaagc ttattaatttt   720
tcatgtcctt gtccctctgt tgtaggtgat ttcggctcgt aaaggtgaat ttgaaacggg   780
atatgagagg ggtgggcaga cccgtgaaca tgttcaactt gcaaaaacat tgggcgtgtc   840
gaagctggtt gtcgttgtga acaaaatgga tgatccaact gtgaactggt cgaaagagag   900
gtatgtgcat tatcctttcg aattcatgct actgttttc gtatctactt ccattcatcc   960
gcgtatgtac tcttgtgcag gtacgatgaa atagaacaaa a                       1001

SEQ ID NO: 77                moltype = DNA   length = 1001
FEATURE                      Location/Qualifiers
source                       1..1001
                             mol_type = other DNA
                             organism = Brassica napus
SEQUENCE: 77
tcaattgtag atgctggaaa gtctacaatt ggaggacaaa ttctcttcct tagcggtcag   60
gtggacgacc gacaaatcca aaagtatgaa aaagaagcaa aagaaaaaag tagagaaagc   120
tggtgggtgg ttctgattaa tttgaaatga taaggaattc ttttgttctc ttttttctttt   180
tgtttttata aacttgttat cgttctgtat gctaggtata tggcttatat aatggataca   240
aatgaagaag agagggcgaa ggtatttcct gattttttat ttatgtttct tagtgtgcta   300
taaatgtgtc agagatgata agaattcacg tgtctgtaga attttcagca atgtttatgg   360
ttgaatttaa cttagctaac tgttatgact tacttgctac attgaacagg gcaaaacagt   420
tgaagttgga agggctcatt ttgaaactgc gagtacgaga tttaccattt tggatgctcc   480
ggtaagagac aacttaaaa saataatttt ttgttcactt gtctttatga gagtattttg   540
ttctaattct tttgcgcctt ttttgaactt gtagggtcac aagagttatg taccaaatat   600
gattagtgga gcatctcaag cggacattgg tgtactggta agttattatc ttaatttggt   660
cggagtcgtt actgtgtagt gtgcgtcttt ggtaggaagc ttattaatttt tcatgtcctt   720
gtccctctgt tgtaggtgat ttcggctcgt aaaggtgaat ttgaaacggg atatgagagg   780
ggtgggcaga cccgtgaaca tgttcaactt gcaaaaacat tgggcgtgtc gaagctggtt   840
gtcgttgtga acaaaatgga tgatccaact gtgaactggt cgaaagagag gtatgtgcat   900
tatcctttcg aattcatgct actgttttc gtatctactt ccattcatcc gcgtatgtac   960
tcttgtgcag gtacgatgaa atagaacaaa aaatggtacc a                       1001

SEQ ID NO: 78                moltype = DNA   length = 1001
FEATURE                      Location/Qualifiers
source                       1..1001
                             mol_type = other DNA
                             organism = Brassica napus
SEQUENCE: 78
aaagtctaca attggaggac aaattctctt ccttagcggt caggtggacg accgacaaat   60
ccaaaagtat gaaaaagaag caaaagaaaa aagtagagaa agctggtggg tggttctgat   120
taatttgaaa tgataaggaa ttcttttgtt ctctttttct ttttgttttt ataaacttgt   180
tatcgttctg tatgctaggt atatggctta tataatggat acaaatgaag aagagagggc   240
gaaggtattt cctgatttttt tatttatgtt tcttagtgtg ctataaatgt gtcagagatg   300
ataagaattc acgtgtctgt agaattttca gcaatgttta tggttgaatt taacttagct   360
aactgttatg acttacttgc tacattgaac agggcaaaac agttgaagtt ggaagggctc   420
attttgaaac tgcgagtacg agatttacca ttttggatgc tccggtaaga gaccaactta   480
aaagaataat tttttgttca yttgtcttta tgagagtatt ttgttctaat tcttttgcgc   540
cttttttgaa cttgtagggt cacaagagtt atgtaccaaa tatgattagt ggagcatctc   600
```

-continued

```
aagcggacat tggtgtactg gtaagttatt atcttaattt ggtcggagtc gttactgtgt    660
agtgtgcgtc tttggtagga agcttattaa ttttcatgtc cttgtccctc tgttgtaggt    720
gatttcggct cgtaaaggtg aatttgaaac gggatatgag aggggtgggc agacccgtga    780
acatgttcaa cttgcaaaaa cattgggcgt gtcgaagctg gttgtcgttg tgaacaaaat    840
ggatgatcca actgtgaact ggtcgaaaga gaggtatgtg cattatcctt tcgaattcat    900
gctactgttt ttcgtatcta cttccattca tccgcgtatg tactcttgtg caggtacgat    960
gaaatagaac aaaaaatggt accatttctt aaatcctctg g                       1001

SEQ ID NO: 79          moltype = DNA  length = 1001
FEATURE                Location/Qualifiers
source                 1..1001
                       mol_type = other DNA
                       organism = Brassica napus
SEQUENCE: 79
ctcttcctta gcggtcaggt ggacgaccga caaatccaaa agtatgaaaa agaagcaaaa    60
gaaaaaagta gagaaagctg gtgggtggtt ctgattaatt tgaaatgata aggaattctt    120
ttgttctctt tttctttttg tttttataaa cttgttatcg ttctgtatgc taggtatatg    180
gcttatataa tggatacaaa tgaagaagag agggcgaagg tatttcctga ttttttattt    240
atgtttctta gtgtgctata aatgtgtcag agatgataag aattcacgtg tctgtagaat    300
tttcagcaat gtttatggtt gaatttaact tagctaactg ttatgactta cttgctacat    360
tgaacagggc aaaacagttg aagttggaag ggctcatttt gaaactgcga gtacgagatt    420
taccattttg gatgctccgg taagagacca acttaaaaga ataatttttt gttcacttgt    480
ctttatgaga gtattttgtt ytaattcttt tgcgcctttt ttgaacttgt agggtcacaa    540
gagttatgta ccaaatatga ttagtggagc atctcaagcg gacattggtg tactggtaag    600
ttattatctt aatttggtcg gagtcgttac tgtgtagtgt gcgtctttgg taggaagctt    660
attaattttc atgtccttgt ccctctgttg taggtattt cggctcgtaa aggtgaattt    720
gaaacgggat atgagagggg tgggcagacc cgtgaacatg ttcaacttgc aaaaacattg    780
ggcgtgtcga agctggttgt cgttgtgaac aaaatggatg atccaactgt gaactggtcg    840
aaagagaggt atgtgcatta tcctttcgaa ttcatgctac tgtttttcgt atctacttcc    900
attcatccgc gtatgtactc ttgtgcaggt acgatgaaat agaacaaaaa atggtaccat    960
ttcttaaatc ctctggctac aacacaaaga aaggtatgca g                       1001

SEQ ID NO: 80          moltype = DNA  length = 760
FEATURE                Location/Qualifiers
source                 1..760
                       mol_type = other DNA
                       organism = Brassica napus
SEQUENCE: 80
aattcttttg ttctcttttt cttttgttt ttataaactt gttatcgtct tgtatgctag     60
gtatatggct tatataatgg atacaaatga agaagagagg gcgaaggtat ttcctgattt    120
ttttatttat gtttctttgt gtgctataaa tgtgtcagag atgataagag ttcacgtgtc    180
tgtagaattt cagcaatgt ttatggttga atttaactta gctaactgtt atgacttact    240
tgctacattg aacagggcaa aacagttgaa gttggaaggg ctcattttga aactgcgagt    300
acgagattta ccattttgga tgctccggta gagacmaac ttaaaasaat aattttttgt    360
tcacttgtct ttatgagagt attttgttct aattcttttg cgcctttttt gaacttgtag    420
ggtcacaaga gttatgtacc aaatatgatt agtggagcat ctcaagcgga cattggtgta    480
ctggtaagtt attatcttaa tttggtcgga gtcgttactg tgtagtgtgc gtctttggta    540
ggaagcttat taatttcat gtccttgtcc ctctgttgta ggtgatttcg gctcgtaaag    600
gtgaatttga acgggatat gagaggggt ggcagacccg tgaacatgtt caacttgcaa    660
aaacattggg cgtgtcgaag ctggttgtcg ttgtgaacaa aatggatgat ccaactgtga    720
actggtcgaa agagaggtat gtgcattatc ctttcgaatt                         760

SEQ ID NO: 81          moltype = DNA  length = 201
FEATURE                Location/Qualifiers
source                 1..201
                       mol_type = other DNA
                       organism = Brassica napus
SEQUENCE: 81
ccagakgcaa aacygaatgt aagagaacat tactattaga aatcgagatc aagcttcctc     60
ttcagatgag atctatcggc actacaaaat gaacaacaac ragaagcttt taaaacacat    120
wcaakcttga gmctgtaaaa acaactaatc aaagagatcg ctctatttgc wcmtggtgat    180
ggttggtcgg kkaggaggcc g                                             201

SEQ ID NO: 82          moltype = DNA  length = 121
FEATURE                Location/Qualifiers
source                 1..121
                       mol_type = other DNA
                       organism = Brassica napus
SEQUENCE: 82
yagaaactgg tcgatgaggt aaccatgtgc accgtgaacc tccaccccat caaagcctat     60
rawtamcaca agtgtcatgt tcagctaaca tyatacatcc aaaggggaaa aagactttc    120
t                                                                   121

SEQ ID NO: 83          moltype = DNA  length = 121
FEATURE                Location/Qualifiers
source                 1..121
                       mol_type = other DNA
                       organism = Brassica napus
SEQUENCE: 83
```

-continued

```
ratgcatttt cttcatcatt ggtaacatgg tgctttatgt yaacaataaa acctcttaat    60
ragctctaac tgattcgtaa tgaaaccaaa catatataaa taaacaatct tagatttgat   120
g                                                                   121

SEQ ID NO: 84            moltype = DNA   length = 121
FEATURE                  Location/Qualifiers
source                   1..121
                         mol_type = other DNA
                         organism = Brassica napus
SEQUENCE: 84
gtctttatc ttatttcaaa atatattagg tgtgacatgt gaaaaggttc tagaaactgg     60
ktggttatgc ttcctagact ccatcaagaa ataaagctga attgtttttt tacmcatcca   120
c                                                                   121

SEQ ID NO: 85            moltype = DNA   length = 121
FEATURE                  Location/Qualifiers
source                   1..121
                         mol_type = other DNA
                         organism = Brassica napus
SEQUENCE: 85
aaactggktg gttatgcttc ctagactcca tcaagaaata aagctgaatt gtttttttac     60
mcatccactc attttkatc aaacaggtac aagagaagaa gatcaagaaa atttctgaaa    120
t                                                                   121

SEQ ID NO: 86            moltype = DNA   length = 121
FEATURE                  Location/Qualifiers
source                   1..121
                         mol_type = other DNA
                         organism = Brassica napus
SEQUENCE: 86
yactgcgata tcatctccta ttatacycca tgtttctttg aagaactctg ysgtataacc     60
rtctggccct ggagctttgc ttcctggcat cttaaataaa actcctttga tttcttcttt   120
r                                                                   121

SEQ ID NO: 87            moltype = DNA   length = 121
FEATURE                  Location/Qualifiers
source                   1..121
                         mol_type = other DNA
                         organism = Brassica napus
SEQUENCE: 87
attattagtt tttccaaaat caaatgttat tagattgtac atataaaaaa aaacctaaga     60
raaaamaact catctcattc ttttatacta agakggtcta aagaaattaa tgatataaaa   120
a                                                                   121

SEQ ID NO: 88            moltype = DNA   length = 1001
FEATURE                  Location/Qualifiers
source                   1..1001
                         mol_type = other DNA
                         organism = Brassica napus
SEQUENCE: 88
ctatgtgtag tagataaagt atggtactga ccataggtat gtgacatttt agtttatatt     60
gaatgttaat atttgatatt gtatgctaac tataaacaca tgtgttattt taatagttga   120
accacaacca aagtcagcct ctatacatga ttacatccag ctggagatta catgacacat   180
gcaccagagg catacacact tggatctcta atcctaacac ctccaattac aggccaaaga   240
agacaaggat gttgttaaaa ggtgaattca aggtagacct aagctaactt cagctgatac   300
tgaacttgca ctgatgtgat tgttattaat atcattaatc gttattgaaa gttctcaaca   360
tcaaattgat tgttcatgaa acaaggtgtc atagggtgaa gagaaagaac ctgtaggaag   420
tgtggtgaaa ctgatcacag tcgcgctctc tgcaaaataa tgtataacac tattacttag   480
cggttacaca ttagttttga rccttgaagt tcacttgaaa acacgtagga gagaagcaaa   540
tagaacagcc actagcgtga tgcagatagg aatgcctata aacatgtgtg cagttgtatt   600
cttgagaagg tggatgatat ggcagatcct tgtggcttga tgattcagta cataaaaggg   660
catatcagtt tctttgaaaa aggttctttg ttgtacctat aaaagaaagg agattgtttc   720
aaaaaagaac tacataaatc atgctagaga ctggatccag agtataaata ttcacctctt   780
cgtttggttt gtccctaaaa tgttctacag aatcagcttc ttcaagggaa tcacatccgt   840
gtgcatcaag aaactgtaga ctcagtggga gtttttccac tgatctgaga ttcttgcagt   900
tattaaggca aagagttacc agtgaggtaa gatctctgat gcttgatggc aatgcaacaa   960
actcatggcc gctgagatct aaatttgtca acttaatgaa a                      1001

SEQ ID NO: 89            moltype = DNA   length = 201
FEATURE                  Location/Qualifiers
source                   1..201
                         mol_type = other DNA
                         organism = Brassica napus
SEQUENCE: 89
gagaaagaac ctgtaggaag tgtggtgaaa ctgatcacag tcgcgctctc tgcaaaataa     60
tgtataacac tattacttag cggttacaca ttagttttga rccttgaagt tcacttgaaa   120
acacgtagra gagaagcaam tagaacagcs actagcgtga tgcagatagg aatgcctata   180
aacatgwgtg cagttgtatt c                                             201
```

-continued

```
SEQ ID NO: 90            moltype = DNA   length = 301
FEATURE                  Location/Qualifiers
source                   1..301
                         mol_type = other DNA
                         organism = Brassica napus
SEQUENCE: 90
aatggaactt cagttgataa tggagtwtat gaaggargga acacttgaag tcttccctgt   60
cttctatgga gttgatcctt ccaccgtcag gcatcagcta gggagtttct ctttagaacg  120
gtacaagggt cgtccagaaa tggtgcacaa rgttcacaag tggagagaag ctcttcacct  180
aatagctaac ctttcaggcc tggattcaag acaytggtaa gctcttctta ccataatata  240
gttacaaaaa tatatatact tacgtctttt ctttaaaaat atattttcta gtgttttcac  300
a                                                                   301

SEQ ID NO: 91            moltype = DNA   length = 229
FEATURE                  Location/Qualifiers
source                   1..229
                         mol_type = other DNA
                         organism = Brassica napus
SEQUENCE: 91
tttaaattta gtgactaaac cagaatgaga caggtgaaac tcctagcgag atactattac   60
cttacgcgct ttgattagtt tgttttgagt ctctagcttt gcacgttgct ccctcctcct  120
cataattgca tggagctgct tcrcattgac aaagacaggc tcatcttcaa tgaggtccag  180
tggtaaagga acccgaccca ccatttgggg attccatacc tgcaggtct               229

SEQ ID NO: 92            moltype = DNA   length = 229
FEATURE                  Location/Qualifiers
source                   1..229
                         mol_type = other DNA
                         organism = Brassica napus
SEQUENCE: 92
tttaaattta gtgactaaac cagaatgaga caggtgaaac tcctagckag atactattac   60
cttacgcgct ttgattagtt tgttttgagt ctctagcttt gcacgttgct ccctcctcct  120
cataattgca tggagctgct tcgcattgac aaagacaggc tcatcttcaa tgaggtccag  180
tggtaaagga acccgaccca ccatttgggg attccatacc tgcaggtct               229

SEQ ID NO: 93            moltype = DNA   length = 121
FEATURE                  Location/Qualifiers
source                   1..121
                         mol_type = other DNA
                         organism = Brassica napus
SEQUENCE: 93
aaccaaaaga gtgtgcggtt tgatactcaa agtagtagtg atcttgaaac tgtggtgaga   60
yctttggta aacacawctc gcaagtgttg ttttgccaac tytttcctca ccacaaatgc  120
c                                                                   121

SEQ ID NO: 94            moltype = DNA   length = 121
FEATURE                  Location/Qualifiers
source                   1..121
                         mol_type = other DNA
                         organism = Brassica napus
SEQUENCE: 94
ctcaaatatc tgaaaatyta caaccacagg cgttacaaaa gtttagattc waggacacag   60
rgcaatccaa acgaaatttt acaaccttat aaacttagat tgctacagtg ggatgcatat  120
c                                                                   121

SEQ ID NO: 95            moltype = DNA   length = 970
FEATURE                  Location/Qualifiers
source                   1..970
                         mol_type = other DNA
                         organism = Brassica napus
SEQUENCE: 95
aaccggagat gaccatcatt acctagctat tgcccatcgt cttacataga agaagcacac   60
ccaaacatag agcaaaagcc attagtttca aggtttcgga gctaaaacgg tctgtgtaga  120
ttgttctgac actcctcatc cctcgatcaa gcgtattcaa tatcttaggt ttctgggatt  180
aagcacatag ctgtacctat taaacgaaat aaaaggaagt tagctttgcg tatagagatt  240
gagagaataa ggattacagt agagggttgt tttacctctt cactacgtct tcctgatgga  300
aaacgagtga attgacttaa aaactgattc ggttggaagc aagggctgag atcaaggtca  360
tcaacagaat gatcaactga aagggagaaa gtttctaagg acatgcagcc atgtgaatat  420
aggtgcttaa tgctcaatgg aagctctgaa agtgatttta gtttcatgca atagttgagg  480
cagagagtta tcagcgagga kaggtctttg atgcttgtag gcactgtttc aaaatcgtgg  540
cgactgatat ctaaatacgt caactttgta aaaaaccgaa gctgatccga caatgtctcg  600
acatgtttgc agttgtcaag acgaagctca agcaaattgt attttccatg gtcttgttct  660
gcctgcgaaa tgctcaccaa tgtgtggagg ttggtacaat cagaaagtgt gagcgtctcc  720
agctgatata gttgtggcaa agcttcaagt ctacgacagt tacaaagcct cacatgtttt  780
aacttcgtaa gatgagtcat tgatgaaggt aaacccctga agaagtttcc acttaggttc  840
aacttctcta gaacttgcat gtgatgaatg tcatctggta tttcttcgat gtttaagttg  900
attagattta gctccatcaa ccagggaaaa tatgaaaagc tataacactc gaaaggatcc  960
ctttgctcac                                                          970
```

-continued

```
SEQ ID NO: 96          moltype = DNA   length = 201
FEATURE                Location/Qualifiers
source                 1..201
                       mol_type = other DNA
                       organism = Brassica napus
SEQUENCE: 96
gataaaatgg tttgattgat aagtaacctt gcaaatgtag gaaacatatt aagaacagaa    60
agcttcaact tcaattctat tgagagaaag aaaaaagcca yaaagaagca aatactgyac   120
ctctcctgca taatgcgata tcgtaaaatc agtctgagag agcttcggtt tggaaaatct   180
ctcgtgacct ttgaacgtct g                                             201

SEQ ID NO: 97          moltype = DNA   length = 301
FEATURE                Location/Qualifiers
source                 1..301
                       mol_type = other DNA
                       organism = Brassica napus
SEQUENCE: 97
acatgtgtat gataaatcaa ttgcaaaaca agaaaaatat attatttgtc catcaagaaa    60
ctgatacctt gatgactaaa ttttgtagct ttggggtctt tctgagcaga cgtggcagaa   120
cttgccagct tttatccttg tcgctctcga rtgataaagt aacgaggttg tcgaatgtga   180
agatcaattt gcagccgaaa tgaagcgcct aatgcatgta ttatcgaaac cataagcata   240
tatacagata tatatattca taatagattt atgaattaat tttattttag ttttactatt   300
t                                                                   301

SEQ ID NO: 98          moltype = DNA   length = 121
FEATURE                Location/Qualifiers
source                 1..121
                       mol_type = other DNA
                       organism = Brassica napus
SEQUENCE: 98
acaataaatt tataattgtt aaccragtgg tcttggccta gtggtaaatg agttctacct    60
rgagtttctg ccctaggttc gattcccgga ttaagtggca agaaaaaccg gatttatatg   120
g                                                                   121

SEQ ID NO: 99          moltype = DNA   length = 698
FEATURE                Location/Qualifiers
source                 1..698
                       mol_type = other DNA
                       organism = Brassica napus
SEQUENCE: 99
agctttcaca aatctccacc agcttggttt aagcccaacc ttggcccatc cgacaaccct    60
agtgccgaca gcttcctccc ttgtctcttt gtctttcttg tgaaatgaga aagtcgatct   120
tgactctctc tctctcttcc tcgtctctct cactcgcgac ccttctccgc cgattcggac   180
ttggtgtcgt cgtgaggagt tataggttgc tctgcctcgc aaccgtagct ccatgaaggt   240
ctcgtcagct ccaccgcgat ggcgtcgcat ctccttctct ccattcttcc ctcgaagtyt   300
cttcgccgaa cggcgatttg cttctctgat gatggctcac accatcgtga ctccatcatc   360
tttcctccct aatatcccca ggtacatcta atctctcctc ttcatgagcg attaggatca   420
tctgttaggg atactaagtg agtcttgtgg gaacttgagc taacttgagg attctttgcc   480
tttgcatgtc gtctcaggtg actcgtgact ctatctctag tcgcgattga gaacctgaca   540
tgtcggtaag ctcttgcctg agctccatca tcacgctcta cctctttcgt agataacgta   600
agctcatgtc ttaacgaacc ttctctaata tgctttttac ttgtcgatct gactcttctg   660
tttctgtttc agaagccggt ttagctctgt gacgagct                          698

SEQ ID NO: 100         moltype = DNA   length = 749
FEATURE                Location/Qualifiers
source                 1..749
                       mol_type = other DNA
                       organism = Brassica napus
SEQUENCE: 100
agcttctggg cagaggcagc atctactgct atccatgtga tcaatagatc acctaactct    60
acactcgagt tcagaatgcc tgaagaattg tggaccggcg cgaaacctga cttgggacat   120
ctaagaactt ttggatgcac tgcgtatgtc cacataactg aggagaaaac aggacctaga   180
gccatcaaag gggtgtttgt ggggtaccct atgggtacta aaggctatcg agtttggata   240
gaggatgarg gcagatgcag aacaagtaga aatgttgttt tcaacgaaga cgagctatac   300
aagcacaccg ttgctaaagc aaaagaaagc acaggagtga ctaaagatac agagaaacga   360
gctaaaaaga gggtctcatt cagtgatgat ttgatcagag ggccttctcc ttctgtcgaa   420
tccaaagaca catctgatca aggtggagaa gaatcatcat catctgagga gtcgagtagt   480
tcgagtgacc aagaacagaa tgacgaggtt gaaagtgaaa gtggtgacac tggatcttta   540
gacacctatg ttctagctcg agacagagca agaagacgaa acgtgaggcc cccatctcgc   600
tatgaggatg gaaactttgt agcctatgcg ctaaatgtca tcaacgactt agaggttgaa   660
gaacctaaat cctacgctga ggcaatgaaa agtccacaga agaagttgtg gaaaaatgca   720
gctgaggagg agatggaatc tcataggaa                                     749

SEQ ID NO: 101         moltype = DNA   length = 574
FEATURE                Location/Qualifiers
source                 1..574
                       mol_type = other DNA
                       organism = Brassica napus
SEQUENCE: 101
```

-continued

```
aattcttgaa gctagttgca gatttaaaca atttgcaagt tgaagtatcc gaggaagttc    60
aagctatcct attgctaagt tctctaccaa acaagtatga tcaactcaaa gagactctca   120
agtatggaag agacacccta agcctagctg aggttacagg ggctgcaagg tcgaaagaaa   180
gagagttgat tgagagtggt aagtttacca ggtctggtgg agaaggtctg atggtgacag   240
acagagaag atcagaccaa cgctctggca aaggaaatga aaaatcctac aggggaagat    300
ccaagagcag acagggacgt tccaagtcgc gtcctaggaa caccaaaggc tcaaagggat   360
gttttgtatg cgggaaggag ggccactgga agcgtgactg ccctgataag aaaccttaca   420
aaacgccaga ctcagcaaat gttgtggcag agtccaakga acctctaatc ctcaccgtga   480
gcacccaata ctccaaggac gaatgggtga tggactctgg ctgctcgttc cacatcacac   540
cagacaagag tttttttgttt gacctggaag aatt                               574
```

SEQ ID NO: 102      moltype = DNA  length = 524
FEATURE            Location/Qualifiers
source              1..524
                   mol_type = other DNA
                   organism = Brassica napus SEQUENCE: 102
```
agcttctcat cggtgagaat agctttcagt ccaagcactc caaagtgagc aagcattctc    60
actttccata gggcgaagtc accatctcct tcgaaacggt cgatctcgat gcgttccttt   120
gacttcaccw ttgagaaggt actgagtatg cacctcctct gtctctctct ctatcctaag   180
caaccttgat gaaaaccgga gctctgatac cacttgtaga atgtaattag ctcaggttaa   240
cttaggttag aggttatatt gatctaggtc taatactgaa agtaaagaca caagcgattt   300
aacgacttcc cggccctcgg cgcggtacgt gtcgtgggag aacttctgct cccaaaatcc   360
actagatcaa agagtctcta gcaccactaa atcagtgtgc tagataggta ggttacaata   420
agatcccttc aacttagcta gggaatacaa caaccttaat atgagacaat agccttaagt   480
ctaagctagt tgtccttgtt gaagtctcct ttcccttgat gctg                     524
```

SEQ ID NO: 103      moltype = DNA  length = 681
FEATURE            Location/Qualifiers
source              1..681
                   mol_type = other DNA
                   organism = Brassica napus SEQUENCE: 103
```
aaagtgagca agcattctca ctttccatag ggcgaagtca ccatctcctt cgaaacggtc    60
gatctcgatg cgttcctttg acttcaccat tgagaaggta ctgagtatgc acctcctctg   120
tctctctctc tatcctaagc aaccttgatg aaaaccggaa gctctgatac cacttgtaga   180
atgtaattag ctcaggttaa cttaggttag aggttatatt gatctaggtc taatactgaa   240
agtaaagaca caagcgattt aacgacttcc cggccctcgg ctcggtacgt gtcgtgggag   300
aacttctgct cccaaaatcy actagatyaa agagtctcta gcaccactaa atcagtgtgc   360
tagataggta ggttacaata agatcccttc aacttagcta gggaatacaa caaccttaat   420
atgagacaat agccttaagt ctaagctagt tgtccttgtt gaagtctcct ttcccttgat   480
gctgtatctt gttgactgat ctctgatgct ataacctgct gttgttgctt ctatccggta   540
accctaatca cccatactaa cattgtatat atatgtgtcg tatgtgatca ggtagtgcaa   600
cctggagtgg gcctgcgcat gacttcggcc catcagatgt gatgctgctg ctggcccatc   660
acgcagggat aaacccaagc t                                             681
```

SEQ ID NO: 104      moltype = DNA  length = 519
FEATURE            Location/Qualifiers
source              1..519
                   mol_type = other DNA
                   organism = Brassica napus SEQUENCE: 104
```
gctgcaatcg ccttttgtgg gaggttgatg caagggaata gatacatagc tccttcagct    60
ctgttgcatg ttacaccktc taacttgttc aaagcttctt caagggtctg tgtggctcaa   120
ctcaaaactc attaaaacca taacaaaaat ctagttccat gattgctagt aagttctgtg   180
agaatggcta acctttgcac gtgttgctaa agacgagagg atcccctctt tctctgctat   240
gtatgaatca tacgagtcat caccaggctg atcaaattac attaaagagc tgttaaagac   300
aattgagctt ttaaaccaaa ccagctgtta aagtaataca ataccttggg agggctcatg   360
acgaggctgg cgagaatttg accagagatg ttggagcaaa gattgacaga agccactttg   420
tatatctgtt ctcttacatc agaagtgaat ccggtaacct ccatgtaacc gcctctcttc   480
ccacactctc cataataccc tattgaaaga aaggagtac                           519
```

SEQ ID NO: 105      moltype = DNA  length = 946
FEATURE            Location/Qualifiers
source              1..946
                   mol_type = other DNA
                   organism = Brassica napus SEQUENCE: 105
```
tatatgttct gaacctcact acaattcagc atctgagctt gtttttttttt ctttcttcta    60
gtggtgtaag attttgttta accaatggat gttgcaattt ttctatcagt tcggattcta   120
ttgatcgtgc ttggaagatc ctcgaccaaa tccccgggaa agctaccggt gcttacagcc   180
acagccaggt tttgtggcct ttgtcaatct taaacagtga atgatggatg atacactctc   240
ttaatcttct gctttgtctc tcagggtatc aagggactgt gtgatcgat agctgctgga    300
atcgaagccc gtgacggttt ccctgctgat cctaatgata ttttcatgac agatggtgca   360
agccctgggg taaccagtca tcaaactttc cctaaactta tataaattac agaaaaaagg   420
ttagtaatgt tactctcgtt ctttttaggtt cacatgatga tgcaactcct cataagttca   480
gagaaagatg gaatcctttg ycctattcct cagtacccct tgtactcagc ttctattgcc   540
cttcacggcg gtagtctggt atgttccttt atgtctctct gatgcatgtc tatagtgact   600
tctgattgct gtcatcttct tgaggtaggt tccatactac ctagacgaag catcagggtg   660
```

```
gggtcttgaa atatctgagc tgaagaagca gcttgaggat gctaagtcaa aaggcatcac   720
tgtaagagcc ttggcggtta ttaaccctgg taaccctaca ggacaggtaa agactaaacc   780
acaaatctat ttccatccaa attcaacact ttgtctgaac tctagcctgt tattttcctg   840
gttaaaggtt ctgtcagaag aaaaccagcg tgacattgtt gatttctgta agaaagaagg   900
cttggtgctt ctagcagacg aggtttatca ggaaacgttt acgtcc               946

SEQ ID NO: 106          moltype = DNA   length = 121
FEATURE                 Location/Qualifiers
source                  1..121
                        mol_type = other DNA
                        organism = Brassica napus
SEQUENCE: 106
tctcgtgacc cataatcaag cattgaatat atattctgag agaagccata tatattcaaa   60
ytaattaaaa actaatmtat tcwgaaagta twgtgaaata ttgaatatta cgagcaagta   120
g                                                               121

SEQ ID NO: 107          moltype = DNA   length = 121
FEATURE                 Location/Qualifiers
source                  1..121
                        mol_type = other DNA
                        organism = Brassica napus
SEQUENCE: 107
atcaacaaga gaaaagctaa caagacttgc acataaytct aaacaggaag aaaaactgag   60
yagaacatga acagagacca aaaggtccaa aactgatttg atttaagggc cagtttgaat   120
a                                                               121

SEQ ID NO: 108          moltype = DNA   length = 408
FEATURE                 Location/Qualifiers
source                  1..408
                        mol_type = other DNA
                        organism = Brassica napus
SEQUENCE: 108
agtttggttt aatgtgatta acaattgtgg tttaggtgta tggtccaacg aggttgatat   60
ggggagcgaa aggagaggag caagaggcgg ggacgaagga gttcattgag atgctcaaga   120
tgctagagtc tgagcttgga gacaagactt actttggagg ygaaacattc ggttatgtgg   180
atatagctat gattggattc tactgctggt tcgacgtttt ggagaagtgt gggaatttta   240
gcatcgaagc agagtgtcca aagctgattg cttgggctaa aaggtgtatg aagagagaga   300
gtgtggctaa gtctcttcct gattcaaaca agatcactaa gttcgttcct gagctaaaga   360
aaaaaattgg catcgagtag ttctgttata atttaatctg tgttctgt               408

SEQ ID NO: 109          moltype = DNA   length = 301
FEATURE                 Location/Qualifiers
source                  1..301
                        mol_type = other DNA
                        organism = Brassica napus
SEQUENCE: 109
tgaagcataa cctcaaacgc ctcagcaaca tcttcacagt aaagatagct acgaacatta   60
gtaccatctc tatgaatagg aagagctttc cctcttatca ccaacaaaaa taaacttagg   120
tccaacaaca gcatcttcat ctgtctcagc yatwaacctc atctgctctc acatgtataa   180
mcctcctgat ctatcctcta gtcactttac aagcctcgag aaggacatgc gttccgtaga   240
tattgttttt tagtgaactc gaaactgtta cggaaggagt tgtccacgtg agttctgtga   300
g                                                               301

SEQ ID NO: 110          moltype = DNA   length = 301
FEATURE                 Location/Qualifiers
variation               242..271
                        note = where n is a, t, c, or g
source                  1..301
                        mol_type = other DNA
                        organism = Brassica napus
SEQUENCE: 110
acaaagctgt aattaaaaga taagacacga gtttcggttt ggttttgtgg ataaaaggat   60
aagaagagca ttttcccctt ttttatcgta atttttgttt tataaaagga taattatatt   120
aagtttattt tgtttataca acgatcaatg ktttttgtaa ttctcattta tataacgatt   180
ctcacacctt tattgtttta gatggatatg ttgggtgaca actcacaagt agattttttc   240
annnnnnnnn nnnnnnnnnn nnnnnnnnnn ngctagttgg taaaaagaaa aagaaagaa   300
g                                                               301

SEQ ID NO: 111          moltype = DNA   length = 1212
FEATURE                 Location/Qualifiers
variation               78
                        note = where n is a, t, c, or g
variation               1113
                        note = where n is a, t, c, or g
source                  1..1212
                        mol_type = other DNA
                        organism = Brassica napus
SEQUENCE: 111
cccgcgtccg ctgacggaca cggagatggc attgtgttac tggaaagctc tgttactact   60
```

-continued

```
actgctttca tgcctctntc agtgtttcgt atgctagtct cggcgatgcc gatccaaact   120
acagggcatg tgttggagaa tgcgagataa gcggctgcgt tggacaacta tgctttcctc   180
agtgcaactc ttcatccaac actggtccat ggtacacaca agagcctctg tacctacaat   240
ggcaaaagtg gggatgtcaa ggtgattgcc gttaccactg tatggttaac agagagaaag   300
aacgcgaaac tctcggtcaa cccccactca agtatcatgg taaatggcct ttcaagcgtc   360
tccttgggat tcaggagcct gcttctgttg ctttctctgt gctcaaccta gcgatgcatt   420
tccacggctg gatctccttc ttcattacgc tttactataa gctgcctctc agagaagata   480
agacggctta ctatgaatac gttggtctgt ggcatatcta cggtttcttg tcaatgaact   540
cttggttctg gagtgcggtt ttccacactc gggatgttga catcactgag aggttggact   600
actcgtctgc aatagcggtt atcggattct cactcattgt atccatcttg agaacgtttg   660
atgttcgggt agaggctgca agagtcatgg tatctgctcc agtgctagct tttgtcacca   720
ctcacatact gtatattaac ttctacaagc tcgactatgg ttggaacatg attgtgtgtg   780
tggccatggg agtcgctcag cttctcctat gggcaagatg ggctgctgtc tctagacatc   840
cttctaastg gaaactttgg atggtggtga tagcttcagg cttagctatg cttttggaga   900
tatatgactt tcctccatat gaaggctact tcgatgctca ctccatttgg catgctgcaa   960
ccattcctct aactgttctc tggtggagct ttattagaga cgatgctgag ttcagaactt  1020
ctagtcttct caagaaatct aagacaaagg ctaagtaagc ttatttgtct gacagatgca  1080
gaggtttctt gagtttttat ttccaatgtt ttntattcag agatttgtct tggccgtcct  1140
tacttttggt caattgagat ttgatattag tttctcattc atacacacgc ttatgctaat  1200
cttttttggac tc                                                       1212
```